(12) United States Patent
Vlaar et al.

(10) Patent No.: US 10,995,096 B2
(45) Date of Patent: *May 4, 2021

(54) 1,5-DISUBSTITUTED 1,2,3-TRIAZOLES ARE INHIBITORS OF RAC/CDC42 GTPASES

(71) Applicant: UNIVERSITY OF PUERTO RICO, San Juan, PR (US)

(72) Inventors: Cornelis P. Vlaar, San Juan, PR (US); Suranganie Dharmawardhane Flanagan, San Juan, PR (US); Eliud Hernandez-O'Farrill, San Juan, PR (US); Linette Castillo-Pichardo, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/814,214

(22) Filed: Mar. 10, 2020

(65) Prior Publication Data

US 2020/0239487 A1    Jul. 30, 2020

Related U.S. Application Data

(63) Continuation of application No. 16/456,641, filed on Jun. 28, 2019, which is a continuation of application No. 15/970,268, filed on May 3, 2018, now Pat. No. 10,392,396, which is a continuation of application No. 15/499,532, filed on Apr. 27, 2017, now Pat. No. 9,981,980.

(60) Provisional application No. 62/328,282, filed on Apr. 27, 2016.

(51) Int. Cl.
| | | |
|---|---|---|
| *C07D 401/14* | (2006.01) | |
| *C07D 403/04* | (2006.01) | |
| *C07D 403/14* | (2006.01) | |
| *C07D 491/048* | (2006.01) | |
| *C07D 409/14* | (2006.01) | |

(52) U.S. Cl.
CPC ....... *C07D 491/048* (2013.01); *C07D 401/14* (2013.01); *C07D 403/04* (2013.01); *C07D 403/14* (2013.01); *C07D 409/14* (2013.01)

(58) Field of Classification Search
CPC ... C07D 401/14; C07D 403/04; C07D 403/14
See application file for complete search history.

(56) References Cited

U.S. PATENT DOCUMENTS

| | | | |
|---|---|---|---|
| 4,835,258 A | 5/1989 | Hollenberg et al. | |
| 5,298,520 A | 3/1994 | Baker et al. | |
| 8,884,006 B2 | 11/2014 | Hernandez et al. | |
| 9,028,796 B2 | 5/2015 | Maltese et al. | |
| 9,169,234 B2 | 10/2015 | Blagg | |
| 9,278,956 B1 | 3/2016 | Hernandez et al. | |
| 9,981,980 B2 | 5/2018 | Vlaar | |
| 2012/0022118 A1 | 1/2012 | Demko | |
| 2017/0015635 A1 | 1/2017 | Madadi et al. | |

FOREIGN PATENT DOCUMENTS

| | | |
|---|---|---|
| CA | 2232260 | 4/1997 |
| WO | WO 97/11695 | 4/1997 |
| WO | WO 2004/101767 | 11/2004 |
| WO | WO 2007/014198 | 2/2007 |

OTHER PUBLICATIONS

Baker, et al. (document No. 126:305590) retrieved from STN and entered in STN on May 29, 1997.
Cancer [online], [retrieved on Jul. 6, 2007]. Retrieved from the internet, URL http://www.nlm.nih.gov/medlineplus/cancer.html>.
Cancer and Metastasis Reviews (1998), 17(1), 91-106.
Castillo-Pichardo et al., "The Rac Inhibitor EHop-016 Inhibits Mammary Tumor Growth and Metastasis in a Nude Mouse Model," *Transl Oncol.*, 7(5): 546-555 (2014).
Dharmawardhane et al., "Development of EHop-016: A Small Molecule Inhibitor of Rac," The Enzymes, vol. 33, Chap. 6, pp. 117-146, ISSN 1874-6047 (2013).
Golub, "Molecular Classification of Cancer: Class Discovery and Class Prediction by Gene Expression Monitoring," Science (1999), vol. 286, 531-537.
Hernandez et al., "Novel Inhibitors of Rac1 in Metastatic Breast Cancer," *PRHSJ*, 29(4): 348-356 (2010).
Humphries-Bickley et al., "Characterization of a Dual Rac/Cdc42 Inhibitor MBQ-167 in Metastatic Cancer," *Mol. Cancer Ther.*; 16(5): 805-818 (May 2017).
Humphries-Bickley et al., "Pharmacokinetics of Rac inhibitor EHop-016 in mice by ultra-performance liquid chromatography tandem mass spectrometry," *Journal of Chromatography B*, 981-982: 19-26 (2015).
Lav, et al. Document No. 158: 11954, retrieved from STN; enterd in STN on Nov. 6, 2012.
Liu et al., "Biological evaluation of new mimetics of annonaceous acetogenins: Alteration of right scaffold by click linkage with aromatic functionalities," *Euro. J. Med. Chem.*, 78: 248-258 (2014).
Liu, et al. Document No. 160:665402, retrieved from STN; entered in STN on Apr. 28, 2014.
Maldonado et al., "Targeting Rac and Cdc42 GTPases in Cancer," *Cancer Research*, 78(12): 3101-3111 (Jun. 15, 2018).

(Continued)

*Primary Examiner* — Shawquia Jackson

(74) *Attorney, Agent, or Firm* — Barnes & Thornburg LLP; Alice O. Martin

(57) ABSTRACT

Compounds are disclosed that inhibit RhoGTPases that are useful for inhibiting hyperprofilerative and neoplastic diseases. Specifically, the compounds inhibit the GTPases Rac and Cdc42 that are overactive or overexpressed in signaling pathways in cancer and metastasis. Methods for treatment of cancer and hyperproliferative diseases are disclosed.

17 Claims, 16 Drawing Sheets

(4 of 16 Drawing Sheet(s) Filed in Color)

(56) References Cited

OTHER PUBLICATIONS

Martin et al. "Pak and Rac GTPases promote oncogenic KIT-induced neoplasms," *J. of Clin. Invest.,* 123(10): 4449-4463 (2013).
Montalvo-Ortiz et al., "Characterization of EHop-016, Novel Small Molecule Inhibitor of Rac GTPase," *The Journal of Biological Chemistry,* 287(16): 13228-13238 (2012).
Pubchem: Substance Record for SID 239597128, (Feb. 13, 2015), retrieved from the Internet: <https://pubchem.ncbi.nim.nih.gov/substance/239597128#sectio>.
Rivera-Robles et al., "Targeting Cdc42 with the anticancer compound MBQ-167 inhibits cell polarity and growth in the budding yeast *Saccharomyces cerevisiae*," Small GTPases, 1-11 (Jul. 3, 2018).
Surineni, et al. Document No. 162:219217, retrieved from STN; entered in STN on Aug. 18, 2014.
U.S. Appl. No. 15/499,532, filed Apr. 27, 2017.
U.S. Appl. No. 15/970,268, filed May 3, 2018.
U.S. Appl. No. 16/456,641, filed Jun. 28, 2019.

MDA-MB-231

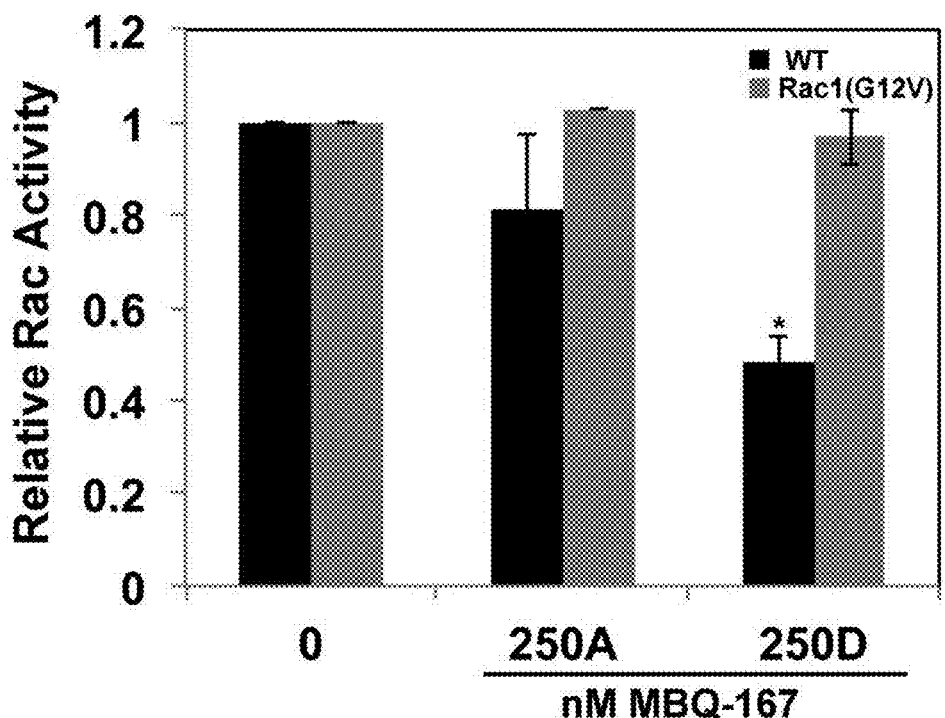
FIG. 7
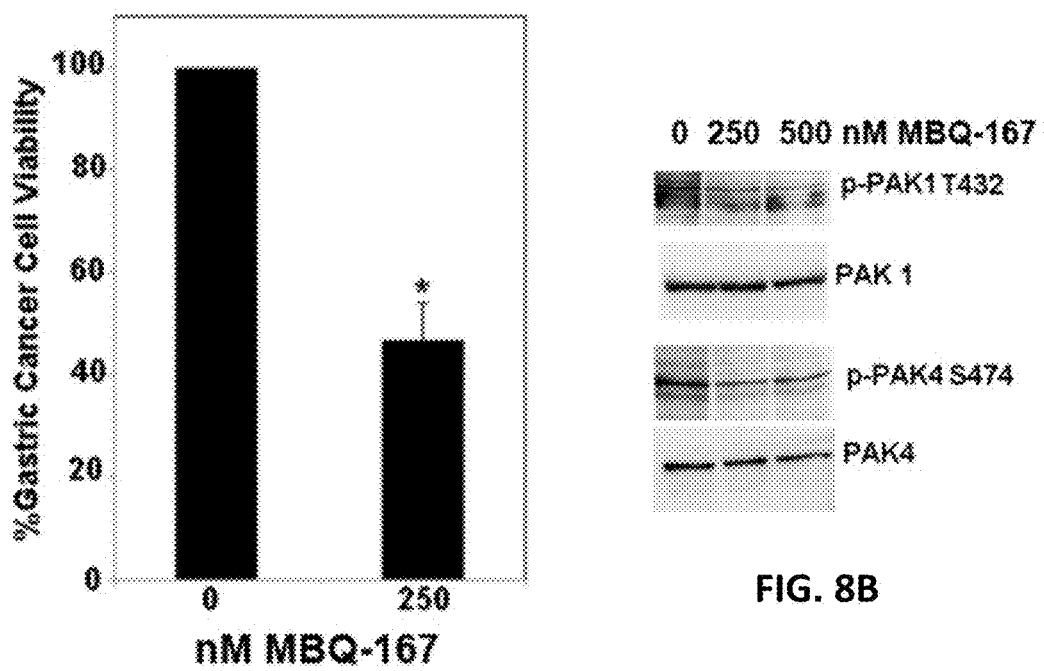
FIG. 8A
FIG. 8B

1,5-DISUBSTITUTED 1,2,3-TRIAZOLES ARE INHIBITORS OF RAC/CDC42 GTPASES

CROSS REFERENCE TO RELATED APPLICATIONS

This application is a Continuation of U.S. patent application Ser. No. 16/456,641, filed Jun. 28, 2019, which is a Continuation of U.S. patent application Ser. No. 15/970,268, filed May 3, 2018 (Now U.S. Pat. No. 10,392,396), which is a Continuation of U.S. patent application Ser. No. 15/499,532, filed Apr. 27, 2017 (Now U.S. Pat. No. 9,981,980), which claims priority from U.S. Ser. No. 62/328,282, filed Apr. 26, 2016. The disclosures set forth in the referenced applications are incorporated herein by reference in their entireties.

This invention was made with Government support under Award Nos. NIH/NIHMD P20GM103475; NIH/NIGMS SC3GM116713; NIH/NIMHD G12MD007600 and NIH/NCI U54 CA096297 awarded by The National Institutes of Health. The U.S. Government has certain rights in the invention.

BACKGROUND

Compounds are disclosed that inhibit Rho GTPases that are useful for inhibiting hyperprofilerative and neoplastic diseases. Specifically, the compounds inhibit the GTPases Rac and Cdc42 that are overactive or overexpressed in signaling pathways in cancer and metastasis. Methods for treatment of cancer and hyperproliferative diseases are disclosed.

The Rho GTPases Rac (Ras-related C3 botulinum toxin substrate) and Cdc42 (cell division control protein 42 homolog) regulate cell functions governing cancer malignancy, including cell polarity, migration, and cell cycle progression. The Rho family of GTPases in humans consists of 20 different members, and aberrant behavior in their regulatory activity has been implicated in cancer and other diseases. More than 70 Guanine nucleotide Exchange Factors (GEFs) are known, which specifically activate one or more of the GTPases. In turn, the activated GTPases can specifically interact with over 60 downstream effectors. Dysregulation of one or more cellular processes can lead to release of malignant cells from their original locations, which subsequently can establish themselves in pre-metastatic niches in, for example, bone or lungs. It has been found that members of the Rho GTPase family, including Rac, Cdc42 and Rho, play key signaling roles in these processes.

Rho GTPases regulate migration and invasion, cytoskeletal organization, transcriptional regulation, cell cycle progression, apoptosis, vesicle trafficking, and cell-to-cell and cell-to-extracellular matrix adhesions. The Rho GTPases Rac and Cdc42 are potent inducers of actin polymerization and extension of actin structures at the leading edge of motile cells. In addition, Cdc42 plays a critical role in cell polarity, and thus, promotes directed and persistent migration.

Studies have implicated hyperactive Rac and Cdc42 with increased cancer cell survival, proliferation, and invasion, as well in Ras and other oncogene-mediated transformation. Furthermore, oncogenic cell surface receptors, such as tyrosine kinase, cytokine, and G protein coupled receptors, activate Rac and Cdc42 via regulation of their upstream effector GEFs. Accordingly, Rac and Cdc42 proteins are generally not mutated in cancer but rather overexpressed or hyperactivated. Even though ~9% of melanomas contain an activating Rac(P29S) mutation, and the hyperactive splice variant Rac1b is overexpressed in some cancers, a majority of the Rac and Cdc42 in human cancer are activated due to upregulated GEFs.

Of the direct downstream effectors of Rac and Cdc42, p21-activated kinases (PAK) are overexpressed in a number of cancers and contribute to cancer transformation and progression by regulating key cellular functions, including cytoskeletal organization, cell migration, adhesion, growth, and development. Therefore, a number of PAK inhibitors have been developed as anti-cancer therapeutics. However, these have been limited by specificity, bioavailability, and toxicity, and have yet to successfully complete clinical trials.

There is a need for new therapeutic agents for the treatment of cancer and other hyperproliferative diseases. The Rac and Cdc42 GTPases are important cellular mediators that are hyperactive or overexpressed in metastatic tumors. Design of novel inhibitors of the activities of Rac and/or Cdc42 with improved activity, pharmacochemical profile and reduced toxicity is desirable.

SUMMARY

A series of novel 1,5-disubstituted 1,2,3-triazoles is disclosed herein. The inventors developed Rac inhibitor EHop-016 ($IC_{50}$, 1,100 nM) that inhibits cancer cell migration and viability, and reduces tumor growth, metastasis, and angiogenesis in vivo. Compound EHop-016 was reported to inhibit Rac1 activity at concentrations <5 µM and with an IC50=1.1 µM in MDA-MB-435 metastatic cells. At higher concentrations (>10 µM) EHop-016 inhibits Rac activity by 100% and Cdc42 activity by 75%. Ehop-016 inhibited in vitro cell migration, and in an in vivo model for metastatic cancer in mice was able to inhibit metastasis and tumor growth.

Some of the members are approximately 10 times more potent inhibitors of Rac and Cdc42 than EHop-016. Treatment of MDA-MB-435 cells with 150 nM of a specific example from this series (MBQ-167) for 24 h resulted in reduced expression of oncogenes and survival inducers c-Myc, Bcl-XL, Bcl-2, with a concomitant increase in the pro-apoptotic protein BAD. Studies from a number of cancer types have shown that Rac/Cdc42/PAK signaling can induce cell survival and evade apoptosis. Therefore, the decreased cell viability and increased apoptosis by MBQ-167, at concentrations that inhibit both Rac and Cdc42, is predicted to be due to dual inhibition of Rac and Cdc42 function.

MBQ-167 inhibits Rac and Cdc42 with $IC_{50}$s of 103 nM and 78 nM respectively, in metastatic breast cancer cells. Consequently, MBQ-167 significantly decreases Rac and Cdc42 downstream effector p21-activated kinase (PAK) signaling and the activity of signal transducer and activator of transcription (STAT3), without affecting Rho, MAPK, or Akt activities. MBQ-167 also inhibits breast cancer cell migration, viability, and mammosphere formation. Moreover, MBQ-167 affects cancer cells that have undergone epithelial to mesenchymal transition by a loss of cell polarity, and inhibition of cell surface actin-based extensions, to ultimately result in detachment from the substratum. Prolonged incubation (120 h) in MBQ-167 decreases metastatic cancer cell viability with a $GI_{50}$ of ~130 nM, without affecting non-cancer mammary epithelial cells. The loss in cancer cell viability is due to MBQ-167-mediated $G_2$/M cell cycle arrest and subsequent apoptosis, especially of the detached cells. In vivo, MBQ-167 inhibits mammary tumor growth and metastasis in immunocompromised mice by ~90%. In conclusion, MBQ-167 is 10× more potent than other currently available Rac/Cdc42 inhibitors, and has potential to be developed as an anticancer drug, as well as a dual inhibitory probe for the study of Rac and Cdc42.

The following numbered embodiments are contemplated and are non-limiting:

1. A compound of the formula (I),

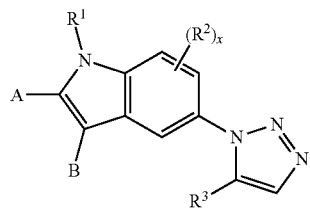

wherein A and B are independently H, deuterium, halogen, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —OH, —CN, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —OR$^4$, —CO$_2$H, —C(O)OC$_1$—C$_6$ alkyl, —C(O)NH$_2$, —C(O)NH($C_1$-$C_6$ alkyl), —C(O)N($C_1$-$C_6$ alkyl)$_2$, —SC$_1$—C$_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl); or A and B taken together with the ring to which they are attached form a $C_5$-$C_8$ cycloalkyl, $C_6$-$C_{10}$ aryl, or a 5- to 8-membered heterocycloalkyl; wherein each hydrogen atom in $C_1$-$C_6$ alkyl, $C_2$-$C_6$ alkenyl, $C_2$-$C_6$ alkynyl, $C_3$-$C_6$ cycloalkyl, $C_5$-$C_8$ cycloalkyl, $C_6$-$C_{10}$ aryl, or 5- to 8-membered heterocycloalkyl is independently optionally substituted by deuterium, halogen, —OH, —CN, —OR$^4$, —OC$_1$—C$_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NHC$_1$—C$_6$ alkyl, —N($C_1$-$C_6$ alkyl)C(O)NH$_2$, —N($C_1$-$C_6$ alkyl)C(O)NHC$_1$—C$_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)OC$_1$—C$_6$ alkyl, —N($C_1$-$C_6$ alkyl)C(O)OC$_1$—C$_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)OC$_1$—C$_6$ alkyl, —C(O)NH$_2$, —C(O)NH($C_1$-$C_6$ alkyl), —C(O)N($C_1$-$C_6$ alkyl)$_2$, —SC$_1$—C$_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, 3- to 7-membered heterocycloalkyl, —CF$_3$, —CHF$_2$, or —CH$_2$F;

R$^1$ is H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl, or —OR$^5$;

each R$^2$ is independently deuterium, halogen, —OH, —CN, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —OR$^6$, —C(O)OR$^6$, —C(O)NR$^6$R$^7$, —NH$_2$, —NH($C_1$-$C_6$ alkyl), —N($C_1$-$C_6$ alkyl)$_2$, —NHC(O)$C_1$-$C_6$ alkyl, —CO$_2$H, —C(O)OC$_1$—C$_6$ alkyl, —C(O)NH$_2$, —C(O)NH($C_1$-$C_6$ alkyl), —C(O)N($C_1$-$C_6$ alkyl)$_2$, —SC$_1$—C$_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl); wherein each hydrogen atom in $C_1$-$C_6$ alkyl, $C_2$-$C_6$ alkenyl, $C_2$-$C_6$ alkynyl, $C_3$-$C_6$ cycloalkyl, and $C_6$-$C_{10}$ aryl is independently optionally substituted by deuterium, halogen, —OH, —CN, —OR$^6$, —OC$_1$—C$_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NHC$_1$—C$_6$ alkyl, —N($C_1$-$C_6$ alkyl)C(O)NH$_2$, —N($C_1$-$C_6$ alkyl)C(O)NHC$_1$—C$_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)OC$_1$—C$_6$ alkyl, —N($C_1$-$C_6$ alkyl)C(O)OC$_1$—C$_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)OC$_1$—C$_6$ alkyl, —C(O)NH$_2$, —C(O)NH($C_1$-$C_6$ alkyl), —C(O)N($C_1$-$C_6$ alkyl)$_2$, —SC$_1$—C$_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, or 3- to 7-membered heterocycloalkyl;

R$^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-(NHR$^8$), $C_1$-$C_6$ alkyl-(OR$^8$), $C_6$-$C_{10}$ aryl-(OR$^8$), $C_1$-$C_6$ alkyl-(NR$^8$R$^9$), or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by deuterium, halogen, —OH, oxo, —OR$^8$, —NHR$^8$, —CN, —OC$_1$—C$_6$ alkyl, —NH$_2$, —NH($C_1$-$C_6$ alkyl), —NH($C_6$-$C_{10}$ aryl), —NH($C_6$-$C_{10}$ aryl)-N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NHC$_1$—C$_6$ alkyl, —N($C_1$-$C_6$ alkyl)C(O)NH$_2$, —N($C_1$-$C_6$ alkyl)C(O)NHC$_1$—C$_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)OC$_1$—C$_6$ alkyl, —N($C_1$-$C_6$ alkyl)C(O)OC$_1$—C$_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)OC$_1$—C$_6$ alkyl, —C(O)NH$_2$, —C(O)NH($C_1$-

$C_6$ alkyl), —C(O)N($C_1$-$C_6$ alkyl)$_2$, —S$C_1$—$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_1$-$C_6$ alkyl-(3- to 7-membered heterocycloalkyl), —CF$_3$, —CHF$_2$, or —CH$_2$F;

each $R^4$, $R^5$, $R^6$, $R^7$, $R^8$, and $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_1$-$C_6$ alkyl-(3- to 7-membered heterocycloalkyl), heteroaryl, —S(O)$_2$$C_1$-$C_6$ alkyl, —CF$_3$, —CHF$_2$, or —CH$_2$F, wherein each hydrogen in $C_6$-$C_{10}$ aryl is optionally substituted by $C_3$-$C_6$ cycloalkyl, 3- to 7-membered heterocycloalkyl, or —CH$_2$CN; and x is 0, 1, 2, or 3;

or a pharmaceutically acceptable salt thereof.

2. The compound of clause 1, wherein A and B taken together with the ring to which they are attached form a $C_5$-$C_8$ cycloalkyl, $C_6$-$C_{10}$ aryl, or a 5- to 8-membered heterocycloalkyl, wherein each hydrogen atom in $C_5$-$C_8$ cycloalkyl, $C_6$-$C_{10}$ aryl, or a 5- to 8-membered heterocycloalkyl is independently optionally substituted by deuterium, halogen, —OH, —CN, —OR$^4$, —O$C_1$—$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$—$C_6$ alkyl, —N($C_1$-$C_6$ alkyl)C(O)NH$_2$, —N($C_1$-$C_6$ alkyl)C(O)NH$C_1$—$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$—$C_6$ alkyl, —N($C_1$-$C_6$ alkyl)C(O)O$C_1$—$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$—$C_6$ alkyl, —C(O)NH$_2$, —C(O)NH($C_1$-$C_6$ alkyl), —C(O)N($C_1$-$C_6$ alkyl)$_2$, —S$C_1$—$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, 3- to 7-membered heterocycloalkyl, —CF$_3$, —CHF$_2$, or —CH$_2$F, or a pharmaceutically acceptable salt thereof.

3. The compound of clause 1 or clause 2, wherein A and B taken together with the ring to which they are attached form a $C_6$-$C_{10}$ aryl, wherein each hydrogen atom in $C_6$-$C_{10}$aryl is independently optionally substituted by deuterium, halogen, —OH, —CN, —OR$^4$, —O$C_1$—$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$—$C_6$ alkyl, —N($C_1$-$C_6$ alkyl)C(O)NH$_2$, —N($C_1$-$C_6$ alkyl)C(O)NH$C_1$—$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$—$C_6$ alkyl, —N($C_1$-$C_6$ alkyl)C(O)O$C_1$—$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$—$C_6$ alkyl, —C(O)NH$_2$, —C(O)NH($C_1$-$C_6$ alkyl), —C(O)N($C_1$-$C_6$ alkyl)$_2$, —S$C_1$—$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, 3- to 7-membered heterocycloalkyl, —CF$_3$, —CHF$_2$, or —CH$_2$F, or a pharmaceutically acceptable salt thereof.

4. The compound of any one of clauses 1-3, wherein $R^1$ is H, $C_1$-$C_6$ alkyl, $C_2$-$C_6$ alkenyl, $C_2$-$C_6$ alkynyl, $C_3$-$C_6$ cycloalkyl, or 3- to 7-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, or 3- to 7-membered heterocycloalkyl is independently optionally substituted by deuterium, halogen, $C_1$-$C_6$ alkyl, $C_1$-$C_6$ haloalkyl, or —OR$^5$, or a pharmaceutically acceptable salt thereof.

5. The compound of any one of clauses 1-4, wherein $R^1$ is H, $C_1$-$C_6$ alkyl, $C_3$-$C_6$ cycloalkyl, or 3- to 7-membered heterocycloalkyl, wherein each hydrogen atom in $C_1$-$C_6$ alkyl, $C_3$-$C_6$ cycloalkyl, or 3- to 7-membered heterocycloalkyl is independently optionally substituted by deuterium, halogen, $C_1$-$C_6$ alkyl, $C_1$-$C_6$ haloalkyl, or —OR$^5$, or a pharmaceutically acceptable salt thereof.

6. The compound of any one of clauses 1-5, wherein $R^1$ is H or $C_1$-$C_6$ alkyl, wherein each hydrogen atom in $C_1$-$C_6$ alkyl is independently optionally substituted by deuterium, halogen, $C_1$-$C_6$ alkyl, $C_1$-$C_6$ haloalkyl, or —OR$^5$.

7. The compound of any one of clauses 1-6, wherein x is 0, or a pharmaceutically acceptable salt thereof.

8. The compound of any one of clauses 1-6, wherein x is 1, 2, or 3, or a pharmaceutically acceptable salt thereof.

9. The compound of any one of clauses 1-8, wherein $R^3$ is $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-(NHR$^8$), $C_1$-$C_6$ alkyl-(OR$^8$), $C_6$-$C_{10}$ aryl-(OR$^8$), $C_1$-$C_6$ alkyl-(NR$^8$R$^9$), or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by deuterium, halogen, —OH, oxo, —OR$^8$, —NHR$^8$, —CN, —O$C_1$—$C_6$ alkyl, —NH$_2$, —NH($C_1$-$C_6$ alkyl), —NH($C_6$-$C_{10}$ aryl), —NH($C_6$-$C_{10}$ aryl)-N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$—$C_6$ alkyl, —N($C_1$-$C_6$ alkyl)C(O)NH$_2$, —N($C_1$-$C_6$ alkyl)C(O)NH$C_1$—$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$—$C_6$ alkyl, —N($C_1$-$C_6$ alkyl)C(O)O$C_1$—$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$—$C_6$ alkyl, —C(O)NH$_2$, —C(O)NH($C_1$-$C_6$ alkyl), —C(O)N($C_1$-$C_6$ alkyl)$_2$, —S$C_1$—$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_1$-$C_6$ alkyl, $C_2$-$C_6$ alkenyl, $C_2$-$C_6$ alkynyl, —$C_3$-$C_6$ cycloalkyl, 3- to 7-membered heterocycloalkyl, $C_1$-$C_6$ alkyl-(3- to 7-membered heterocycloalkyl), —CF$_3$, —CHF$_2$, or —CH$_2$F, or a pharmaceutically acceptable salt thereof.

10. The compound of any one of clauses 1-9, wherein $R^3$ is $C_1$-$C_6$ alkyl, $C_2$-$C_6$ alkenyl, $C_6$-$C_{10}$ aryl, $C_1$-$C_6$ alkyl- (OR⁸), $C_6$-$C_{10}$ aryl-(OR⁸), or monocyclic heteroaryl; wherein each hydrogen atom in $C_1$-$C_6$ alkyl, $C_2$-$C_6$ alkenyl, $C_6$-$C_{10}$ aryl, or monocyclic heteroaryl is optionally substituted by deuterium, halogen, —OH, oxo, —OR⁸, —NHR⁸, —CN, —OC₁—C₆ alkyl, —NH₂, —NH($C_1$-$C_6$ alkyl), —NH($C_6$-$C_{10}$ aryl), —NH($C_6$-$C_{10}$ aryl)-N($C_1$-$C_6$ alkyl)₂, —NHC(O)$C_1$-$C_6$ alkyl, —N($C_1$-$C_6$ alkyl)C(O)$C_1$-$C_6$ alkyl, —NHC(O)NH₂, —NHC(O)NHC₁—C₆ alkyl, —N($C_1$-$C_6$ alkyl)C(O)NH₂, —N($C_1$-$C_6$ alkyl)C(O)NHC₁—C₆ alkyl, —NHC(O)N($C_1$-$C_6$ alkyl)₂, —N($C_1$-$C_6$ alkyl)C(O)N($C_1$-$C_6$ alkyl)₂, —NHC(O)OC₁—C₆ alkyl, —N($C_1$-$C_6$ alkyl)C(O)OC₁—C₆ alkyl, —NHS(O)($C_1$-$C_6$ alkyl), —NHS(O)₂($C_1$-$C_6$ alkyl), —N($C_1$-$C_6$ alkyl)S(O)($C_1$-$C_6$ alkyl), —N($C_1$-$C_6$ alkyl)S(O)₂($C_1$-$C_6$ alkyl), —NHS(O)NH₂, —NHS(O)₂NH₂, —N($C_1$-$C_6$ alkyl)S(O)NH₂, —N($C_1$-$C_6$ alkyl)S(O)₂NH₂, —NHS(O)NH($C_1$-$C_6$ alkyl), —NHS(O)₂NH($C_1$-$C_6$ alkyl), —NHS(O)N($C_1$-$C_6$ alkyl)₂, —NHS(O)₂N($C_1$-$C_6$ alkyl)₂, —N($C_1$-$C_6$ alkyl)S(O)NH($C_1$-$C_6$ alkyl), —N($C_1$-$C_6$ alkyl)S(O)₂NH($C_1$-$C_6$ alkyl), —N($C_1$-$C_6$ alkyl)S(O)N($C_1$-$C_6$ alkyl)₂, —N($C_1$-$C_6$ alkyl)S(O)₂N($C_1$-$C_6$ alkyl)₂, —CO₂H, —C(O)OC₁—C₆ alkyl, —C(O)NH₂, —C(O)NH($C_1$-$C_6$ alkyl), —C(O)N($C_1$-$C_6$ alkyl)₂, —SC₁—C₆ alkyl, —S(O)$C_1$-$C_6$ alkyl, —S(O)₂$C_1$-$C_6$ alkyl, —S(O)NH($C_1$-$C_6$ alkyl), —S(O)₂NH($C_1$-$C_6$ alkyl), —S(O)N($C_1$-$C_6$ alkyl)₂, —S(O)₂N($C_1$-$C_6$ alkyl)₂, —P($C_1$-$C_6$ alkyl)₂, —P(O)($C_1$-$C_6$ alkyl)₂, $C_1$-$C_6$ alkyl, $C_2$-$C_6$ alkenyl, $C_2$-$C_6$ alkynyl, —$C_3$-$C_6$ cycloalkyl, 3- to 7-membered heterocycloalkyl, $C_1$-$C_6$ alkyl-(3- to 7-membered heterocycloalkyl), —CF₃, —CHF₂, or —CH₂F, or a pharmaceutically acceptable salt thereof.

11. The compound of any one of clauses 1-9, wherein R³ is $C_1$-$C_6$ alkyl, $C_2$-$C_6$ alkenyl, $C_6$-$C_{10}$ aryl, $C_1$-$C_6$ alkyl-(OR⁸), $C_6$-$C_{10}$ aryl-(OR⁸), or monocyclic heteroaryl; wherein each hydrogen atom in $C_1$-$C_6$ alkyl, $C_2$-$C_6$ alkenyl, $C_6$-$C_{10}$ aryl, or monocyclic heteroaryl is optionally substituted by deuterium, halogen, —OH, —OR⁸, —OC₁—C₆ alkyl, $C_1$-$C_6$ alkyl, or 3- to 7-membered heterocycloalkyl, or a pharmaceutically acceptable salt thereof.

12. The compound of clause 1, wherein the compound is selected from the group consisting of

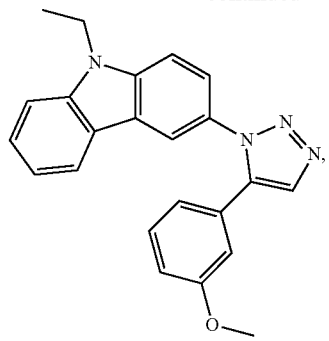

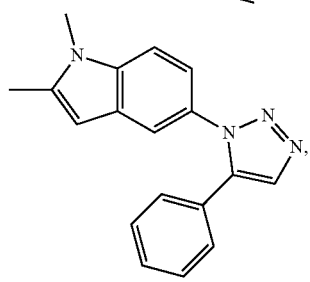

-continued

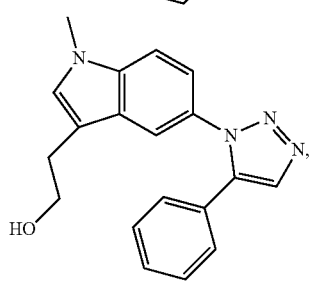

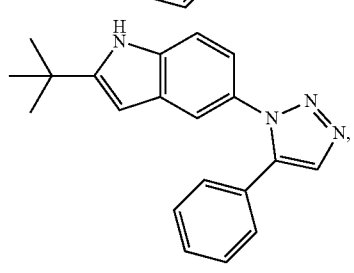

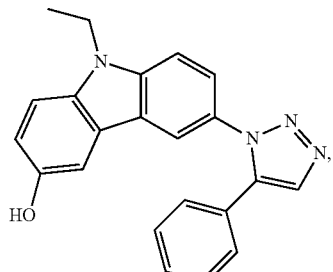

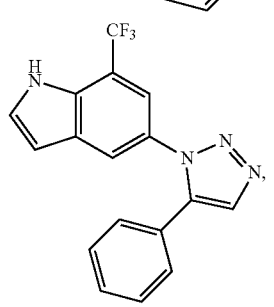

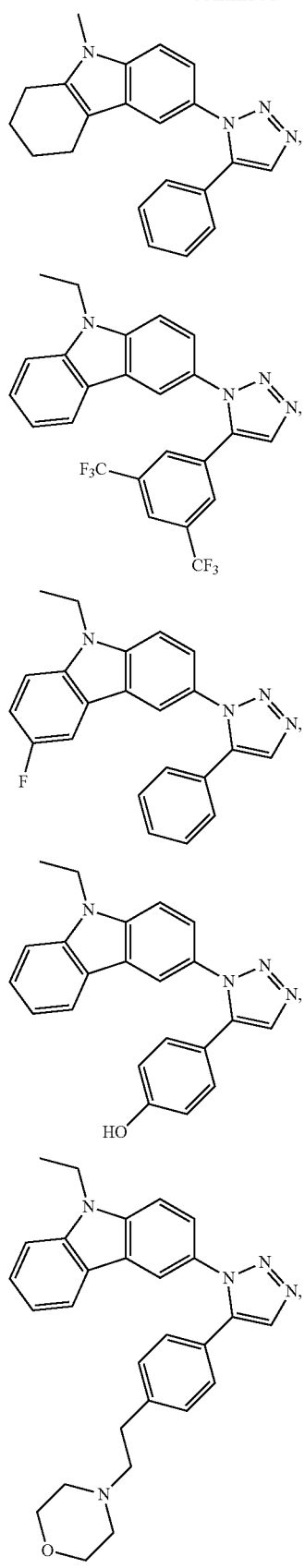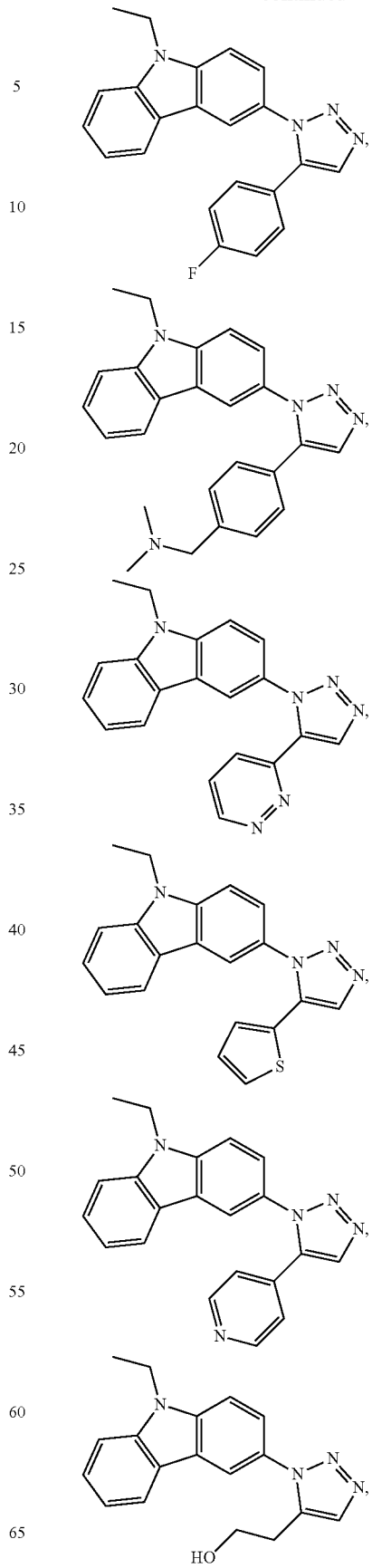

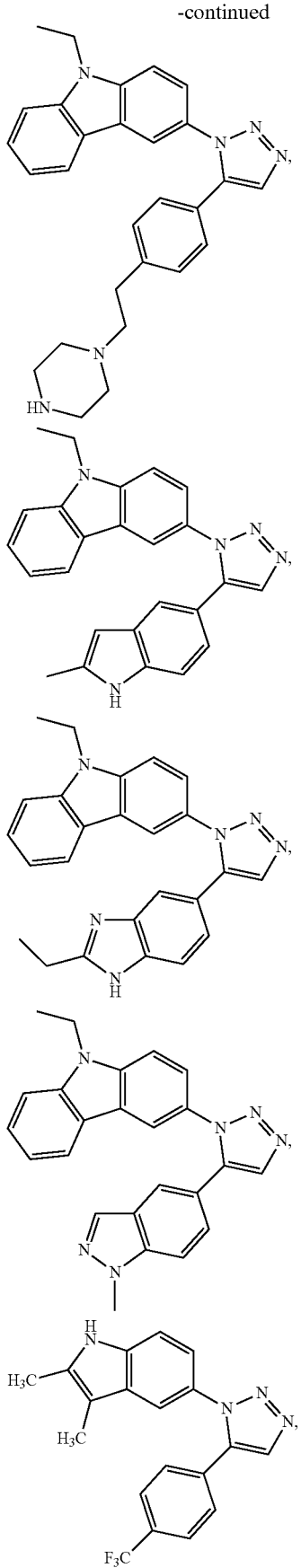
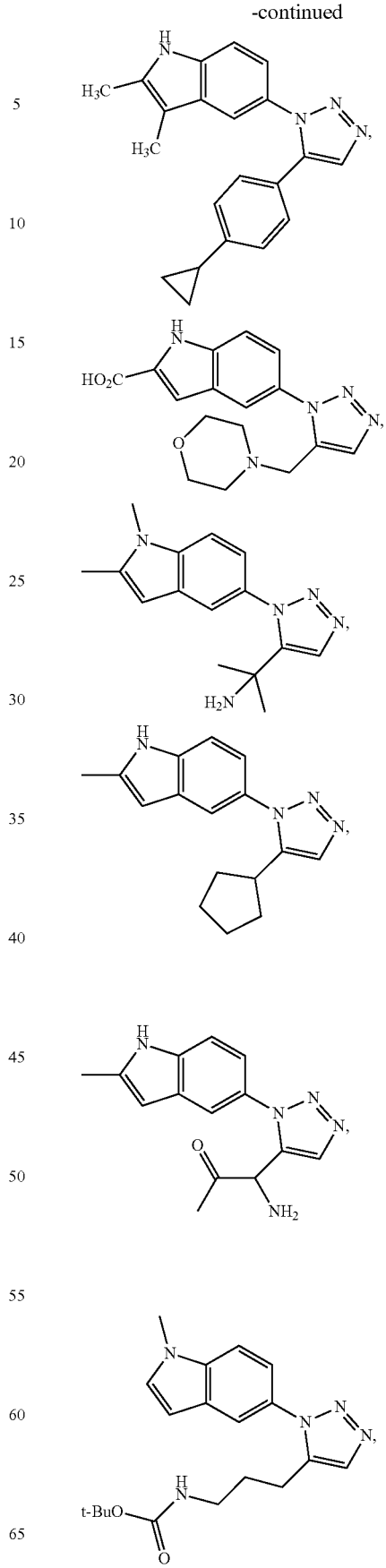

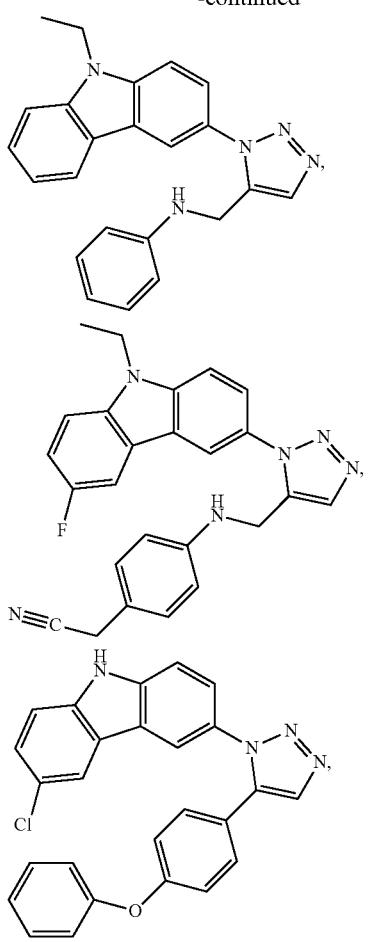
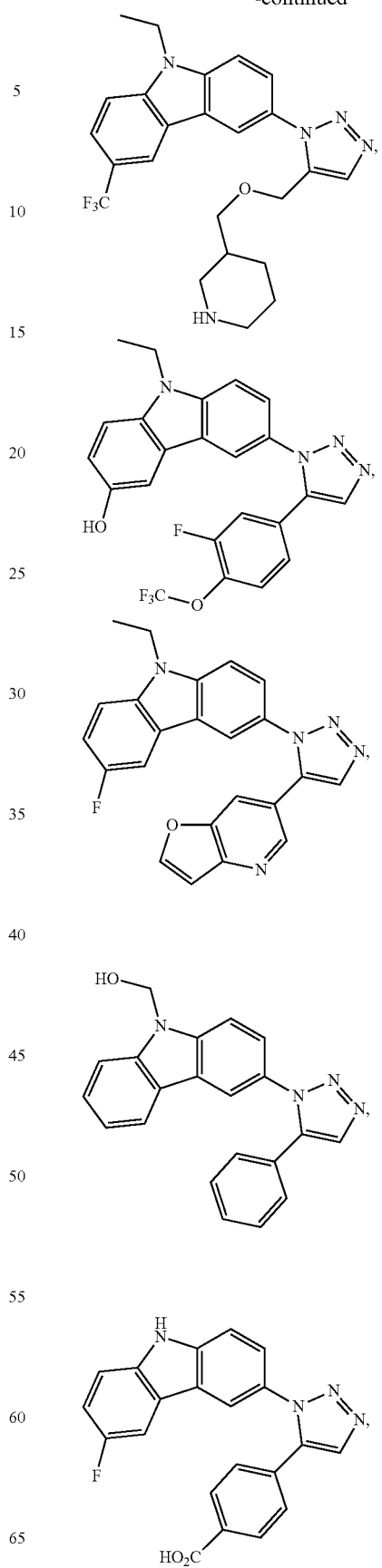

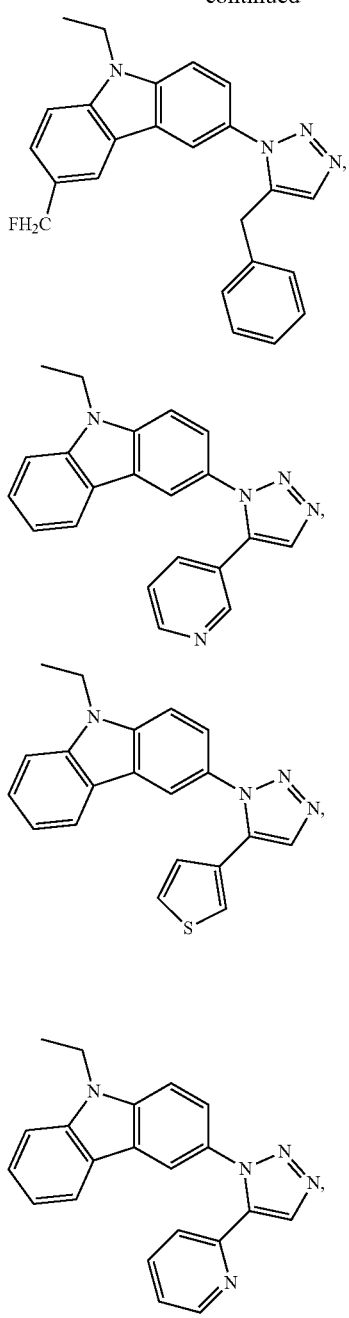
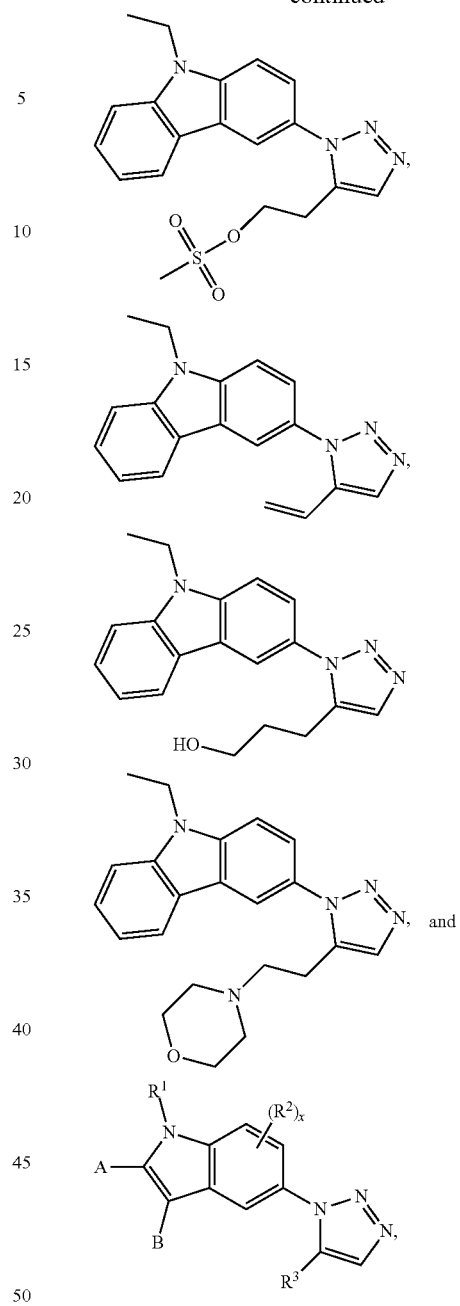
or a pharmaceutically acceptable salt thereof.
13. The compound of clause 1 or clause 12, wherein the compound is selected from the group consisting of
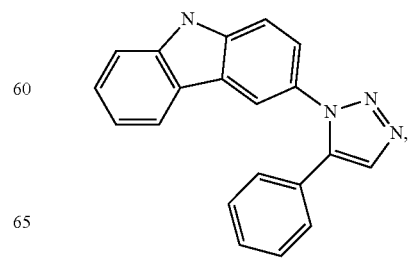

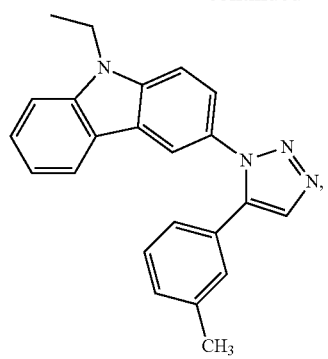
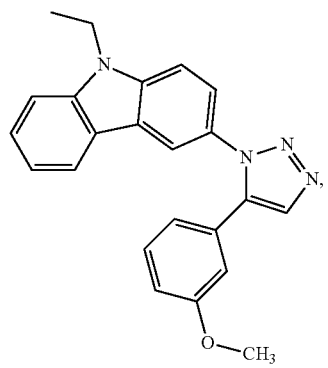
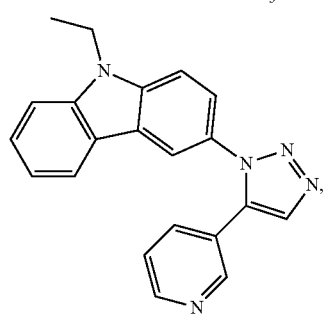
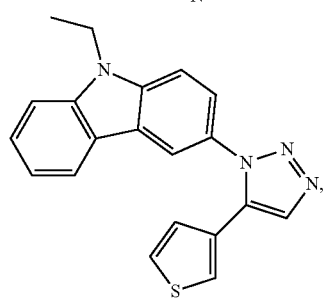
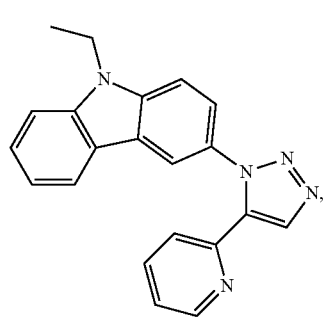
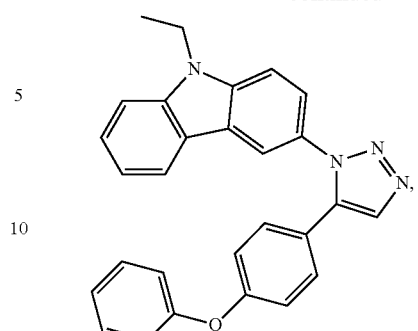
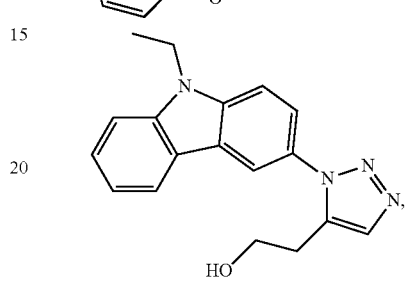
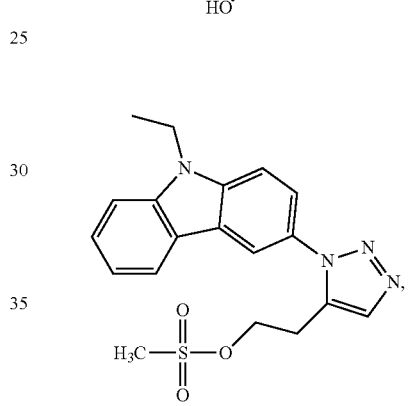
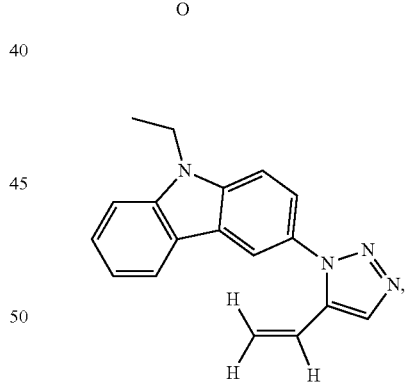
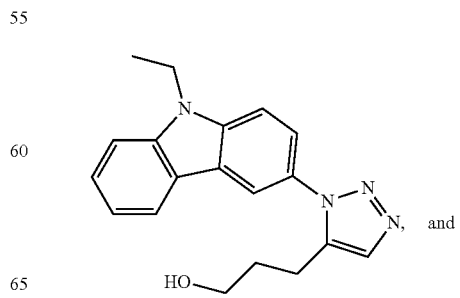

-continued

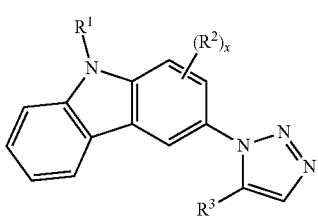

or a pharmaceutically acceptable salt thereof.

14. The compound of clause 1, wherein the compound has the formula (II), (II)

wherein $R^1$ is H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl, or —$OR^5$;

each $R^2$ is independently deuterium, halogen, —OH, —CN, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —$OR^6$, —C(O)$OR^6$, —C(O)$NR^6R^7$, —$NH_2$, —NH($C_1$-$C_6$ alkyl), —N($C_1$-$C_6$ alkyl)$_2$, —NHC(O)$C_1$-$C_6$ alkyl, —$CO_2H$, —C(O)$OC_1$—$C_6$ alkyl, —C(O)$NH_2$, —C(O)NH($C_1$-$C_6$ alkyl), —C(O)N($C_1$-$C_6$ alkyl)$_2$, —$SC_1$—$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl); wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OR^6$, —$OC_1$—$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)$NHC_1$—$C_6$ alkyl, —N($C_1$-$C_6$ alkyl)C(O)$NH_2$, —N($C_1$-$C_6$ alkyl)C(O)$NHC_1$—$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$—$C_6$ alkyl, —N($C_1$-$C_6$ alkyl)C(O)$OC_1$—$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$—$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2H$, —C(O)$OC_1$—$C_6$ alkyl, —C(O)$NH_2$, —C(O)NH($C_1$-$C_6$ alkyl), —C(O)N($C_1$-$C_6$ alkyl)$_2$, —$SC_1$—$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, or 3- to 7-membered heterocycloalkyl;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-($NHR^8$), $C_1$-$C_6$ alkyl-($OR^8$), $C_6$-$C_{10}$ aryl-($OR^8$), $C_1$-$C_6$ alkyl-($NR^8R^9$), or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by deuterium, halogen, —OH, oxo, —$OR^8$, —$NHR^8$, —CN, —$OC_1$—$C_6$ alkyl, —$NH_2$, —NH($C_1$-$C_6$ alkyl), —NH($C_6$-$C_{10}$ aryl), —NH($C_6$-$C_{10}$ aryl)-N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)$NHC_1$—$C_6$ alkyl, —N($C_1$-$C_6$ alkyl)C(O)$NH_2$, —N($C_1$-$C_6$ alkyl)C(O)$NHC_1$—$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$—$C_6$ alkyl, —N($C_1$-$C_6$ alkyl)C(O)$OC_1$—$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2NH_2$, —N($C_1$-$C_6$ alkyl)S(O)$NH_2$, —N($C_1$-$C_6$ alkyl)S(O)$_2NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2H$, —C(O)$OC_1$—$C_6$ alkyl, —C(O)$NH_2$, —C(O)NH($C_1$-$C_6$ alkyl), —C(O)N($C_1$-$C_6$ alkyl)$_2$, —$SC_1$—$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_1$-$C_6$ alkyl, $C_2$-$C_6$ alkenyl, $C_2$-$C_6$ alkynyl, —$C_3$-$C_6$ cycloalkyl, 3- to 7-membered heterocycloalkyl, $C_1$-$C_6$ alkyl-(3- to 7-membered heterocycloalkyl), —$CF_3$, —$CHF_2$, or —$CH_2F$;

each $R^5$, $R^6$, $R^7$, $R^8$, and $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_1$-$C_6$ alkyl-(3- to 7-membered heterocycloalkyl), heteroaryl, —S(O)$_2C_1$-$C_6$ alkyl, —$CF_3$, —$CHF_2$, or —$CH_2F$, wherein each hydrogen in $C_6$-$C_{10}$ aryl is optionally substituted by $C_3$-$C_6$ cycloalkyl, 3- to 7-membered heterocycloalkyl, or —$CH_2CN$; and x is 0, 1, 2, or 3;

or a pharmaceutically acceptable salt thereof. The compound of clause of 1 or clause 14, wherein $R^1$ is H, C1-C6 alkyl, C2-C6 alkenyl, C2-C6 alkynyl, C3-C6 cycloalkyl, or 3- to 7-membered heterocycloalkyl, wherein each hydrogen atom in C1-C6 alkyl, C2-C6 alkenyl, C2-C6 alkynyl, C3-C6 cycloalkyl, or 3- to 7-membered heterocycloalkyl is independently optionally substituted by deuterium, halogen, C1-C6 alkyl, C1-C6 haloalkyl, or —OR5, or a pharmaceutically acceptable salt thereof.

15. The compound of clause of 1 or clause 14, wherein $R^1$ is H, $C_1$-$C_6$ alkyl, $C_2$-$C_6$ alkenyl, $C_2$-$C_6$ alkynyl, $C_3$-$C_6$ cycloalkyl, or 3- to 7-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, or 3- to 7-membered heterocycloalkyl is independently optionally substituted by deuterium, halogen, $C_1$-$C_6$ alkyl, $C_1$-$C_6$ haloalkyl, or —$OR^5$, or a pharmaceutically acceptable salt thereof.

16. The compound of any one of clauses 1, clause 14, or clause 15, wherein $R^1$ is H, $C_1$-$C_6$ alkyl, $C_3$-$C_6$ cycloalkyl, or 3- to 7-membered heterocycloalkyl, wherein each hydrogen atom in $C_1$-$C_6$ alkyl, $C_3$-$C_6$ cycloalkyl, or 3- to 7-membered heterocycloalkyl is independently optionally substituted by deuterium, halogen, $C_1$-$C_6$ alkyl, $C_1$-$C_6$ haloalkyl, or —$OR^5$, or a pharmaceutically acceptable salt thereof.

17. The compound of any one of clauses 1 or clauses 14-16, wherein $R^1$ is H or $C_1$-$C_6$ alkyl, wherein each hydrogen atom in $C_1$-$C_6$ alkyl is independently optionally substituted by deuterium, halogen, $C_1$-$C_6$ alkyl, $C_1$-$C_6$ haloalkyl, or —$OR^5$, or a pharmaceutically acceptable salt thereof.

18. The compound of any one of clauses 1 or clauses 14-17, wherein x is 0, or a pharmaceutically acceptable salt thereof.

19. The compound of any one of clauses 1 or clauses 14-17, wherein x is 1, 2, or 3, or a pharmaceutically acceptable salt thereof.

20. The compound of any one of clauses 1 or clause 14-19, wherein $R^3$ is $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-($NHR^8$), $C_1$-$C_6$ alkyl-($OR^8$), $C_6$-$C_{10}$ aryl-($OR^8$), $C_1$-$C_6$ alkyl-($NR^8R^9$), or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by deuterium, halogen, —OH, oxo, —$OR^8$, —$NHR^8$, —CN, —$OC_1$—$C_6$ alkyl, —$NH_2$, —$NH(C_1$-$C_6$ alkyl), —$NH(C_6$-$C_{10}$ aryl), —$NH(C_6$-$C_{10}$ aryl)-$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$—$C_6$ alkyl, —$N(C_1$-$C_6$ alkyl)$C(O)NH_2$, —$N(C_1$-$C_6$ alkyl)$C(O)NHC_1$—$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$—$C_6$ alkyl, —$N(C_1$-$C_6$ alkyl)$C(O)OC_1$—$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$—$C_6$ alkyl, —$C(O)NH_2$, —$C(O)NH(C_1$-$C_6$ alkyl), —$C(O)N(C_1$-$C_6$ alkyl)$_2$, —$SC_1$—$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, $C_1$-$C_6$ alkyl, $C_2$-$C_6$ alkenyl, $C_2$-$C_6$ alkynyl, —$C_3$-$C_6$ cycloalkyl, 3- to 7-membered heterocycloalkyl, $C_1$-$C_6$ alkyl-(3- to 7-membered heterocycloalkyl), —$CF_3$, —$CHF_2$, or —$CH_2F$, or a pharmaceutically acceptable salt thereof.

21. The compound of any one of clauses 1 or clauses 14-20, wherein $R^3$ is $C_1$-$C_6$ alkyl, $C_2$-$C_6$ alkenyl, $C_6$-$C_{10}$ aryl, $C_1$-$C_6$ alkyl-($OR^8$), $C_6$-$C_{10}$ aryl-($OR^8$), or monocyclic heteroaryl; wherein each hydrogen atom in $C_1$-$C_6$ alkyl, $C_2$-$C_6$ alkenyl, $C_6$-$C_{10}$ aryl, or monocyclic heteroaryl is optionally substituted by deuterium, halogen, —OH, oxo, —$OR^8$, —$NHR^8$, —CN, —$OC_1$—$C_6$ alkyl, —$NH_2$, —NH($C_1$-$C_6$ alkyl), —$NH(C_6$-$C_{10}$ aryl), —$NH(C_6$-$C_{10}$ aryl)-$N(C_1$-$C_6$ alkyl)$_2$, —$NHC(O)C_1$-$C_6$ alkyl, —$N(C_1$-$C_6$ alkyl)$C(O)C_1$-$C_6$ alkyl, —$NHC(O)NH_2$, —$NHC(O)NHC_1$—$C_6$ alkyl, —$N(C_1$-$C_6$ alkyl)$C(O)NH_2$, —$N(C_1$-$C_6$ alkyl)$C(O)NHC_1$—$C_6$ alkyl, —$NHC(O)N(C_1$-$C_6$ alkyl)$_2$, —$N(C_1$-$C_6$ alkyl)$C(O)N(C_1$-$C_6$ alkyl)$_2$, —$NHC(O)OC_1$—$C_6$ alkyl, —$N(C_1$-$C_6$ alkyl)$C(O)OC_1$—$C_6$ alkyl, —$NHS(O)(C_1$-$C_6$ alkyl), —$NHS(O)_2(C_1$-$C_6$ alkyl), —$N(C_1$-$C_6$ alkyl)$S(O)(C_1$-$C_6$ alkyl), —$N(C_1$-$C_6$ alkyl)$S(O)_2(C_1$-$C_6$ alkyl), —$NHS(O)NH_2$, —$NHS(O)_2NH_2$, —$N(C_1$-$C_6$ alkyl)$S(O)NH_2$, —$N(C_1$-$C_6$ alkyl)$S(O)_2NH_2$, —$NHS(O)NH(C_1$-$C_6$ alkyl), —$NHS(O)_2NH(C_1$-$C_6$ alkyl), —$NHS(O)N(C_1$-$C_6$ alkyl)$_2$, —$NHS(O)_2N(C_1$-$C_6$ alkyl)$_2$, —$N(C_1$-$C_6$ alkyl)$S(O)NH(C_1$-$C_6$ alkyl), —$N(C_1$-$C_6$ alkyl)$S(O)_2NH(C_1$-$C_6$ alkyl), —$N(C_1$-$C_6$ alkyl)$S(O)N(C_1$-$C_6$ alkyl)$_2$, —$N(C_1$-$C_6$ alkyl)$S(O)_2N(C_1$-$C_6$ alkyl)$_2$, —$CO_2H$, —$C(O)OC_1$—$C_6$ alkyl, —$C(O)NH_2$, —$C(O)NH(C_1$-$C_6$ alkyl), —$C(O)N(C_1$-$C_6$ alkyl)$_2$, —$SC_1$—$C_6$ alkyl, —$S(O)C_1$-$C_6$ alkyl, —$S(O)_2C_1$-$C_6$ alkyl, —$S(O)NH(C_1$-$C_6$ alkyl), —$S(O)_2NH(C_1$-$C_6$ alkyl), —$S(O)N(C_1$-$C_6$ alkyl)$_2$, —$S(O)_2N(C_1$-$C_6$ alkyl)$_2$, —$P(C_1$-$C_6$ alkyl)$_2$, —$P(O)(C_1$-$C_6$ alkyl)$_2$, $C_1$-$C_6$ alkyl, $C_2$-$C_6$ alkenyl, $C_2$-$C_6$ alkynyl, —$C_3$-$C_6$ cycloalkyl, 3- to 7-membered heterocycloalkyl, $C_1$-$C_6$ alkyl-(3- to 7-membered heterocycloalkyl), —$CF_3$, —$CHF_2$, or —$CH_2F$, or a pharmaceutically acceptable salt thereof.

22. The compound of any one of clauses 1 or clauses 14-21, wherein $R^3$ is $C_1$-$C_6$ alkyl, $C_2$-$C_6$ alkenyl, $C_6$-$C_{10}$ aryl, $C_1$-$C_6$ alkyl-($OR^8$), $C_6$-$C_{10}$ aryl-($OR^8$), or monocyclic heteroaryl; wherein each hydrogen atom in $C_1$-$C_6$ alkyl, $C_2$-$C_6$ alkenyl, $C_6$-$C_{10}$ aryl, or monocyclic heteroaryl is optionally substituted by deuterium, halogen, —OH, —$OR^8$, —$OC_1$—$C_6$ alkyl, $C_1$-$C_6$ alkyl, or 3- to 7-membered heterocycloalkyl, or a pharmaceutically acceptable salt thereof.

23. The compound of clause 1, wherein the compound has the formula (III),

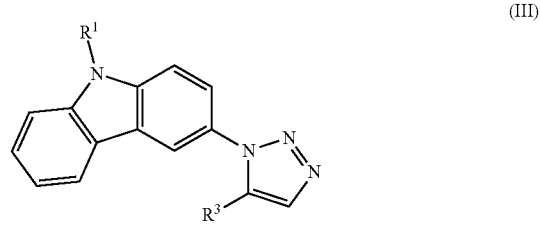

(III)

wherein $R^1$ is H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl, or —$OR^5$;

$R^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-($NHR^8$), $C_1$-$C_6$ alkyl-($OR^8$), $C_6$-$C_{10}$ aryl-($OR^8$), $C_1$-$C_6$ alkyl-($NR^8R^9$), or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by deuterium, halogen, —OH, oxo, —$OR^8$, —$NHR^8$, —CN, —$OC_1$—$C_6$ alkyl, —$NH_2$, —$NH(C_1$-$C_6$ alkyl), —$NH(C_6$-$C_{10}$ aryl), —$NH(C_6$-$C_{10}$ aryl)-N ($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$—$C_6$ alkyl, —N($C_1$-$C_6$ alkyl)C(O)NH$_2$, —N($C_1$-$C_6$ alkyl)C(O)NH$C_1$—$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$—$C_6$ alkyl, —N($C_1$-$C_6$ alkyl)C(O)O$C_1$—$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$—$C_6$ alkyl, —C(O)NH$_2$, —C(O)NH($C_1$-$C_6$ alkyl), —C(O)N($C_1$-$C_6$ alkyl)$_2$, —S$C_1$—$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_1$-$C_6$ alkyl, $C_2$-$C_6$ alkenyl, $C_2$-$C_6$ alkynyl, —$C_3$-$C_6$ cycloalkyl, 3- to 7-membered heterocycloalkyl, $C_1$-$C_6$ alkyl-(3- to 7-membered heterocycloalkyl), —CF$_3$, —CHF$_2$, or —CH$_2$F; and each $R^5$, $R^6$, $R^7$, $R^8$, and $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_1$-$C_6$ alkyl-3- to 7-membered heterocycloalkyl, heteroaryl, —S(O)$_2$$C_1$-$C_6$ alkyl, —CF$_3$, —CHF$_2$, or —CH$_2$F, wherein each hydrogen in $C_6$-$C_{10}$ aryl is optionally substituted by $C_3$-$C_6$ cycloalkyl, 3- to 7-membered heterocycloalkyl, or —CH$_2$CN; or a pharmaceutically acceptable salt thereof.

24. The compound of clause 1 or clause 23, wherein $R^1$ is H, $C_1$-$C_6$ alkyl, $C_2$-$C_6$ alkenyl, $C_2$-$C_6$ alkynyl, $C_3$-$C_6$ cycloalkyl, or 3- to 7-membered heterocycloalkyl, wherein each hydrogen atom in $C_1$-$C_6$ alkyl, $C_2$-$C_6$ alkenyl, $C_2$-$C_6$ alkynyl, $C_3$-$C_6$ cycloalkyl, or 3- to 7-membered heterocycloalkyl is independently optionally substituted by deuterium, halogen, $C_1$-$C_6$ alkyl, $C_1$-$C_6$ haloalkyl, or —OR$_5$, or a pharmaceutically acceptable salt thereof.

25. The compound of clause 1, clause 23, or clause 24, wherein $R^1$ is H, $C_1$-$C_6$ alkyl, $C_3$-$C_6$ cycloalkyl, or 3- to 7-membered heterocycloalkyl, wherein each hydrogen atom in $C_1$-$C_6$alkyl, $C_3$-$C_6$ cycloalkyl, or 3- to 7-membered heterocycloalkyl is independently optionally substituted by deuterium, halogen, $C_1$-$C_6$ alkyl, $C_1$-$C_6$ haloalkyl, or —OR$^5$, or a pharmaceutically acceptable salt thereof.

26. The compound of any one of clauses 1 or clauses 23-25, wherein $R^1$ is H or $C_1$-$C_6$ alkyl, wherein each hydrogen atom in $C_1$-$C_6$ alkyl is independently optionally substituted by deuterium, halogen, $C_1$-$C_6$ alkyl, $C_1$-$C_6$haloalkyl, or —OR$^5$, or a pharmaceutically acceptable salt thereof.

27. The compound of any one of clauses 1 or clauses 23-26, wherein $R^3$ $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-(NHR$^8$), $C_1$-$C_6$ alkyl-(OR$^8$), $C_6$-$C_{10}$ aryl-(OR$^8$), $C_1$-$C_6$ alkyl-(NR$^8$R$^9$), or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by deuterium, halogen, —OH, oxo, —OR$^8$, —NHR$^8$, —CN, —O$C_1$—$C_6$ alkyl, —NH$_2$, —NH($C_1$-$C_6$ alkyl), —NH($C_6$-$C_{10}$ aryl), —NH($C_6$-$C_{10}$ aryl)-N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$—$C_6$ alkyl, —N($C_1$-$C_6$ alkyl)C(O)NH$_2$, —N($C_1$-$C_6$ alkyl)C(O)NH$C_1$—$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$—$C_6$ alkyl, —N($C_1$-$C_6$ alkyl)C(O)O$C_1$—$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$—$C_6$ alkyl, —C(O)NH$_2$, —C(O)NH($C_1$-$C_6$ alkyl), —C(O)N($C_1$-$C_6$ alkyl)$_2$, —S$C_1$—$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_1$-$C_6$ alkyl, $C_2$-$C_6$ alkenyl, $C_2$-$C_6$ alkynyl, —$C_3$-$C_6$ cycloalkyl, 3- to 7-membered heterocycloalkyl, $C_1$-$C_6$ alkyl-3- to 7-membered heterocycloalkyl, —CF$_3$, —CHF$_2$, or —CH$_2$F, or a pharmaceutically acceptable salt thereof.

28. The compound of any one of clauses 1 or clauses 23-27, wherein $R^3$ is $C_1$-$C_6$ alkyl, $C_2$-$C_6$ alkenyl, $C_6$-$C_{10}$ aryl, $C_1$-$C_6$ alkyl-(OR$^8$), $C_6$-$C_{10}$ aryl-(OR$^8$), or monocyclic heteroaryl; wherein each hydrogen atom in $C_1$-$C_6$ alkyl, $C_2$-$C_6$ alkenyl, $C_6$-$C_{10}$ aryl, or monocyclic heteroaryl is optionally substituted by deuterium, halogen, —OH, oxo, —OR$^8$, —NHR$^8$, —CN, —O$C_1$—$C_6$ alkyl, —NH$_2$, —NH($C_1$-$C_6$ alkyl), —NH($C_6$-$C_{10}$ aryl), —NH($C_6$-$C_{10}$ aryl)-N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$—$C_6$ alkyl, —N($C_1$-$C_6$ alkyl)C(O)NH$_2$, —N($C_1$-$C_6$ alkyl)C(O)NH$C_1$—$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$—$C_6$ alkyl, —N($C_1$-$C_6$ alkyl)C(O)O$C_1$—$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$—$C_6$ alkyl, —C(O)NH$_2$, —C(O)NH($C_1$-$C_6$ alkyl), —C(O)N($C_1$-$C_6$ alkyl)$_2$, —S$C_1$—$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_1$-$C_6$ alkyl, $C_2$-$C_6$ alkenyl, $C_2$-$C_6$ alkynyl, —$C_3$-$C_6$ cycloalkyl, 3- to 7-membered heterocycloalkyl, $C_1$-$C_6$ alkyl-3- to 7-membered heterocycloalkyl, —CF$_3$, —CHF$_2$, or —CH$_2$F, or a pharmaceutically acceptable salt thereof.

29. The compound of any one of clauses 1 or clauses 23-28, wherein $R^3$ is $C_1$-$C_6$ alkyl, $C_2$-$C_6$ alkenyl, $C_6$-$C_{10}$ aryl, $C_1$-$C_6$ alkyl-(OR$^8$), $C_6$-$C_{10}$ aryl-(OR$^8$), or monocyclic heteroaryl; wherein each hydrogen atom in $C_1$-$C_6$ alkyl, $C_2$-$C_6$ alkenyl, $C_6$-$C_{10}$ aryl, or monocyclic heteroaryl is optionally substituted by deuterium, halogen, —OH, —OR$^8$, —O$C_1$—$C_6$ alkyl, $C_1$-$C_6$ alkyl, or 3- to 7-membered heterocycloalkyl, or a pharmaceutically acceptable salt thereof.

30. The compound of clause 1, wherein the compound is of the formula

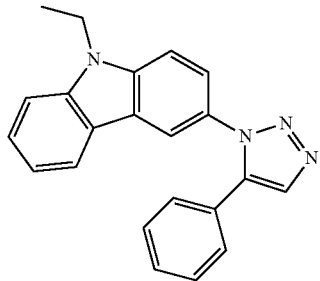 [SMILES: CCn1c2ccccc2c2cc(-n3nncc3-c3ccccc3)ccc21]

or a pharmaceutically acceptable salt thereof.

31. A process for preparing a compound of the formula (I),

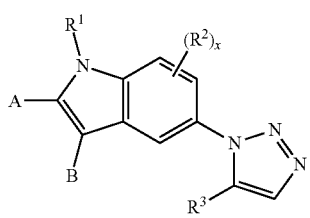

(I)

wherein A and B are independently H, deuterium, halogen, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —OH, —CN, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —OR$^4$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl); or A and B taken together with the ring to which they are attached form a $C_5$-$C_8$ cycloalkyl, $C_6$-$C_{10}$ aryl, or a 5- to 8-membered heterocycloalkyl; wherein each hydrogen atom in $C_1$-$C_6$ alkyl, $C_2$-$C_6$ alkenyl, $C_2$-$C_6$ alkynyl, $C_3$-$C_6$ cycloalkyl, $C_5$-$C_8$ cycloalkyl, $C_6$-$C_{10}$ aryl, or 5- to 8-membered heterocycloalkyl is independently optionally substituted by deuterium, halogen, —OH, —CN, —OR$^4$, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, 3- to 7-membered heterocycloalkyl, —CF$_3$, —CHF$_2$, or —CH$_2$F;

R$^1$ is H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl, or —OR$^5$;

each R$^2$ is independently deuterium, halogen, —OH, —CN, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —OR$^6$, —C(O)OR$^6$, —C(O)NR$^6$R$^7$, —NH$_2$, —NH($C_1$-$C_6$ alkyl), —N($C_1$-$C_6$ alkyl)$_2$, —NHC(O)$C_1$-$C_6$ alkyl, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl); wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OR$^6$, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, —$C_3$-$C_6$ cycloalkyl, or 3- to 7-membered heterocycloalkyl;

R$^3$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, $C_6$-$C_{10}$ aryl-($C_6$-$C_{10}$ aryl), $C_1$-$C_6$ alkyl-(NHR$^8$), $C_1$-$C_6$ alkyl-(OR$^8$), $C_6$-$C_{10}$ aryl-(OR$^8$), $C_1$-$C_6$ alkyl-(NR$^8$R$^9$), or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is optionally substituted by deuterium, halogen, —OH, oxo, —OR$^8$, —NHR$^8$, —CN, —O$C_1$-$C_6$ alkyl, —NH$_2$, —NH($C_1$-$C_6$ alkyl), —NH($C_6$-$C_{10}$ aryl), —NH($C_6$-$C_{10}$ aryl)-N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$ (C₁-C₆ alkyl), —N(C₁-C₆ alkyl)S(O)(C₁-C₆ alkyl), —N(C₁-C₆ alkyl)S(O)₂(C₁-C₆ alkyl), —NHS(O)NH₂, —NHS(O)₂NH₂, —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —NHS(O)N(C₁-C₆ alkyl)₂, —NHS(O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —P(C₁-C₆ alkyl)₂, —P(O)(C₁-C₆ alkyl)₂, C₁-C₆ alkyl, C₂-C₆ alkenyl, C₂-C₆ alkynyl, —C₃-C₆ cycloalkyl, 3- to 7-membered heterocycloalkyl, C₁-C₆ alkyl-(3- to 7-membered heterocycloalkyl), —CF₃, —CHF₂, or —CH₂F;

each R⁴, R⁵, R⁶, R⁷, R⁸, and R⁹ is independently H, deuterium, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, C₁-C₆ alkyl-(3- to 7-membered heterocycloalkyl), heteroaryl, —S(O)₂C₁-C₆ alkyl, —CF₃, —CHF₂, or —CH₂F, wherein each hydrogen in C₆-C₁₀ aryl is optionally substituted by C₃-C₆ cycloalkyl, 3- to 7-membered heterocycloalkyl, or —CH₂CN; and x is 0, 1, 2, or 3, the process comprising contacting a compound of the formula (V),

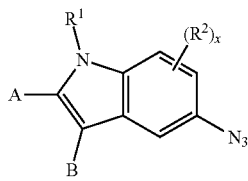
(V)

wherein A, B, R¹, R², and x are as defined in formula (I), with a compound of the formula (VI),

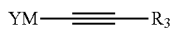
(VI)

wherein R³ is as defined in formula (I), Y is absent or a halogen, and M is a metal, or with a compound of the formula (VIa),

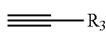
(VIa)

wherein R³ is as defined in formula (I) and a catalyst.

32. The process of clause 31, wherein the compound of formula (VI),

(VI)

is prepared by contacting a compound of the formula (VIa),

(VIa)

with a compound of the formula (VII),

RᴮYX (VII)

wherein Rᴮ is C₁-C₆ alkyl, M is a metal, and Y is a halogen.

33. The process of clause 31 or clause 32, wherein M is magnesium.

34. The process of any one of clauses 31-33, wherein Y is bromo or chloro.

35. The process of clause 31, wherein Y is absent and M comprises zinc.

36. The process of clause 35, wherein the zinc is diethyl zinc.

37. The process of anyone of clauses 31-36, wherein the process further comprises a base.

38. The process of clause 37, wherein the base is N-methylimidazole.

39. The process of clause 31, wherein the catalyst is a ruthenium catalyst.

40. The process of clause 31 or clause 39, wherein the catalyst is (Cp*RuCl)₄.

41. The process of any one of clauses 31-40, wherein the step of contacting is performed in the presence of a polar solvent.

42. The process of clause 41, wherein the polar solvent is THF, DMF, dichloromethane, Et₂O, diglyme, or a mixture thereof.

43. The process of any one of clauses 31-42, wherein the process is carried out at an elevated temperature.

44. The process of clause 43, wherein the elevated temperature is at least 35° C.

45. The process of clause 44, wherein the elevated temperature is selected from a range of about 35° C. to about 65° C.

46. The process of any one of clause 31-45, wherein the compound of the formula (V),

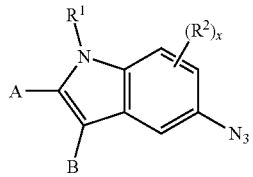
(V)

is prepared by
(a) contacting a compound of the formula (VIII),

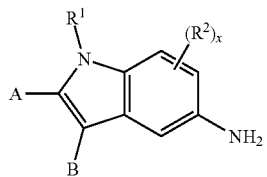
(VIII)

with an acid in an aqueous solvent to form an intermediate, and (b) reacting the intermediate formed in (a) with an azide.

47. The process of clause 46, wherein the acid is a mineral acid.

48. The process of clause 47, wherein the mineral acid is sulfuric acid.

49. The process of any one of clauses 46-48, wherein the azide is sodium azide.

50. The process of any one of clauses 46-49, wherein step (a) further comprises sodium nitrite.

51. The process of any one of clauses 46-50, further comprising purifying the compound of formula (V) by chromatography.

52. The process of any one of clauses 31-51, wherein A and B are taken together with the ring to which they are attached form a $C_6$-$C_{10}$ aryl.

53. The process of any one of clauses 31-52, wherein the compound of formula (I) has the structure of a compound of the formula (III),

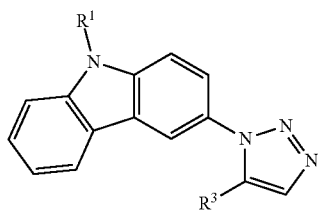

(III)

wherein $R^1$ and $R^3$ are defined as in clause 31, and the compound of formula (V) has the structure of formula (Va),

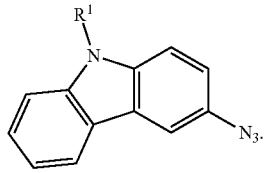

(Va)

54. The process of clause 53, wherein the process comprises the step of contacting the compound of the formula (Va),

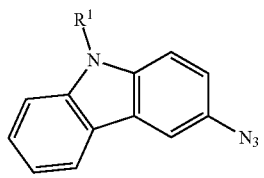

(Va)

with a compound of the formula VI,

(VI)

wherein $R^3$ is $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_1$-$C_6$ alkyl-($OR^8$), or $C_1$-$C_6$ alkyl-($NR^8R^9$), Y is absent and M is a metal, or with a compound of the formula VIa,

(VIa)

wherein $R^3$ is $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_1$-$C_6$ alkyl-($OR^8$), or $C_1$-$C_6$ alkyl-($NR^8R^9$) and a catalyst.

55. The process of clause 54, wherein M comprises zinc.

56. The process of clause 55, wherein the zinc is diethyl zinc.

57. The process of any one of clauses 54-56, wherein the process further comprises a base.

58. The process of clause 57, wherein the base is N-methylimidazole.

59. The process of clause 54, wherein the catalyst is a ruthenium catalyst.

60. The process of clause 54 or clause 59, wherein the catalyst is (Cp*RuCl)$_4$.

61. The process of clause 54, wherein the compound of the formula (Va),

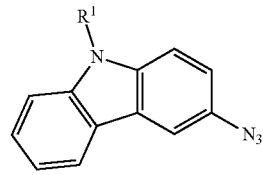

(Va)

is contacted by a compound of the formula (VIa),

(VIa)

and a catalyst.

62. The process of clause 61, wherein the catalyst is a ruthenium catalyst.

63. The process of clause 61, wherein the catalyst is (Cp*RuCl)$_4$.

64. The process of clause 54, wherein the compound of the formula (Va),

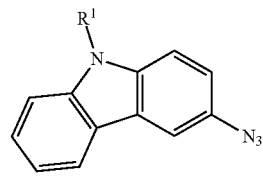

(Va)

is contacted by a compound a compound of the formula (VI),

(VI)

wherein Y is absent and M is a metal.

65. The process of clause 64, wherein M comprises zinc.

66. The process of clause 65, wherein the zinc is diethyl zinc.

67. The process of any one of clauses 64-66, wherein the process further comprises a base.

68. The process of clause 67, wherein the base is N-methylimidazole.

69. The process of clause 53, wherein the process comprises the step of contacting the compound of the formula (Va),

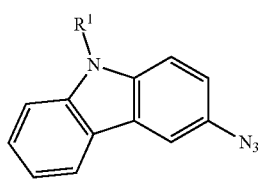

with a compound of the formula (VI),

wherein $R^3$ $C_6$-$C_{10}$ aryl, $C_6$-$C_{10}$ aryl-($C_6$-$C_{10}$ aryl), $C_6$-$C_{10}$ aryl-($OR^8$), or mono- or bicyclic heteroaryl, Y is a halogen, and M is a metal.

70. The process of clause 69, wherein M is magnesium.

71. The process of clause 69 or clause 70, wherein Y is bromo or chloro.

72. The process of any one of clauses 69-71, wherein the process is performed in a polar solvent selected from the group consisting of THF, DMF, dichloromethane, $Et_2O$, diglyme, and a mixture thereof.

73. The process of any one of clauses 69-72, wherein the process is carried out at an elevated temperature.

74. The process of clause 73, wherein the elevated temperature is at least 35° C.

75. The process of clause 73 or clause 74, wherein the elevated temperature is selected from a range of about 35° C. to about 65° C.

76. A method of treating a disease in a patient, the method comprising administering to the patient in need thereof an effective amount of a compound according to any one of clauses 1-30.

77. The method of clause 76, wherein the disease is cancer.

78. The method of clause 76 or clause 77, wherein the compound inhibits cancer cell migration.

79. The method of clause 77 or clause 78, wherein the cancer is selected from the group consisting of breast cancer, pancreatic cancer, ovarian cancer, gastric cancer, and neuronal cancer.

80. The method of clause 79, wherein the cancer is pancreatic cancer.

81. The method of clause 79, wherein the cancer is ovarian cancer.

82. The method of clause 79, wherein the cancer is gastric cancer.

83. The method of clause 79, wherein the cancer is neuronal cancer.

84. The method of clause 79, wherein the cancer is breast cancer.

85. The method of any one of clauses 76-79 or clause 84, wherein the compound inhibits mammosphere formation.

86. The method of any one of clauses 76-85, wherein the compound induces cell cycle arrest of a diseased cell.

87. The method of any one of clauses 76-86, wherein the compound induces apoptosis of a diseased cell.

88. The method of any one of clauses 76-87, wherein the compound reduces the expression of a Bcl-2 protein.

89. The method of any one of clauses 76-88, wherein the disease is mediated by a GTPase.

90. The method of clause 89, wherein the GTPase is Rac 1 or Cdc42.

91. The method of clause 89, wherein the GTPase is Rac1.

92. The method of clause 89, wherein the GTPase is Cdc42.

93. The method of any one of clauses 76-92, wherein the compound inhibits PAK1/2 activity.

94. The method of any one of clauses 76-93, wherein the compound inhibits STAT3 activity.

95. The method of any one of clauses 76-94, wherein the compound is of the formula

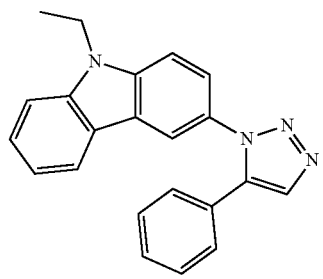 [SMILES: CCn1c2ccccc2c2cc(-n3nncc3-c3ccccc3)ccc21]

or a pharmaceutically acceptable salt thereof.

96. The method of any one of clauses 76-95, wherein the effective amount of the compound is in a range of about 0.01 mg/kg to about 100 mg/kg of body weight of the patient.

97. The method of any one of clauses 76-95, wherein the effective amount of the compound is in a range of about 0.1 mg/kg to about 50 mg/kg of body weight of the patient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A, bright field images of MDA-MB-231 human metastatic breast cancer cells in response to MBQ-167 at 0, 250, and 500 nM; MCF-7 cells in response to MBQ-167 at 0, 250, and 500 nM; FIG. 2B, FIG. 2C, Focal adhesions and actin cytoskeleton following MBQ-167 treatment showing representative fluorescence micrographs of MDA-MB-231 cells, MDA-MB-231 cells were treated with 0, 250, or 500 nM MBQ-167 for 24 h and fixed and stained in FIG. 2B, with phospho-tyrosine antibodies (P-Tyro) for focal adhesions (green) and Rhodamine phalloidin for F-actin (red) and in FIG. 2C, with anti vinculin (red); Arrows, invadopodia; arrowheads, focal adhesions.

FIGS. 3A-1, 3A-2, 3B-1, 3B-2, 3C, 3D. Inhibitory effect of MBQ-167 on Rac and Cdc42 activation. MDA-MB-231 human breast cancer cells were treated for 24 h with 250 nM MBQ-167; The attached (250A) and detached (250D) cell populations were recovered and equal amounts of proteins subjected to pulldown assays using the p21-binding domain of PAK to isolate the GTP bound Rac and Cdc42; Cell lysates were western blotted with antibodies to Rac or Cdc42; Results from positive bands in western blots were quantified using image J; FIG. 3A-1, Representative western blot for Rac1/2/; FIG. 3A-2 quantification of Rac activation at 24 h following 0 or 250 nM MBQ-167; FIG. 3B-1 Representative western blot for Cdc42; FIG. 3B-2 quantification of Cdc42 activation following 24 h treatment with 0 or 250 nM MBQ-167; The integrated density for active Rac or Cdc42 (GTP) was divided by the total Rac or Cdc42 from the same cell lysates; Rac or Cdc42 activity for each MBQ-167 treatment was divided by the vehicle controls for each experiment to obtain Relative Rac or Cdc42 activity; N=3, *=P<0.05, ***=P<0.001; Error bars represent ±S.E.M. FIG. 3C, D, MDA-MB-231 cells with vehicle control (0.1% DMSO) or varying concentrations of MBQ-167 (0-1000 nM) were treated for 24 hrs; Total cell lysates using combined attached and detached treated populations were subjected to the G-LISA Rac1/2/3 (FIG. 3C) or Cdc42 activation assay; $IC_{50}$ curves for percentage Rac FIG. 3C or Cdc42 FIG. 3D activation are relative to vehicle from three biological replicates each with two technical replicates; Error bars represent ±S.D. Four-parameter dose-response curves generated using GraphPad Prism® are shown.

FIGS. 4A-1, 4A-2, 4B, 4C, 4D-1, 4D-2, 4E-1, 4E-2, 4F, 4G. The effect of MBQ-167 on signaling downstream of Rac and Cdc42.4A, The effect of MBQ-167 on PAK1 and PAK2 phosphorylation as measured by western blotting for pPAK1 (T423)/pPAK2 (T402), pPAK1 (S199)/pPAK2 (S192), and pPAK1 (S144) levels in MDA-MB-231 cells after 24 hours of treatment in 0 or 250 nM MBQ-167; FIG. 4A-1 Data for separate attached (Att) and detached (Det) populations are shown; representative western blots (N=3) FIG. 4A-2; relative PAK activity following MBQ-167 treatment; Positive bands from all western blots were quantified using image J; The integrated density of p-PAK was divided by that of total PAK for the same cell lysate and used as a measure of PAK activity for each phospho PAK residue; Relative PAK activity was determined relative to vehicle controls for each experiment; N=3, *=P<0.05, =P<0.01, *=P<0.001; Error bars represent ±S.E.M. FIG. 4B, Effect of MBQ-167 on PAK downstream effectors LIMK and cofilin phosphorylation; MDA-MB-231 cells were incubated for 4, 12, or 24 h in vehicle or 250 nM MBQ-167, the attached 250A and detached 250D populations were separated, lysed, and equal protein used for western blotting; Representative western blot of total LIMK1 or p-LIMK1/2 (Y507/T508) following 24 h in 0 or 250 nM MBQ-167 (N=2) is shown; FIG. 4C, Representative western blot of total or p-cofilin (S3) of equal amounts of total protein lysates following 4, 12, or 24 h in 250 nM MBQ-167 (N=3); Separated attached 250A and detached 250D populations are shown for 12 and 24 h of MBQ-167 treatment; FIG. 4D-1, FIG. 4D-2, Effect of MBQ-167 on STAT3 phosphorylation and expression; Representative western blot is shown for pSTAT3 (Y705) and total STAT3 expression in GFP-HER2-BM cells after 24 h treatment with vehicle or 100, 200, or 500 nM MBQ-167; FIG. 4D-1 Representative western blot FIG. 4D-2 and quantification; N=3, *=P<0.05, Error bars represent ±S.E.M. E, F, Effect of MBQ-167 on cell migration; FIG. 4E-1, The effect of MBQ-167 on MDA-MB-231 cellular migration as measured by a transwell assay; Images are representative of three independent experiments; FIG. 4E-2 The Graph shows quantification of 20 microscopic fields per treatment per experiment of PI stained cells that migrated to the underside of the membrane through 8 micron diameter pores N=3, *=P<0.05, Error bars represent ±S.E.M. FIG. 4F, The effect of MBQ-167 on cell migration in a scratch assay; MDA-MB-231 cells plated at equal density were subjected to a scratch in the center and treated with MBQ-167 at 0, 250, or 500 nM; Micrographs were digitally acquired at 0 and 24 h and the distance of the scratch quantified for each treatment and presented relative to the distance at time 0; Results are an average of two technical replicates and two biological replicates for each treatment±S.D,*=P<0.05; FIG. 4G, The effect of MBQ-167 on mammosphere forming efficiency in MDA-MB-231 cells; MDA-MB-231 cells treated with 0 or 250 nM MBQ-167 were subjected to mammosphere assays for 4 days; Cells were treated with MBQ-167 only once prior to placing on the mammosphere medium; Mammosphere forming efficiency was calculated as the percentage of the number of mammospheres divided by the number of cells seeded per well; N=3, ***=P<0.001, Error bars represent ±S.D.

FIGS. 5A, 5B-1, 5B-2, 5C-1, 5C-2, 5D-1, 5D-2. Effect of MBQ-167 on cell survival. 5A, The effect of MBQ-167 on MDA-MB-231, GFP-HER2-BM, and MCF10A cell viability. Equal numbers of each respective cell line were treated with vehicle control (0.1% DMSO) or varying concentrations of MBQ-167 (0-1000 nM) for 120 h; $GI_{50}$ curves for percentage cell viability are relative to vehicle from three biological replicates each with two technical replicates; Four-parameter dose-response curves generated using GraphPad Prism® are shown; N=3, Error bars represent ±S.E.M. FIG. 5B-1, FIG. 5B-2, The effect of MBQ-167 on cell cycle progression; Equal numbers of MDA-MB-231 cells in either vehicle control or treatment groups were treated for 24 h with 0 or 250 nM MBQ-167; Graphs represent the percentage of control versus 250 nM MBQ-167 treated cells stained with PI in $G_0/G_1$, S, or $G_2/M$ phases of the cell cycle; FIG. 5B-1 representative flow cytometry analysis FIG. 5B-2; quantification of cell cycle stage; N=3, Error bars±S.E.M. FIG. 5C-1, FIG. 5C-2, The effect of MBQ-167 on caspase3,-7 activity; FIG. 5C-1, caspase3/7 activity of MDA-MB-231 and GFP-HER2-BM cells (including attached and detached populations) following vehicle (0.1% DMSO) or varying concentrations of MBQ-167 (0-1000 nM) for 24 h; N=3, Error bars represent ±S.E.M. FIG. 5C-2, the effect of MBQ-167 on caspase-3,-7 activity of MDA-MB-231 cells; Cells were treated with 250 nM MBQ-167 for 24 h and equal numbers of separated attached and detached cells were lysed and used for caspase 3/7 assays; Caspase-3,-7 activity relative to equal number of attached cells from control cells is shown; N=3, Error bars represent ±S.E.M. FIG. 5D-1, FIG. 5D-2, The effect of MBQ-167 on mitochondrial regulation of apoptosis; The effect of MBQ-167 on the expression of the pro-survival proteins Bcl-2, Bcl-xL, and Mcl-1 in MDA-MB-231 cells after 24 h of treatment; FIG. 5D-1, representative western blot FIG. 5D-2; quantification of the integrated density of positive bands using image J; N=3, *=P<0.05, ***=P<0.001, Error bars represent ±S.E.M.

FIGS. 6A-1, 6A-2, 6B, 6C, 6D, 6E. In-vivo efficacy of MBQ-167 in HER2-type breast cancer. Mammary fatpad tumors were established in nude mice by inoculating $5 \times 10^5$ GFP-HER2-BM cells; Following one week, mice were treated with vehicle control or 1.0, or 10.0 mg/kg body weight (BW) MBQ-167 3× a week by i.p. injection; 6A-1, representative excised tumors following 0, 1, 10 mg/kg BW MBQ-167; FIG. 6A-2, average relative tumor growth from fluorescence in situ images up to 65 days following 0, 1.0, or 10 mg/kg BW MBQ-167 (3× a wk) (N=6); FIG. 6B, Representative fluorescence micrographs of lungs, spleens, and kidneys from vehicle or MBQ-167 treated mice following necropsy; FIG. 6C, Mouse weights from 1-65 days; FIG. 6D, FIG. 6E, Liver enzyme activities following MBQ-167 treatment; Following necropsy, livers were harvested, lysed and subjected to FIG. 6D, ALP activity or FIG. 6E, ALT activity assays; N=4, error bars represent ±S.E.M.

FIG. 7. The effect of MBQ-167 on the Rac activity of metastatic cancer cells expressing a constitutively active Rac (Rac1G12V). MDA-MB-435 human metastatic cancer cells expressing wild type Rac1 (WT) or Rac1(G12V) constitutively activated form were treated for 24 h with 250 nM MBQ-167; The attached 250A and detached 250D cell populations were recovered and equal amounts of proteins subjected to pulldown assays using the p21-binding domain of PAK to isolate the GTP bound Rac; Cell lysates were western blotted with antibodies to Rac; Results from positive bands in western blots were quantified using image J; Results show that even though MBQ-167 significantly inhibited the Rac activity of the detached cells expressing wild type Rac, this inhibition was not observed in cells expressing a constitutively active GTP bound form of Rac1.

FIGS. 8A, 8B. The effect of MBQ-167 on survival and PAK activity in NCI-N87 gastric cancer cells. FIG. 8A; Equal numbers of NCI-N87 cells in either vehicle control or treatment groups were treated for 24 h with 0 or 250 nM MBQ-167; Cells were subjected to MTT assays for viability; Results show that 250 nM MBQ-167 for 24 h reduces NCI-N87 cell viability by 50%; FIG. 8B; Equal numbers of cells treated with 0, 250, or 500 nM MBQ-167 were lysed and western blotted for phospho (P)-PAK1$^{T432}$ (active form) or total PAK1, or phospho (P)-PAK4$^{S474}$ (active form) or total PAK4; Representative western blot shown demonstrates that MBQ-167 inhibits both PAK1 and PAK4 activities in the NCI-N87 gastric cancer cells.

FIG. 12A, The effect of MBQ-167 on PAK1 and PAK2 phosphorylation as measured by western blotting for STAT3 and p-STAT3 (Y705) levels in MDA-MB-231 and GFP-HER2-BM cells after 24 hours of treatment in 0 or 250 nM MBQ-167; Data for separate attached 250A and detached 250D populations are shown; Representative western blots (N=2); FIG. 12B, The effect of MBQ-167 on GFP-HER2-BM cell migration as measured by a Transwell assay; The Graph shows quantification of 20 microscopic fields per treatment per experiment of PI stained cells that migrated to the underside of the membrane through 8 micron diameter pores in 6 h, N=3,*=P<0.05, Error bars represent ±S.E.M.

FIG. 15A Top left, representative micrograph of the budding phenotype in the absence of Doxycycline; FIG. 15B Top right, representative micrograph of same cell strain following 24 h in 25 μM MBQ-167; FIG. 15C, representative micrograph of cells following 10 μg/ml doxycycline to knockdown Cdc42; FIG. 15D Bottom right, representative micrograph of cells with both Cdc42 knockdown and 25 μM MBQ-167.

DETAILED DESCRIPTION

Figure 1:
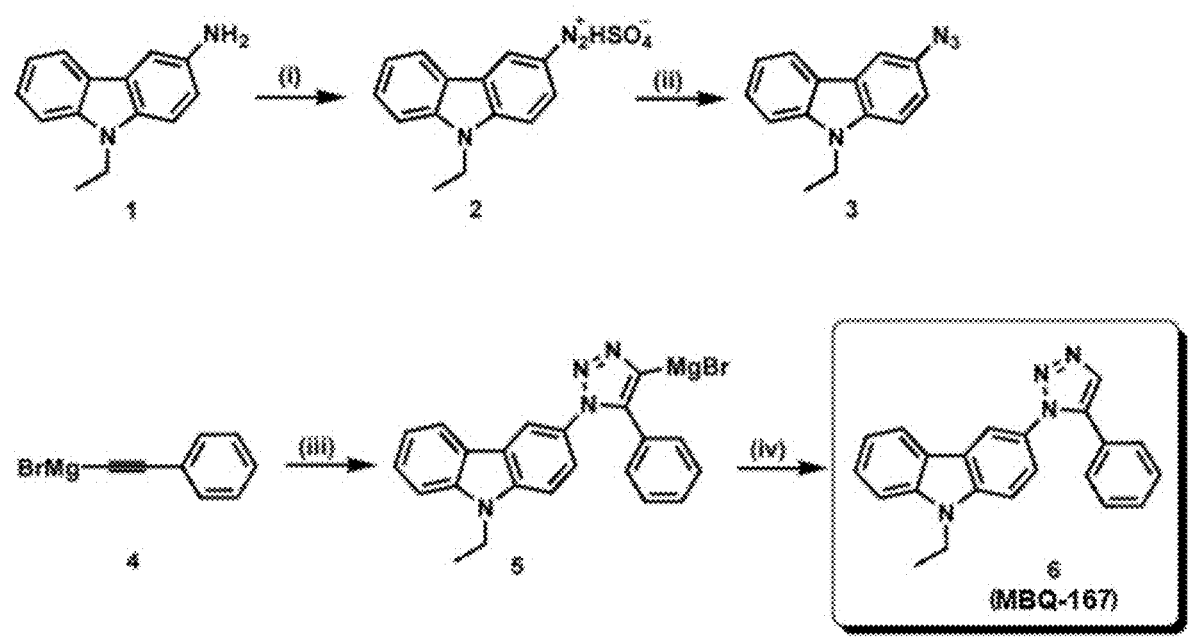
FIG. 1. Design and synthesis of MBQ-167. Synthesis of MBQ-167. Reaction conditions: (i) conc. $H_2SO_4$, $NaNO_2$, water 0-5° C., 1 h; (ii) $NaN_3$, 0° C., 1 h, 76%; (iii) THF, 3, 50° C., 1 h; (iv) $NH_4Cl$ (aq), 86%.

Two compounds that inhibit Rho GTPases, Rac and Cdc42, have also been used as drug targets. NSC23766 was the first Rac inhibitor shown to block the interaction of Rac with the GEFs Trio and Tiam1; however, its high effective concentrations (IC$_{50}$>75 μM) limits its therapeutic use. A panel of putative Rac and Cdc42 inhibitors led to the identification of EHop-016. EHop-016 blocks the interaction of the GEF Vav2 with Rac, and inhibits Rac activity at an IC50 of ~1.1 μM, which makes it ~100× more potent than NSC23766. EHop-016 also inhibits Cdc42 activity at concentrations of ≥10 μM, without affecting Rho activity.

At 25 mg/kg body weight (BW), EHop-016 reduces mammary tumor growth, metastasis, and angiogenesis without apparent toxicity in nude mice. The pharmacokinetics analysis of EHop-016, after oral and intraperitoneal (i.p.) administration, demonstrated a bioavailability of ~30% with an average half-life of ~4.5 h, indicating its potential as a cancer therapeutic in breast cancer, and subsequently in other types of cancer.

Although other small molecule inhibitors, such as the NSC23766 derivative Aza-1 (inhibits both Rac and Cdc42) and CID2950007/ML141 (selective for Cdc42) are currently available, they are effective in the micromolar range. A goal was to develop a Rac/Cdc42 inhibitor with improved activities led to the identification of MBQ-167. Compared to EHop-016, MBQ-167 is a 10× more potent inhibitor of Rac and a 100× more potent inhibitor of Cdc42, which resulted in an enhanced inhibition of cancer malignancy.

Substituents A and B can alternatively form a ring system:

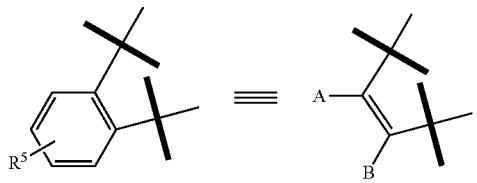

Wherein:
R5 is independently in each occurrence hydrogen, halide, hydroxyl, cyano, C1-6 alkyl, C3-6 cycloalkyl, C1-6 haloalkyl, nitro, amino, etc.

A compound according to formula I, includes one or more compounds selected from the compounds in TABLE I.

There is a method for inhibiting Rac and Cdc42 activity in a cell by treatment with compound I, wherein R1, R2, R3, R4, R5, Ra, Rb, and A and B are defined as above.

There is a method for inhibiting Rac and Cdc42 activity in a patient with cancer of hyperproliferative disorder by treatment with compound I, wherein R1, R2, R3, R4, R5, Ra, Rb, and A and B are defined as above.

Compounds and Preparation

The 1,5-disubstituted 1,2,3-triazoles can be prepared in a two-step process according to Scheme A, comprising step 1) formation of the azide from the corresponding amine; and step 2) formation of the 1,5-triazole by reacting the azide with an alkyne in one of the conditions described below.

SCHEME A

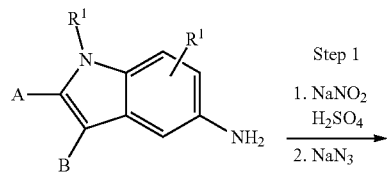

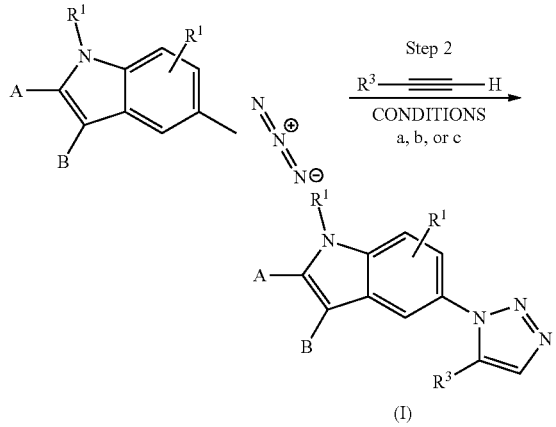

Step 1 can be carried out by contacting a slurry of the appropriate aromatic amine in water with concentrated sulfuric acid, followed by the dropwise addition of an aqueous solution of sodium nitrite. Following completion of the formation of the intermediate diazo-derivative, an aqueous solution of sodium azide is added, providing the azide product of step 1.

Step 2 can be carried out under various conditions that selectively provide the 1,5-substituted 1,2,3-triazole products (in contrast with the more commonly prepared 1,4-substituted 1,2,3-triazole product). The most commonly employed methods in the literature include:

a) Contacting the primary alkyne with a Grignard reagent such as ethylmagnesium bromide, which provides the alkynylmagnesium bromide. Subsequently reacting the alkynylmagnesium bromide product with the azide from step 1 selectively gives the 1,5-disubstituted 1,2,3-triazole b) Contacting the primary alkyne with the azide in the presence of pentamethylcyclopentadienyl ruthenium chloride regioselectively leads to the 1,5-disubstituted 1,2,3-triazole c) Contacting the primary alkyne with the azide in the presence of diethyl zinc and N-methylimidazole.

Many of the aromatic amine and alkyne starting materials are commercially available or could be prepared via published procedures. Alternatively, modifications can be introduced after the cyclization reaction has been performed. In some cases, protecting group strategies need to be applied.

Compounds are disclosed that inhibit RhoGTPases and therefore are useful for inhibiting hyperprofilerative and neoplastic diseases. Specifically, the compounds inhibit the GTPases Rac and Cdc42 that are overactive or overexpressed in signaling pathways in cancer and metastasis. These compounds are useful for the treatment of cancer and hyperproliferative diseases.

Figures 1, 3A:
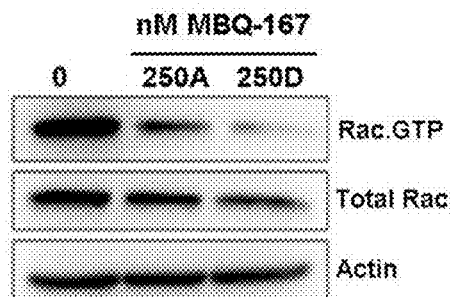
Figures 2, 3A:
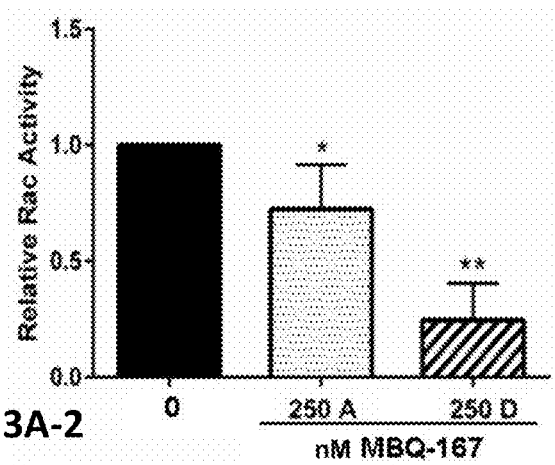
Figures 1, 3B:
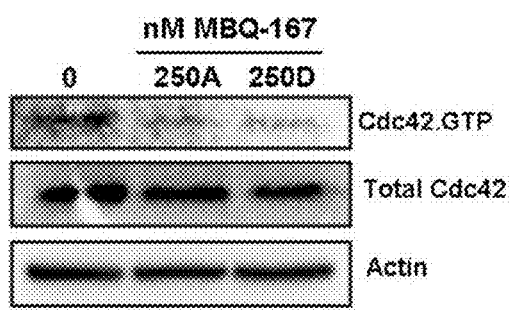
Figures 2, 3B:
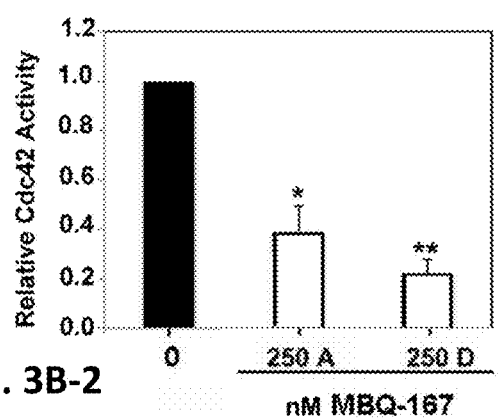
Figure 3C:
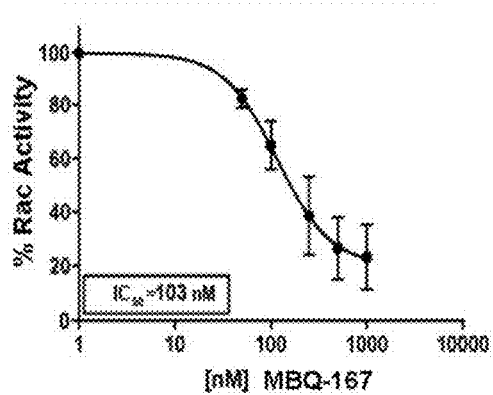
Figure 10A:
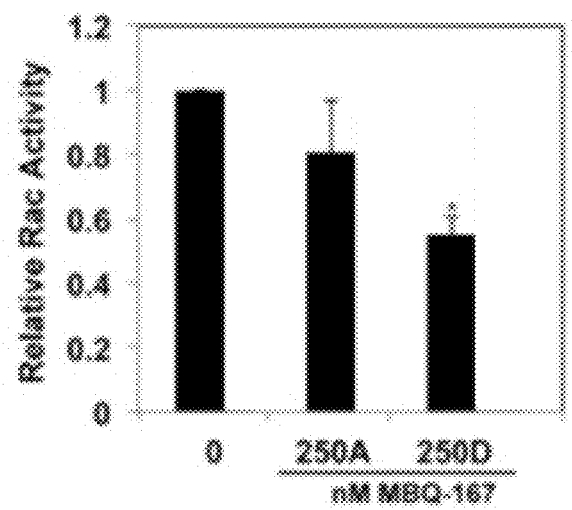
FIGS. 10A, 10B, 10C. Effect of MBQ-167 on Rho GTPase activity in GFP-HER2-BM cells. GFP-HER2-BM cells were treated for 24 h with 250 nM MBQ-167; The attached 250A and detached 250D cell populations were recovered and equal amounts of proteins subjected to G-LISA assays for FIG. 10A Rac or Cdc42 FIG. 10B, FIG. 10C GFP-HER2-BM human breast cancer cells were treated with 0 or MBQ-167 for 24 h were lysed (both attached and detached cells) and incubated with the Rho-binding domain from Rhotekin to isolate active Rho; Cell lysates were western blotted with antibodies to Rac, Cdc42, or Rho; Results from positive bands in western blots were quantified using image J; The integrated density for active Rho was divided by the total Rho from the same cell lysates; Rac, Cdc42, or Rho activity for each MBQ-167 treatment was divided by the vehicle controls for each experiment to obtain Relative activity.
Figure 10B:
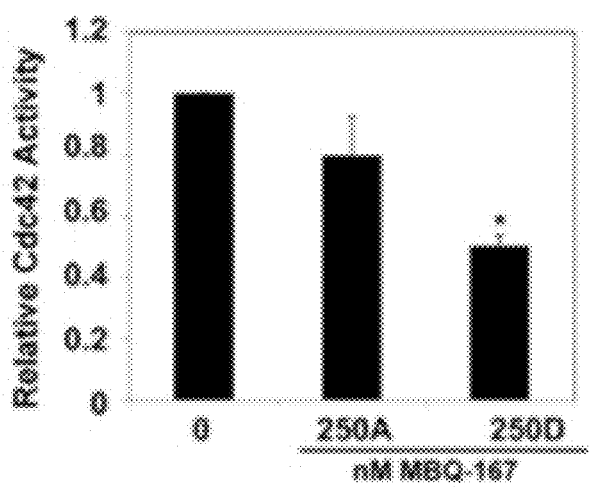

A series of 1,5-disubstituted 1,2,3-triazoles as novel inhibitors of Rac and Cdc42. One specific example (MBQ-167) (previously EHop-167) was studied in extensive detail. MBQ-167 inhibits Rac and Cdc42 activation in metastatic cancer cells MDA-MB-231 and GFP-HER2-BM Cells were Treated for 24 h with Vehicle or MBQ-167, and the detached and attached cells (~50% for each population), were recovered and lysed immediately. Equal amounts of protein were subjected to activation assays for Rac or Cdc42. Following treatment with 250 nM MBQ-167 for 24 h, the attached population of MDA-MB-231 cells demonstrated a ~25% decrease in Rac activation while the detached cells were more responsive with a ~75% decrease (FIG. 3A-1, 3A-2). At earlier times (6 h), treatment with 250 or 500 nm MBQ-167, induced a 10-20% inhibition in Rac activity in the attached cell population, while the detached population demonstrated a ~40-50% inhibition. Similarly, Cdc42 activity was inhibited by 60% in the attached cells and 78% in the detached MDA-MB-231 cells following 250 nM MBQ-167 for 24 h (FIG. 3C). These results indicate that both Rac and Cdc42 activities are inhibited while the cells are still attached to the substratum but the more responsive cells gets detached first. Incubation of MDA-MB-231 cells with 500 nM MBQ-167 for 24 h resulted in ~90% detachment of cells and a parallel decrease in Rac and Cdc42 activities, demonstrating that a majority of the cells were responsive to MBQ-167. Similarly the GFP-HER2-BM highly metastatic breast cancer cell line responded to MBQ-167 by inhibition of Rac and Cdc42 activities significantly in the detached cell populations (FIGS. 10A, 10B). However, the non-metastatic more epithelial MCF-7 cell line, which did not respond to MBQ-167 by the cell detachment phenotype, was also insensitive to MBQ-167 treatment in Rac inhibition. This may be due to differences in the Rac and Cdc42 GEFs that are expressed and activated in metastatic breast cancer cell lines (MDA-MB-231) compared to the less metastatic more epithelial MCF-7 cell line.

Figure 3D:
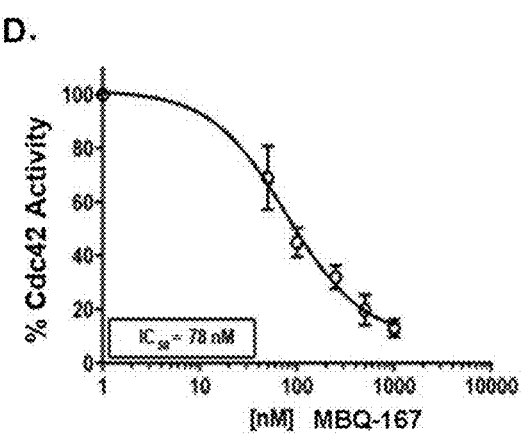

Next, as a measure of the specificity of MBQ-167 as a Rac/Cdc42 inhibitor, the $IC_{50}$s for Rac and Cdc42 activation were also determined following 24 h in MBQ-167 using combined attached and detached populations. Results show that MBQ-167 inhibits Rac 1/2/3 activity in the MDA-MB-231 cells with an $IC_{50}$ of 103 nM, and Cdc42 activity with an $IC_{50}$ of 78 nM (FIG. 3D). Since the $IC_{50}$ for Rac inhibition by EHop-016 is 1.1 µM and Cdc42 inhibition is ~8 µM (16), MBQ-167 is 10× more potent than EHop-016 for Rac inhibition and 100× more potent for Cdc42 inhibition.

To indirectly determine the specificity of MBQ-167 for inhibiting Rac activation by GEFs, Rac activity was determined from previously characterized MDA-MB-435Br cells expressing a control vector or constitutively active (Rac1G12V). However, MBQ-167 did not affect the Rac activity of this cell line expressing a Rac1(G12V) (FIG. 7), indicating that constitutive activation of Rac desensitizes the cells to inhibition by MBQ-167. Moreover, as demonstrated from activation assays for Rac, Cdc42, and Rho from attached and detached cell populations, MBQ-167 did not affect the related GTPase Rho activation in both cell populations of MDA-MB-231 and GFP-HER2-BM metastatic cancer cells (Table 1, FIG. 10).

MBQ-167 Inhibits Rac and Cdc42 Downstream Effectors

Figure 2A:
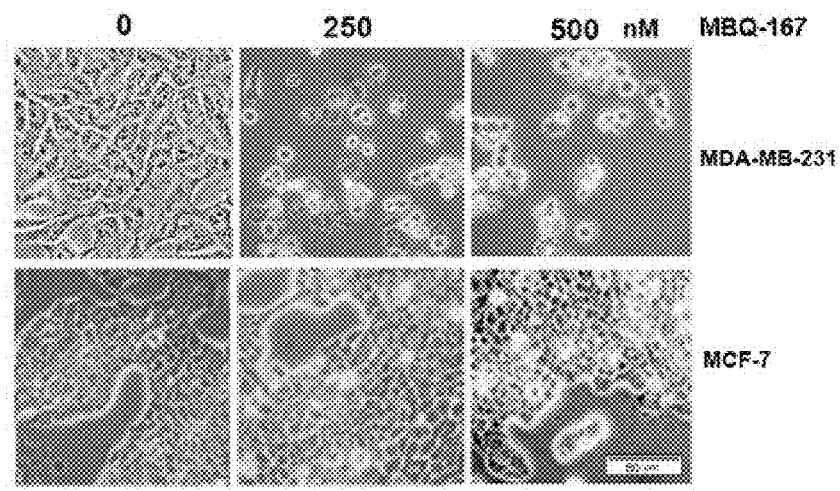
FIGS. 2A, 2B, 2C. Breast cancer cell phenotype following MBQ-167 treatment.
Figure 2B:
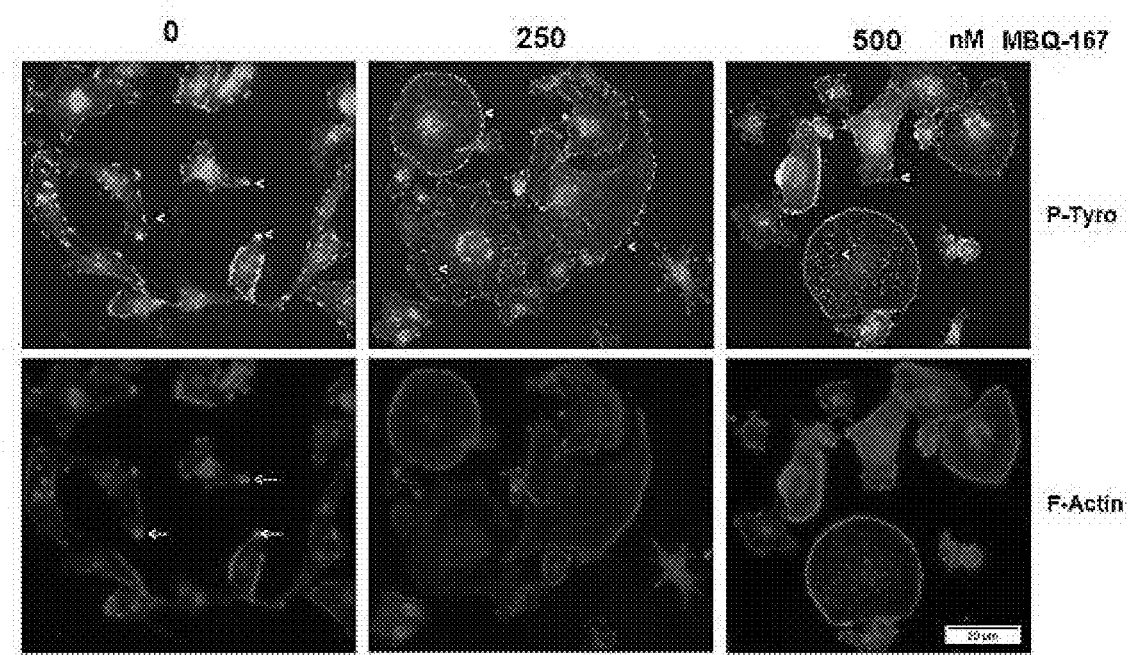
Figures 1, 4A:
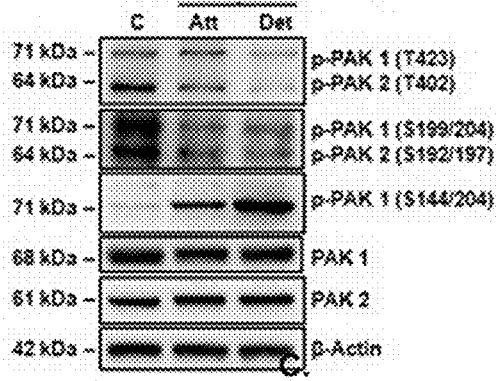
Figures 2, 4A:
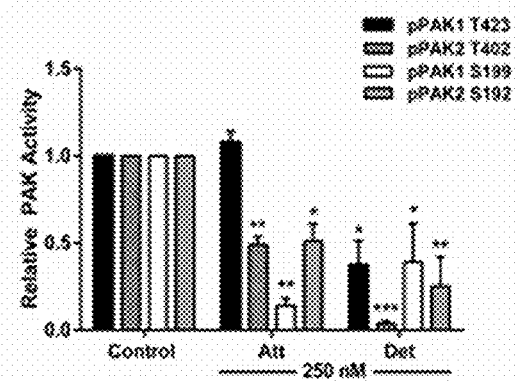

To investigate the effect of MBQ-167 on Rac/Cdc42 signaling, its effect on the major Rac/Cdc42 downstream effector PAK was investigated. The phosphorylation status of several PAK residues was analyzed by western blotting, as a measure of its activity. At 250 nM, 24 h treatment with MBQ-167 inhibited PAK1 and PAK2 phosphorylation at the T423/T402 and S 199/S 192 residues in the detached population of MDA-MB-231 cells. Except for PAK1$^{T423}$, phosphorylation of all of these residues was significantly decreased in the attached population as well. Even though PAK1$^{T423}$ phosphorylation was not inhibited in the attached cells, the reduction in the homologous PAK2 phosphorylation sites indicates a preferential inhibition of PAK2 in the attached cells (FIGS. 4A-1, 4A-2, FIG. 4B-1). Interestingly, MBQ-167 induced a dramatic increase in the phosphorylation of the PAK1$^{S144}$ (FIG. 4A-1, 4A-2). However, overall PAK activity is inhibited by MBQ-167, because the activating phosphorylation (Y507/T508) of the direct PAK substrate LIM kinase (LIMK) and the inactivating phosphorylation (S3) of cofilin (actin depolymerization factor), a downstream effector of LIMK, were both decreased following MBQ-167 treatment. The decrease in cofilin phosphorylation was evident after 12 h following 250 nM MBQ-167 (FIG. 4C), indicating activation of cofilin, which account for the observed actin cytoskeletal restructuring (FIG. 2B). Moreover, in the MCF7 cell line, which did not respond to MBQ-167 by cell detachment or inhibition of Rac activation, MBQ-167 also did not affect PAK activity. Similarly, in the NCI-N87 human metastatic gastric cancer cell line, MBQ-167 inhibited the viability and the activity of PAK isoforms PAK1 and PAK4, which have been implicated in gastric cancer malignancy (FIG. 8B).

Rac activity has also been shown to directly stimulate the activity of the transcription factor, STAT3 (30). As seen in FIGS. 4D-1, 4D-2 and FIG. 12A, MBQ-167 decreased STAT3 activity following 24 h exposure in both the attached and detached populations of MDA-MB-231 and GFP-HER2-BM cells. However, MBQ-167 did not affect mitogen activated protein kinase (MAPK) activities, either p38-MAPK or the p42/44 MAPK, as well as Akt activities as demonstrated by western blotting with phospho-specific antibodies (FIG. 13A, 13B).

MBQ-167 Affects Cancer Cell Polarity

Figure 9:
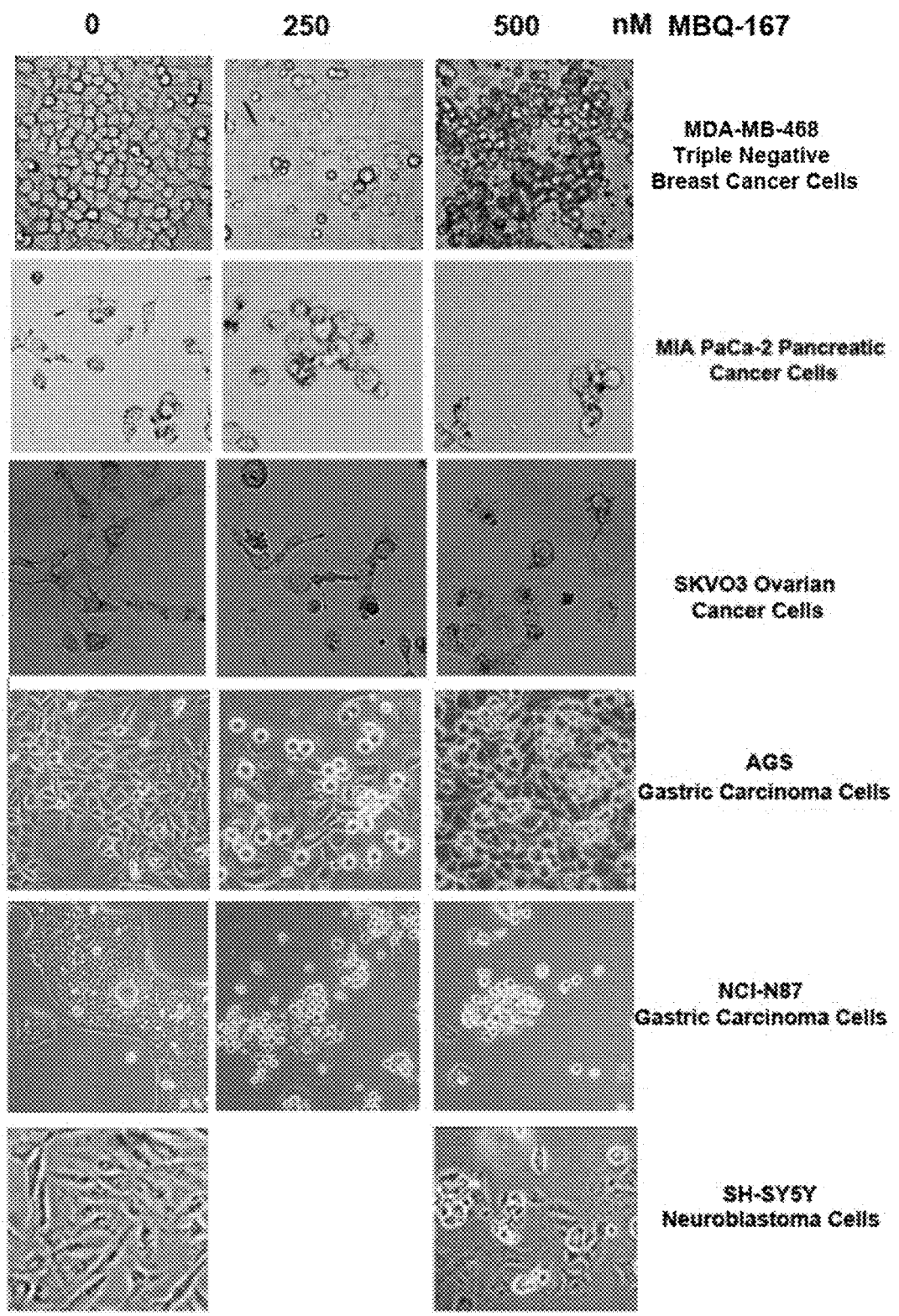
FIG. 9. Human cancer cell phenotype following MBQ-167 treatment. Triple negative breast cancer (MDA-MB-468), aggressive pancreatic (Mia PaCa-2), ovarian (SKVO3), gastric carcinoma (AGS and NCI-N87) cell lines and a neuroblastoma (SH-SY5Y) cell line were treated with 0, 250 or 500 nM MBQ-167 for 24 h; Representative bright field images are shown for each cell line.

Human breast cancer cells were visualized by bright field microscopy following MBQ-167 treatment. At ≥100 nM, starting at six hours, MBQ-167 induced a loss of polarity in metastatic breast cancer cells. Treatment with 500 nM MBQ-167 for 24 h resulted in ~95% cell rounding and detachment from the substratum in metastatic MDA-MB-231 cells (FIG. 2A). Moreover, MBQ-167 induced this phenotype in multiple mesenchymal cancer cell types including GFP-HER2-BM, MDA-MB-468, and Hs578t human breast cancer cells, as well as Mia-PaCa-2 pancreatic cancer cells, SKOV3 ovarian cancer cells, AGS and NCI-N87 gastric cancer cells, and SH-SY5Y neuroblastoma cells (FIG. 9). On the other hand, non-cancer mammary epithelial MCF10A and epithelial breast cancer MCF-7 cells were resistant to MBQ-167 and remained polarized and attached to each other and the substratum (FIG. 2A). This indicates that MBQ-167 only affects cancer cell lines that have gone through epithelial-mesenchymal (EMT) transition, and does not affect non-cancer epithelial cell lines or cancerous epithelial cell lines.

Figure 11:
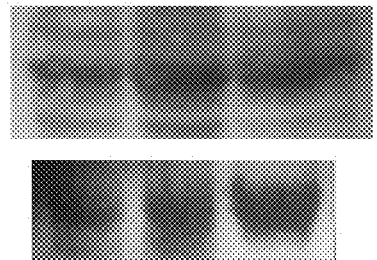
FIG. 11. MBQ-167 does not affect PAK activity in MCF-7 cells. MCF-7 cells were treated with 0 or 250 nM MBQ-167 for 24 h and the attached 250A and detached 250D cells were recovered separately; Equal amounts of protein were run on SDS-PAGE and western blotted with a phospho-PAK (T423) or total PAK antibody; Representative western (N=2) is shown.

To further investigate the effect of MBQ-167 on MDA-MB-231 cells, immunofluorescence microscopy was performed following 0-500 nM MBQ-167 to detect actin dynamics (by Rhodamine phalloidin) and focal adhesions (by anti-p-tyrosine and anti-vinculin). MBQ-167 rearranged the actin cytoskeleton and focal adhesions to result in loss of cell polarity and attachment to the extracellular matrix (ECM), with a marked reduction in both Rac-regulated lamellipodia/invadopodia and Cdc42-induced microspikes and filopodia (FIG. 11). Moreover, in MBQ-167-treated cells, the focal adhesions were reduced from the cell edge and rearranged from the cytoskeleton to the center of the rounded detaching cells.

Figure 2C:
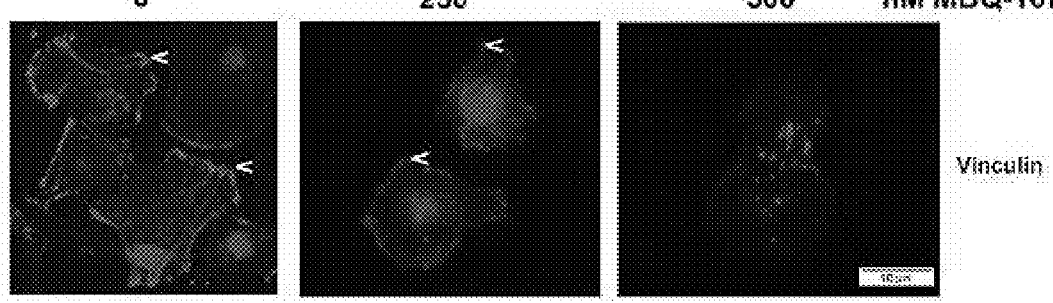

Therefore, MBQ-167 inhibits cell polarization, extension of lamellipodia and filopodia, and focal adhesion formation at the leading cell edge (FIG. 2B, FIG. 2C). Growth of yeast cells that only express Cdc42 and not Rac were also inhibited by MBQ-167 with a characteristic loss in bud polarity (FIG. 15A, 15B, 15C, 15D).

MBQ-167 Inhibits Cell Migration and Mammosphere Formation

Rac/Cdc42 and its downstream effector PAK directly regulate cell migration. The effect of MBQ-167 on MDA-MB-231 cell migration was investigated. The two cell populations (detached and attached) were recovered following 18 h in MBQ-167 and equal numbers of cells (vehicle-treated, and MBQ-167-treated attached and detached populations) were used for a Transwell assay for 6 h. This short incubation time is not sufficient for MDA-MB-231 cell division (doubling time of ~38 h) or inhibition of cell viability (Suppl. FIG. 8B, 8C). Therefore, the assay only measures the efficiency of cell migration.

MBQ-167 treatment reduced directed migration of the attached MDA-MB-231 cell population by ~60-70% at 250 and 500 nM. In the detached population, MBQ-167 (250 and 500 nM) inhibited cell migration by ~90% in a statistically significant manner (FIG. 4E-1, 4E-2). In the more metastatic GFP-HER2-BM cell line, 250 and 500 nM MBQ-167 inhibited cell migration by 80-90% in both attached and detached cells. These results were confirmed in a wound healing assay where 250 and 500 nM MBQ-167 treatment for 24 h resulted in statistically significant ~80 and 90% inhibition of wound closure, respectively (FIG. 4F). STAT3 and Rac activities have been implicated in enhanced breast cancer stem cell-like properties and therapy resistance. The capacity of MBQ-167 to target cancer stem cell populations using a mammosphere formation assay. Addition of MBQ-167 once for four days reduced the mammosphere forming efficiency of MDA-MB-231 cells by ~50% following 24 h treatment with MBQ-167 (FIG. 4F).

MBQ-167 Inhibits Cell Survival

MBQ-167 induces a phenotype characterized by cell rounding, loss of lamellipodia, and eventual detachment from the surface substratum (FIG. 2A, 2B, 2C). Therefore, we tested the potential of MBQ-167 was tested to induce anoikis: apoptosis due to dissolution of integrin-mediated cell to ECM attachments. It should be emphasized that the metastatic cancer cells that detach in response to MBQ-167 following 24 h treatment are viable, as evidenced by trypan blue exclusion from live cells (FIG. 8A). These detached cells also have the capacity for regrowth when replated without MBQ-167 (data not shown). As shown in FIG. 8B, MDA-MB-231 cells are 100% viable at concentrations ≤300 nM for 24 h. At 24 h MBQ-167 treatment, ~75% of MDA-MB-231, GFP-HER2-BM, and MCF-7 breast cancer cells, as well as the MCF-10 mammary epithelial cells are viable even at 5 µM MBQ-167. Prolonged treatment for 48, 96, and 120 h with MBQ-167 results in cell detachment from the substratum and loss of cell viability.

Figure 5A:
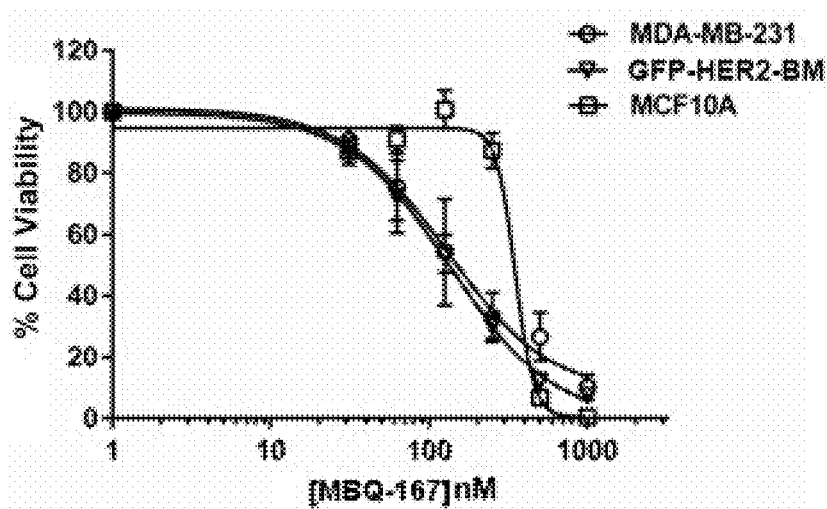
Figures 1, 5B:
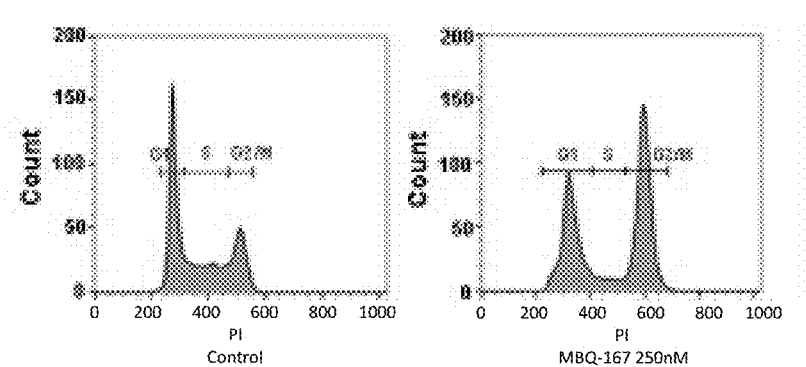
Figures 2, 5B:
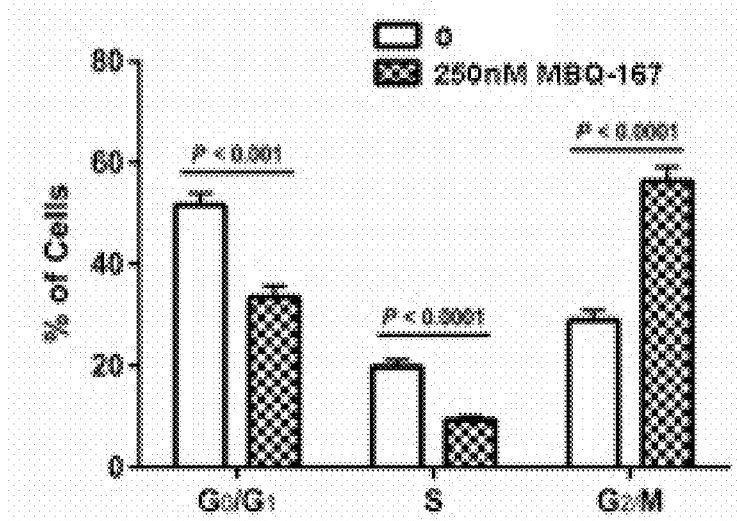

FIG. 5A shows a MTT assay following MBQ-167 treatment for 120 h for the metastatic cancer cells MDA-MB-231 and GFP-HER2-BM and the non-cancer mammary epithelial cells MCF10A, when we obtained ~100% cell death for all cell types at high concentrations (1000 nM) of MBQ-167. This assay includes both detached and attached cells in the case of the metastatic cancer cells. MBQ-167 at 120 h decreased the viability of MDA-MB-231 and GFP-HER2-BM cells with a $GI_{50}$ of 110 nM and 150 nM respectively. However, the $GI_{50}$ for the MCF10A epithelial cells at 350 nM MBQ-167 was ~3× higher (FIG. 5A). It should be noted that MBQ-167 inhibits Rac and Cdc42 activities with $IC_{50}$s in the ~100 nM range at 24 h when the MDA-MB-231, GFP-HER2-BM, MCF-7, and MCF-10 cells are still viable. Next, whether the effect of MBQ-167 on cell viability is due to cell cycle arrest by flow cytometry was determined. As shown in FIG. 5B-1, 5B-2, MBQ-167 significantly arrested the cell cycle of MDA-MB-231 cells in the G2/M phase.

Figures 1, 5C:
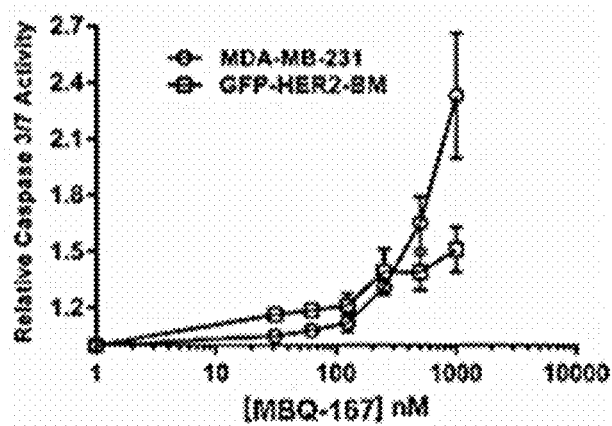
Figures 2, 5C:
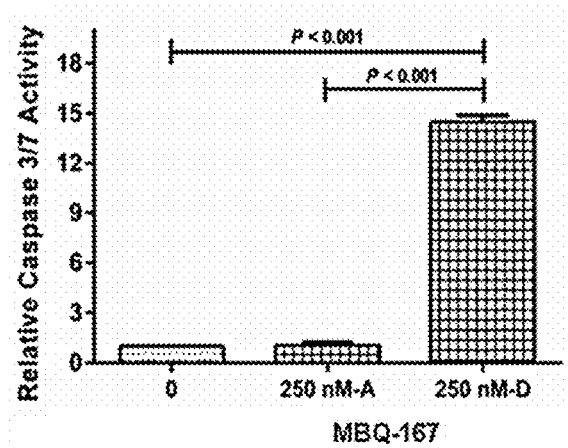
Figures 1, 5D:
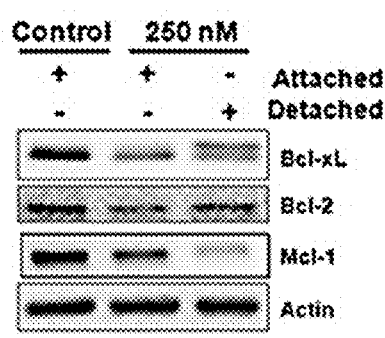
Figures 2, 5D:
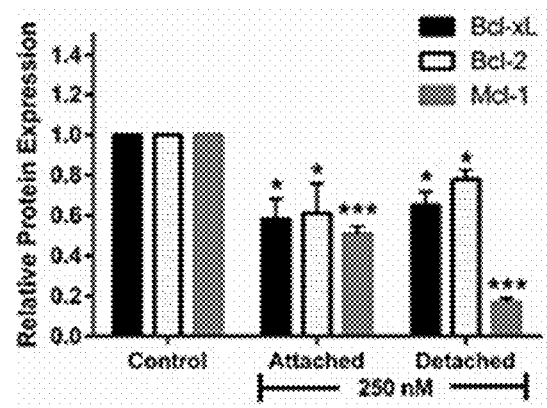
Figure 14:
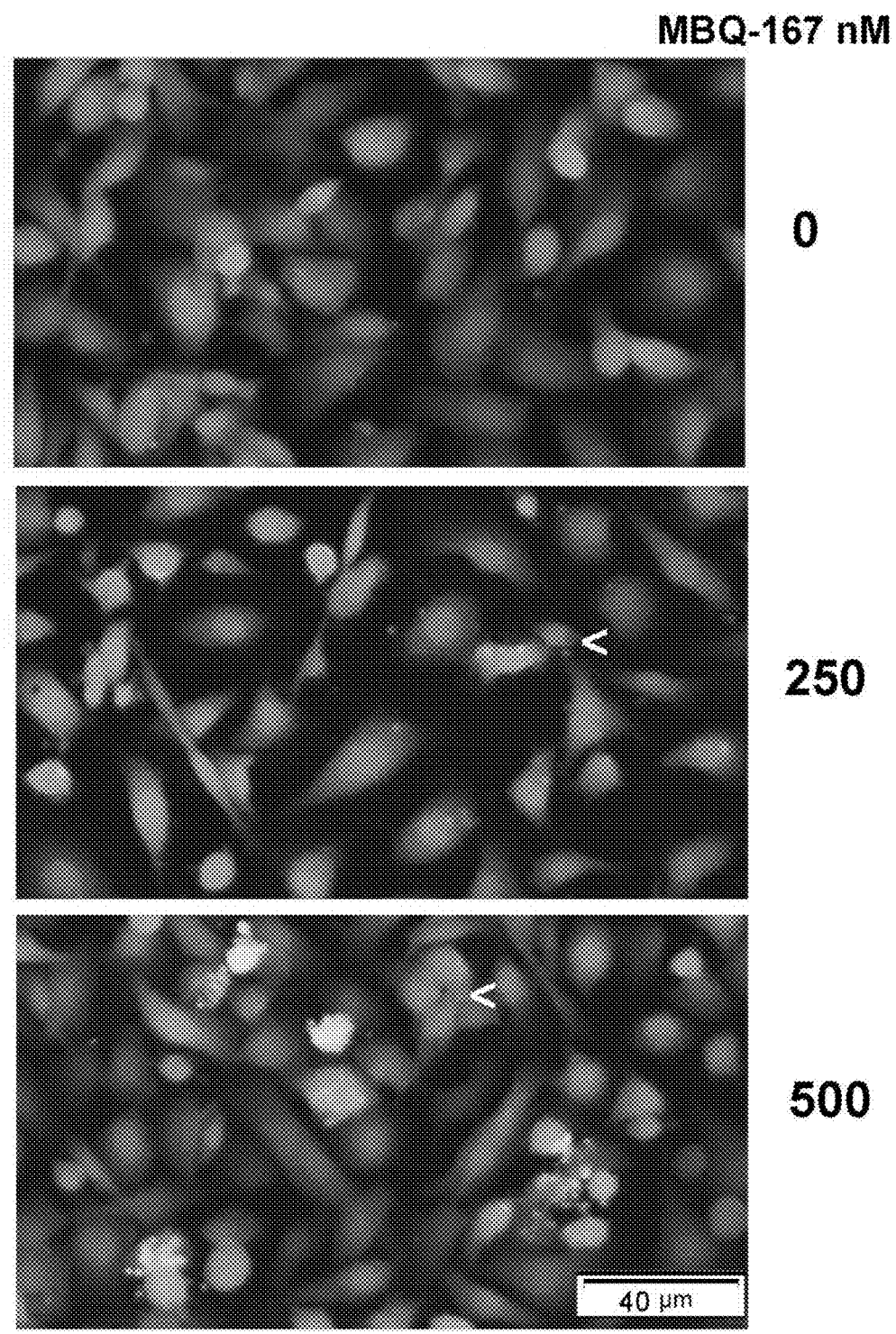
FIG. 14. Annexin V staining in response to MBQ-167. GFP-MDA-MB-231 cells growing on coverslips were treated with vehicle or MBQ-167 at 250 or 500 nM for 6 h; Cells were fixed in formaldehyde and stained with Annexin V-Cy3-18; Representative fluorescence micrographs are shown; Arrows indicate red fluorescent Annexin V staining at the membranes of apoptotic cells.
Figure 15A:
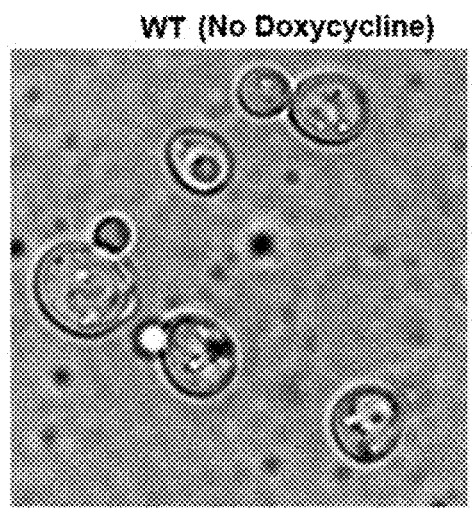
FIGS. 15A, 15B, 15C, 15D. Effect of MBQ-167 on bud polarity in *Saccharomyces cerevisiae*. A haploid derivative of the yeast strain BY4741 expressing the tTA transactivator, under the control of the CMV promoter, was used to integrate into the Cdc42 promoter to conditionally knockout the essential Cdc42 gene expression.
Figure 15B:
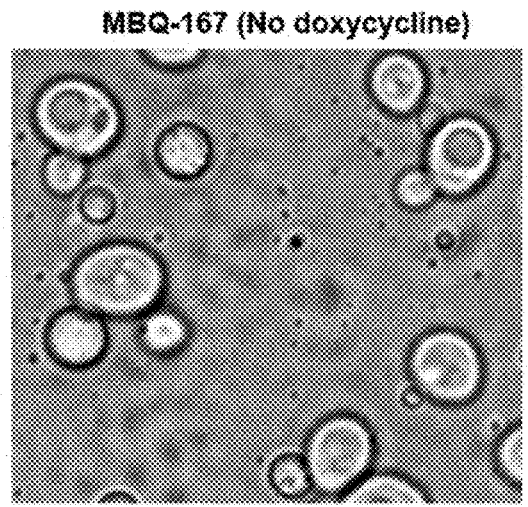
Figure 15C:
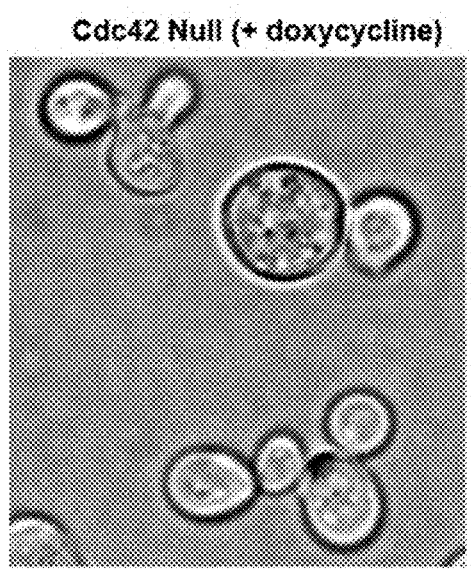
Figure 15D:
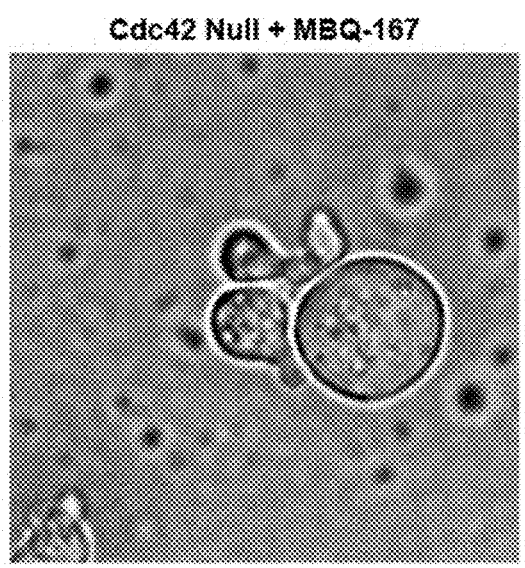

To evaluate whether the cell cycle arrest was accompanied by an increase in apoptosis, the activity of the effector caspases3/7 in whole cell populations (both attached and detached). A dose-dependent increase was observed for caspase-3/7 activity in both MDA-MB-231 and GFP-HER2-BM cell lines after 24 h in MBQ-167 (FIG. 5C-1, 5C-2). To determine whether MBQ-167 induces anoikis, the relative levels of caspase-3/7 activities were analyzed in the attached and detached MDA-MB-231 cell populations following 24 h at 250 nM MBQ-167. There was significant ~15-fold increase in caspase-3/7 activity in the detached population compared to the attached population of MDA-MB-231 cells (FIG. 5C-1, 5C-2), the effect of MBQ-167 on apoptosis was validated by showing increased Annexin V staining in MDA-MB-231 cells following 250 or 500 nM MBQ-167 (FIG. 14). In 500 nM MBQ-167, cells also demonstrated the classic blebbing associated with apoptosis. Finally, to explore the effect of MBQ-167 on mitochondrial apoptosis, the expression of the pro-survival proteins Bcl-2, Bcl-xL, and Mcl-1 was examined by western blotting. A significant decrease was found in the expression of pro-survival proteins after 24 h with 250 nM MBQ-167 (FIG. 5D-1, D-2).

Figures 1, 6A:
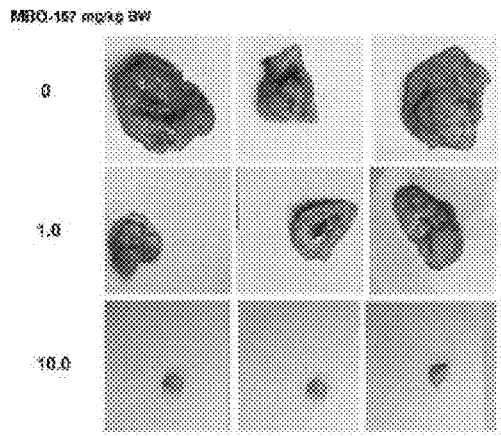
Figures 2, 6A:
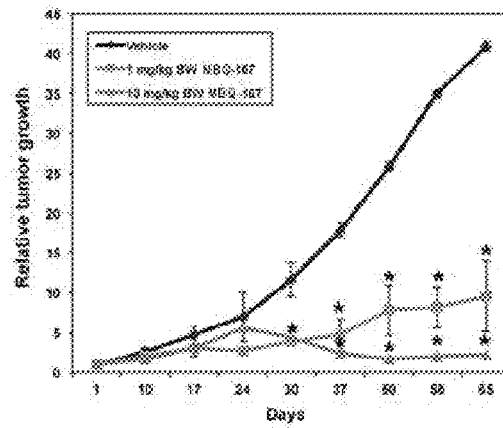

MBQ-167 Inhibits Mammary Tumor Progression of HER2 Type Breast Cancer in Immunocompromised Mice To test the effect of MBQ-167 on mammary tumor progression, nude mice were used to establish mammary fatpad tumors from GFP-HER2-BM cells. One week following mammary tumor establishment, the mice were treated 3× a week with 0, 1, or 10 mg/kg BW MBQ-167 by i.p. for 65 days. The vehicle treated mice demonstrated a linear increase in tumor growth, while MBQ-167-treated mice demonstrated a statistically significant reduction in tumor growth (FIG. 6A-1, A-2). At sacrifice, 1.0 mg/kg BW of MBQ-167 resulted in a ~80% reduction in tumor growth, and the 10 mg/kg BW MBQ-167 treatment resulted in ~95% reduction in tumor growth. Since EHop-016 only exerts ~40% reduction of tumor growth at 10 mg/kg BW, MBQ-167 is 10× more effective than EHop-016 (FIG. 6A-1, A-2).

The optimal % change in tumor size, which takes into account the individual tumor growth for each treatment, showed that the tumors from mice treated with 1 mg/kg BW MBQ-167 demonstrated a 58% growth change compared to controls (100%), while tumors from mice treated with 10 mg/kg BW MBQ-167 demonstrated only a 9% increase in tumor size (Suppl. Table 3). These data indicate that even though there was no tumor regression during the time of study, there was a drastic reduction in tumor growth in the 10 mg/kg BW MBQ-167 treated mice.

Figure 6B:
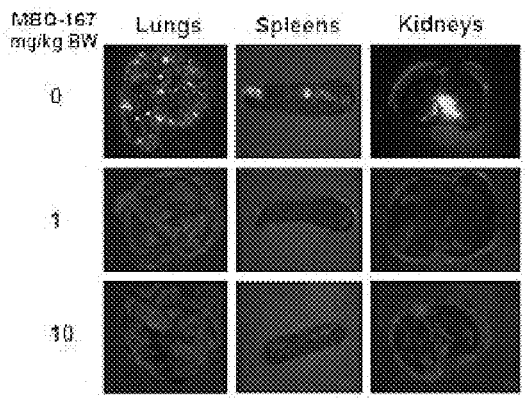

When the tumor growth delay was quantified, the control mice doubled in 8 days, and the MBQ-167 treated mice demonstrated similar doubling times for both treatments (10 and 11 days). However, at the second doubling ($2^2$), there was a delay in tumor growth of the MBQ-167 treated mice, where the tumors from control treated mice reached 22 in 14.5 days, while the tumors from 1 and 10 mg/kg BW treated mice were similar to each other by reaching $2^2$ in 30 days. By the $3^{rd}$ doubling, there was also a disparity between the two MBQ-167 treatments, where the tumors from control mice reached $2^3$ in 27 days, the 1 mg/kg BW MBQ-167 treated tumors took 57 days to reach the same size, and the 10 mg/kg BW treated tumors never reached $2^3$ in tumor growth. Similarly, only the control tumors reached $2^4$ in 33 days, while the tumors from both MBQ-167 treated (1 and 10 mg/kg BW) mice never reached this size. This result demonstrates a significant inhibition in tumor growth initiated after 24 days of MBQ-167 treatment (FIG. 6A-1, A-2). This drastic reduction in tumor growth following MBQ-167 treatment resulted in no metastases to all of the organs tested (FIG. 6B).

MBQ-167 Inhibits Mammary Tumor Progression of Triple Negative Breast Cancer in Immunocompromised Mice.

Figure 16:
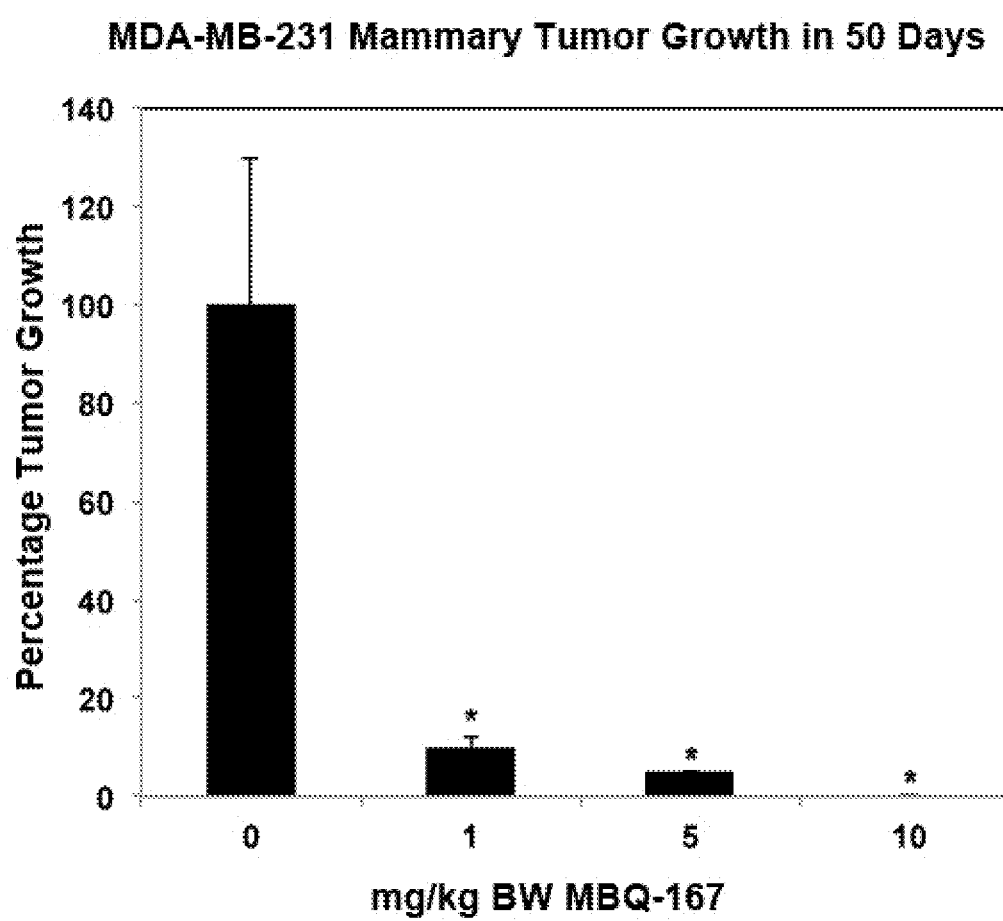
FIG. 16. In vivo efficacy of MBQ-167 in triple negative breast cancer. Mammary fat pad tumors were established in severe combined immunodeficiency (SCID) mice using green fluorescent protein (GFP) tagged-MDA-MB-231 breast cancer cells; One week later, mice were treated with 0, 1.0, 5.0, or 10.0 mg/kg body weight (BW) MBQ-167 by intraperitoneal injections 3× a week for 50 days; Mammary tumor growth was quantified from GFP image analysis; Results show average tumor growth in 50 days as a function of the size of each tumor on day 01; Vehicle control (0 mg/kg BW MBQ-167) is represented as 100% tumor growth; Administration of 1.0 mg/kg BW of MBQ-167 resulted in a 90% inhibition of tumor growth, 5.0 mg/kg BW treatment resulted in a 95% inhibition of tumor growth and the 10 mg/kg BW MBQ-167 treatment resulted in 100% inhibition of tumor growth in 50 days.

Mammary fat pad tumors were established in severe combined immunodeficiency (SCID) mice using green fluorescent protein (GFP) tagged-MDA-MB-231 breast cancer cells. One week later, mice were treated with 0, 1.0, 5.0, or 10.0 mg/kg body weight (BW) MBQ-167 by intraperitoneal injections 3× a week for 50 days. Mammary tumor growth was quantified from GFP image analysis. Results show average tumor growth in 50 days as a function of the size of each tumor on day 01. Vehicle control (0 mg/kg BW MBQ-167) is represented as 100% tumor growth. Administration of 1.0 mg/kg BW of MBQ-167 resulted in a 90% inhibition of tumor growth, 5.0 mg/kg BW treatment resulted in a 95% inhibition of tumor growth and the 10 mg/kg BW MBQ-167 treatment resulted in 100% inhibition of tumor growth in 50 days (FIG. 16).

MBQ-167 is not Toxic to Immunocompromised Mice

Figure 6C:
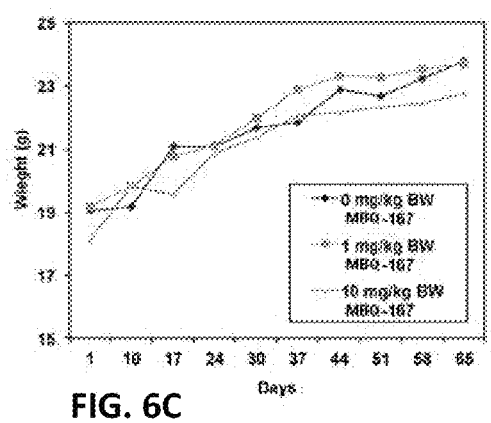
Figure 6D:
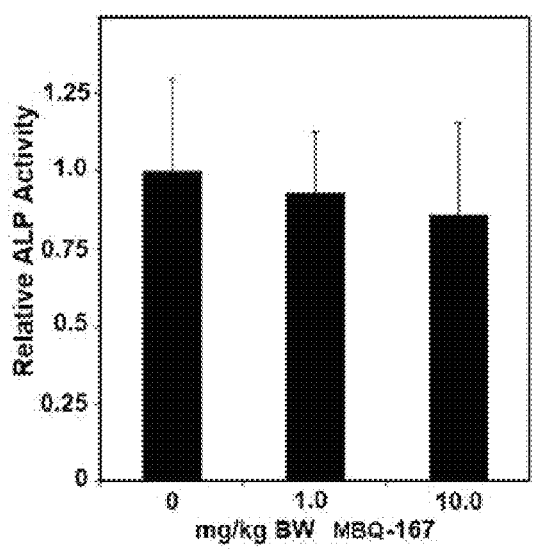
Figure 6E:
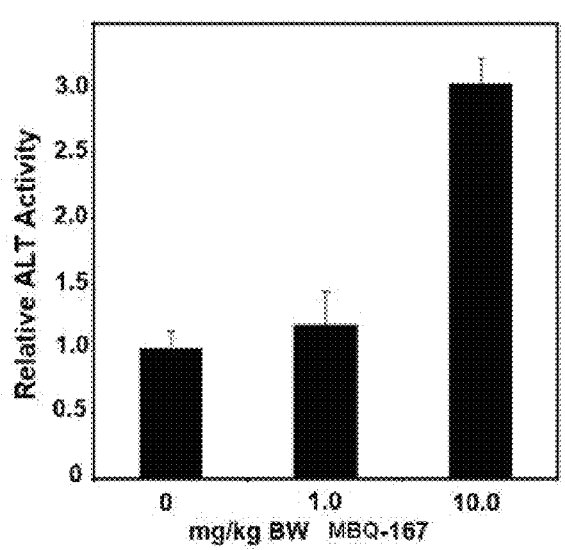

The mice from this study were also examined once a week for potential toxicity. The mice treated with vehicle or MBQ-167 did not show any significant weight loss or phenotypic changes during the 65-day study (FIG. 6C). At necropsy, livers were harvested, lysed and subjected to liver enzyme assays as a test for potential toxic effects. FIG. 6D shows that MBQ-167 does not affect ALP activity in the livers of MBQ-167 treated nude mice (1 and 10 mg/kg BW). However, the liver ALT levels were significantly increased by 10 mg/kg BW MBQ-167 treatment, indicating a potential metabolism of MBQ-167 at higher concentrations (FIG. 6E).

Molecules which function as inhibitors of the Ras-homologous (Rho) family of small GTPases (e.g. Rac and Cdc42) and their use to treat cancers including breast, pancreatic, ovarian, prostate, gastric, and neuroblastoma, where these GTPases are overexpressed or hyperactivated, and diseases where activation of Rho GTPases plays a pivotal role are mediated through these proteins.

A compound according to general formula I

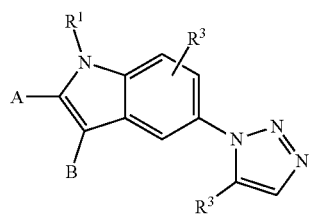

Wherein:
R1 is hydrogen, C1-6 alkyl, or C3-6 cycloalkyl.
$R^2$ is independently in each occurrence hydrogen, halide, hydroxyl, cyano, C1-6 alkyl, C3-6 cycloalkyl, C1-6 haloalkyl, nitro, amino, etc.
$R^3$ is aryl, heteroaryl, indol-5-yl, benzimidazol-5-yl, indazol-5-yl, C1-6 alkyl, $C_{2-6}$.
hydroxyalkyl, $C_{3-6}$ cycloalkyl, or $R^a$, $R^bN[CR^4]2-6$.
$R^a$ and $R^b$ are independently hydrogen, $C_{1-6}$ alkyl, or $C_{3-6}$ cycloalkyl
$R^4$ is independently in each occurrence hydrogen or $C_{1-6}$ alkyl.

A and B are independently hydrogen, halide, hydroxyl, cyano, C1-6 alkyl, C3-6 cycloalkyl, C1-6 haloalkyl, nitro, amino, etc.

In the compound of general formula 1, where A and B form a ring system:

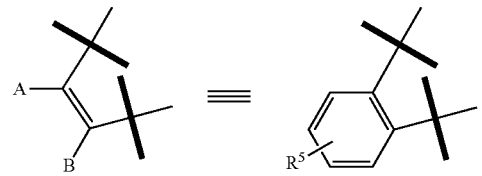

Wherein:
$R^5$ is independently in each occurrence hydrogen, halide, hydroxyl, cyano, C1-6 alkyl, C3-6 cycloalkyl, C1-6 haloalkyl, nitro, amino.

A method of inhibiting Rac and/or Cdc42 in a cell includes contacting the cell with a compound of general formula 1.

A method of treating a patient with cancer or hyperproliferative disorders is by administering to the patient a compound of general formula 1.

The cancer or hyperproliferative disorders include breast cancer, prostate cancer, neuroblastoma, ovarian cancer, pancreatic cancer, or gastric cancer.

The biochemical characterization of MBQ-167, which inhibits Rac and Cdc42 activation. Rac and Cdc42 are pivotal signaling intermediates whose dysregulation has been implicated in oncogenic transformation, cancer progression, metastasis, and multiple diseases. Recent studies, including the inventors' own, have shown that targeting Rac and Cdc42 has potential for metastatic cancer therapy. However, the current small molecule inhibitors of Rac and Cdc42 are only effective at micromolar concentrations.

To develop a new, more potent inhibitor of Rac and Cdc42 with an $IC_{50}<1.0$ μM, the novel derivative MBQ-167 shows improved efficacy in metastatic breast cancer cells by inhibiting Rac activity with an $IC_{50}$ of ~103 nM, and Cdc42 with an $IC_{50}$ of 78 nM. This concentration dependent response of breast cancer cells to MBQ-167 demonstrates that MBQ-167 is specifically inhibiting the biochemical activation of the Rac and Cdc42. However, MBQ-167 did not inhibit the Rac activity of cells expressing dominant active Rac1(G12V) indicating that MBQ-167 is specifically inhibiting Rac1 activation. Moreover, our data show that MBQ-167 does not affect the activation of the related GTPase Rho. Therefore, we expect this new molecule to be useful as a tool for probing Rac and Cdc42 function in responsive cell types.

MBQ-167 was an effective inhibitor of the Rac and Cdc42 downstream effector PAK. Interestingly, MBQ-167 induced an increased autophosphorylation of S144 (PAK1), the activation of which is not essential, but contributes to the activity of the PAK kinase domain. This result may be due to a feedback mechanism compensating for Rac/Cdc42 inhibition. Nevertheless, phosphorylations in the PAK kinase domains, as well as the PAK effectors LIMK and cofilin, a potent regulator of actin filament dynamics during cell migration, were significantly inhibited by MBQ-167. Therefore, we conclude that overall, MBQ-167 inhibits PAK activity, contributing to a reduction in actin cytoskeletal extensions and cell migration. Since Rac and Cdc42 also regulate Wiskott Aldrich Syndrome protein (WASP)-family members that contribute to actin dynamics, MBQ-167 may exert additional inhibitory effects on the cytoskeleton.

Furthermore, Cdc42 regulates cell polarity through the polarity protein portioning defective proteins (PAR6, 3), which stabilize microtubules during directed migration. Using a haploid derivative of the yeast strain BY4741, where the essential gene Cdc42 was knocked out conditionally via a tetracycline inducible promoter, MBQ-167 exerts a similar phenotype to the cells with reduced Cdc42 expression. Cdc42 knockdown abolishes cell polarity where the yeast buds (daughter cells) are not aligned symmetrically with the mother cells. A similar non-polar effect was also observed on yeast cell budding in the presence of MBQ-167. This mutant phenotype was more pronounced in the yeast cells with both Cdc42 knockdown and MBQ-167 treatment demonstrating that MBQ-167 may inhibit the highly conserved yeast Cdc42 to regulate cell polarity. As expected, MBQ-167 treatment also enhanced the growth inhibitory effects of Cdc42 knockdown.

The regulation of microtubule dynamics by Rac and Cdc42 activities are also critical for cell cycle progression, where Cdc42, and thus PAK, controls mitotic spindle formation and cell cycle progression in $G_2/M$. Therefore, the observed MBQ-167-mediated metastatic breast cancer cell cycle arrest in the $G_2/M$ phase may be a consequence of Rac/Cdc42/PAK inhibition by MBQ-167.

The decreased Rac/Cdc42/PAK activities, cell viability, loss of cell polarity, and detachment from the substratum in response to MBQ-167 is limited to cancer cells that have undergone epithelial to mesenchymal transition (EMT) but not to epithelial cancer or non-cancer cells. This selective response to MBQ-167 may be due to the differential expression and activities of Rac and Cdc42 GEFs in different breast cancer cell lines, where only a subset of the ~80 known Rac and Cdc42 GEFs are expected to be expressed and activated in the metastatic breast cancer cell lines that were investigated. Moreover, the currently available Rac/Cdc42 inhibitors also inhibit only a subset of Rac/Cdc42 GEFs. For instance NSC23766 inhibits only Tiam-1/and Trio activation of Rac, while EHop-016 is a specific inhibitor of the Vav/Rac interaction. Therefore, MBQ-167 may inhibit only a subset of Rac/Cdc42 GEFs that are preferentially expressed/activated in the more metastatic mesenchymal-like cancer cells lines.

Additionally, the relative insensitivity of epithelial-like cells to MBQ-167 may be because the hemidesmosomes in epithelial cells are primarily regulated by a6(4-integrin mediated attachments to the intermediate filament cytoskeleton, which are not directly regulated by Rac and Cdc42. In contrast, the focal adhesions in mesenchymal cells, which are regulated by multiple integrin sub units to form attachments with the actin cytoskeleton, are under Rac/Cdc42/PAK regulation. Therefore, the observed reduction and reorganization of focal adhesions in MBQ-167 treated cancer cells may reflect inhibition of the Rac/Cdc42/PAK regulated integrin-mediated focal adhesion assembly at the cell leading edge.

Focal adhesions are not only important for directed migration, disruptions in proper regulation of cell adhesion to the ECM can result in anoikis, apoptosis induced by inadequate or inappropriate cell-matrix interactions. In this context, Rac 1 has been shown to confer anoikis resistance. Data disclosed with caspase assays and reduction in pro-survival BC12-homology proteins validate the hypothesis that MBQ-167 acts as an anticancer agent by inducing anoikis. Data show that only the detached breast cancer cells respond to MBQ-167 increased caspase3/7 activities, indicating that cell detachment precedes apoptosis signaling, as would be predicted during anoikis. Moreover, MBQ-167 selectively decreases the viability of cancer cell lines that have undergone EMT, without affecting the non-cancer cell line MCF10A. This cell line specificity could be due to differences in the dependence on Rac/Cdc42/PAK signaling and the accompanying integrin engagement and focal adhesion assembly, in the more migratory mesenchymal cells compared to the epithelial cells. In addition, MBQ-167 may have similar effects in multiple other cancers, including a number of ovarian, gastric, pancreatic, and neuroblastoma cell lines that have undergone EMT. Since EMT is associated with more stem cell-like properties, therapy resistance, and disease recurrence, MBQ-167 has potential to reduce therapy resistance. Moreover, the fact that MBQ-167 is effective against the KRAS mutant MIA PaCa-2 cell line demonstrates its ability to target oncogenic RAS dependent cancers.

MBQ-167 also inhibits STAT3 phosphorylation, a Rac-regulated transcription factor shown to be active in several cancers. Since STAT3 activity increases the expression of several genes involved in cell cycle progression, its decrease in activity may contribute to the observed cell cycle arrest by MBQ-167 treatment. Importantly, STAT3 transcriptionally regulates all three of the pro-survival $BC_{1-2}$ family genes analyzed in this study. Furthermore, several reports show that cancer stem cell like properties are dependent on STAT3 activity. Accordingly, MBQ-167 decreases the mammosphere forming efficiency of MDA-MB-231 cells by ~50%. These results suggest that MBQ-167 may be further effective as an anti-cancer therapeutic by targeting cancer stem cell like populations, perhaps specifically inhibits cancer stem cell activity.

Finally, MBQ-167 reduces mammary fat pad tumor size starting as early as 3 wks following treatment, with a 91% reduction by 2 months at a non-toxic concentration of 10 mg/kg BW. The drastic reduction in mammary tumors also resulted in a 100% inhibition of metastases to all organs tested, probably because less cells were shed by the small tumors. As evidenced by the in vitro data, the reduced tumor size in response to MBQ-167 treatment is predicted to be due to inhibition of Rac/Cdc42/PAK signaling ultimately leading to a loss in cell viability, growth, and polarity causing the cells to detach from the tumor and undergo anoikis. Since we did not observe any metastases in mice treated with MBQ-167, any cells detached from the primary tumor probably go through anoikis, and do not survive in the circulation.

Similarly, in severe combined immunodeficiency (SCID) mice with MDA-MB-231 mammary tumors, MBQ-167 inhibited tumor growth by 90%, 95%, and 100% at doses of 1, 5, and 10 mg/kg BW, respectively (FIG. 16).

Taken together, MBQ-167 is an effective Cdc42 and Rac inhibitor that significantly decreases downstream signaling and cancer promoting cell functions to ultimately reduce mammary tumor growth with 10× more potency than the first described Rac inhibitor EHop-016. However, the effects of MBQ-167 on the metastatic cancer cell phenotype, where the cells detach from the substratum to ultimately undergo apoptosis by anoikis mechanisms, may be due to additional effects of MBQ-167 on integrin signaling or alternate mechanisms. Nevertheless, the dramatic effect of MBQ-167 on mouse mammary tumor growth warrants further development of MBQ-167 as an anticancer therapeutic.

EXAMPLES

MBQ-167 (9-Ethyl-3-(5-phenyl-[1,2,3]triazol-1-yl)-9H-carbazole) Data

FIG. 1. Freshly prepared 3-azido-9-ethylcarbazole was reacted with magnesium phenylacetylide to generate the 4-halomagnesiotriazole intermediate, that was quenched with 10% ammonium chloride to furnish 9-Ethyl-3-(5-phenyl-[1,2,3]triazol-1-yl)-9H-carbazole (MBQ-167) in 86% yield.

FIG. 2A; FIG. 2B. MBQ-167 affects metastatic cancer cell polarity without affecting non-metastatic cancer cells. At ≥100 nM, starting at six hours MBQ-167 induces a loss of polarity and detachment from the substratum in MDA-MB-231 metastatic breast cancer cells but not in MCF-7 non-metastatic human breast cancer cells. 250 nM MBQ-167 results in ~70% of the cells losing polarity and assuming a rounded phenotype. Higher concentrations of MBQ-167, i.e. 500 nM for 24 h results in a ~90% loss in cell polarity and detaches from the substratum.

FIG. 2A; FIG. 9. This dramatic rounding and detachment in response to MBQ-167 is demonstrated by HER2 type and triple negative breast cancer (TNBC) mesenchymal breast cancer cells (MDA-MB-231, Hs578t, MDA-MB-468, and HER2-BM), as well as other metastatic cancer cell lines: Mia-PaCa-2 pancreatic cancer (with G12C kRas mutation), SKOV3 ovarian cancer, NCI-N87 gastric cancer, and SH-SY5Y neuroblastoma. This effect was less in the more epithelial MCF-10A and MCF-7 breast cancer cells and AGS primary gastric cancer cells.

FIG. 15A, 15B, 15C, 15D. In *Saccharomyces cerevisiae* (budding yeast) that only expresses Cdc42, which regulates polarity and cell division, treatment with 100 microM MBQ-167 inhibited yeast bud polarity and growth, suggesting that the effect on cell polarity may be via inhibition of Cdc42 by MBQ-167.

FIG. 2B. Staining for F-actin by Rhodamine phalloidin shows a loss of invadopodia and filopodia, F-actin based motile structures regulated by Rac and Cdc42, in response to MBQ-167.

FIGS. 2B, 2C. Immunostaining with an anti phosphotyrosine or vinculin antibody, for focal adhesions that are formed by the engagement of integrin receptors with the ECM, demonstrate a dramatic rearrangement of focal adhesions during cell rounding, where the focal adhesions moved from the cell edge to the cell center and appear more disorganized.

FIG. 3A-1, 3A-2, 3B-1, 3B-2, 3C, 3D. MBQ-167 inhibits Rac 1/2/3 activity in the MDA-MB-231 human metastatic breast cancer cell line with an IC50 of 103 nM, and Cdc42 activity with an IC50 of 78 nM.

Table 1. At 250 nM MBQ-167 inhibits the Rac and Cdc42 activities of MDA-MB-231 cells without affecting the activity of the close isoform Rho.

Figure 10C:
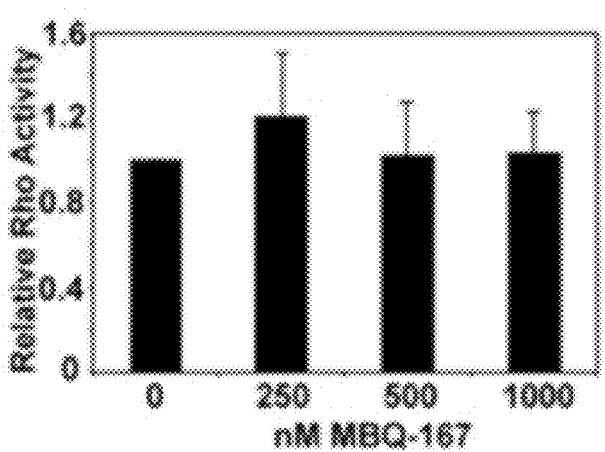

FIG. 10A, 10B, 10C. MBQ-167 also inhibits the Rac and Cdc42 activities of GFP-HER2-BM human metastatic breast cancer cells. MBQ-167 does not affect the activity of Rho.

Table 2. MBQ-167 (250 nM) does not affect the Rac activity of MCF-7, a non-metastatic human breast cancer cell line.

FIG. 7. MBQ-167 also does not inhibit the Rac activity of a constitutively active metastatic cancer cell line (MDA-MB-435-Rac1G12V) indicating that MBQ-167 is inhibiting the loading of GTP to Rac.

FIG. 3A-1, A-2, B-1, B-2, C, D, FIG. 10A, 10B, 10C. In MDA-MB-231 and GFP-HER2-BM metastatic breast cancer cells, Rac, Cdc42, and the Rac and Cdc42 downstream effector p21-activated kinase PAK activities were reduced by 75, 85, and 90% respectively, in the detached cells compared to vehicle controls, while these activities were less reduced (~25%) in the attached population.

FIG. 8A, 8B. In NCI-N87 gastric cancer cells, MBQ-167 significantly decreases the activity (but not expression) of the Rac and Cdc42 downstream effector p21-activated kinase (PAK 1, 2, 4), as demonstrated by western blotting with antibodies to total and active phospho residues.

FIG. 11. MBQ-167 does not inhibit PAK activities of MCF-7 primary breast cancer cell line.

Figure 4B:
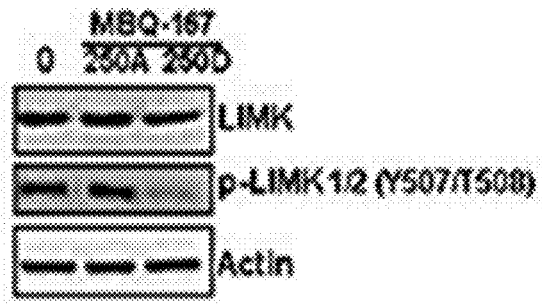
Figure 4C:
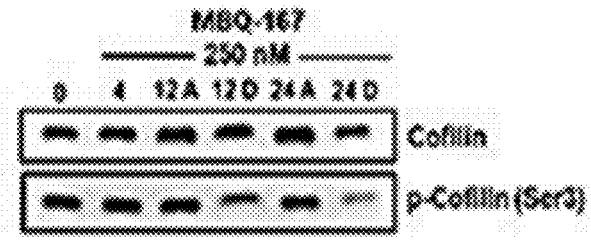

FIGS. 4B, 4C. In MDA-MB-231 cells, 250 nM MBQ-167 inhibits downstream PAK signaling as evidenced by western blotting for the activating phosphorylation (Y507/T508) of the direct PAK substrate LIM kinase (LIMK) and the inactivating phosphorylation (S3) of the LIMK substrate cofilin (actin depolymerization factor).

Figures 1, 4D:
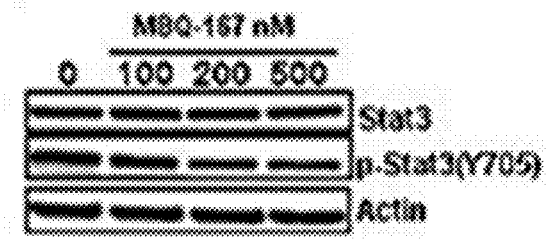
Figures 2, 4D:
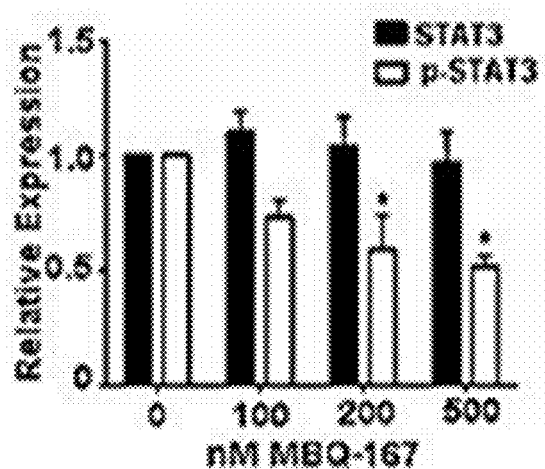
Figures 1, 4E:
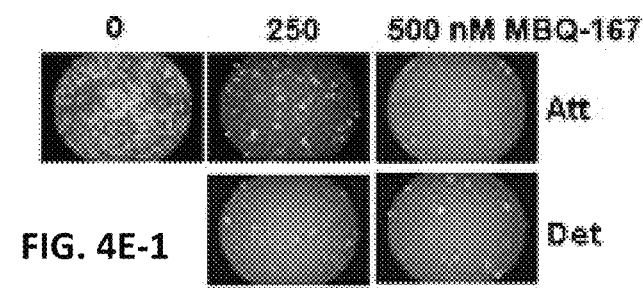
Figures 2, 4E:
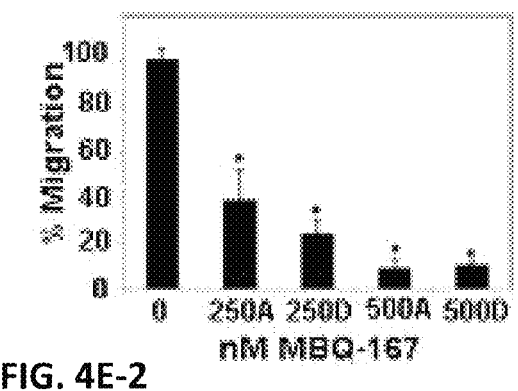
Figure 4F:
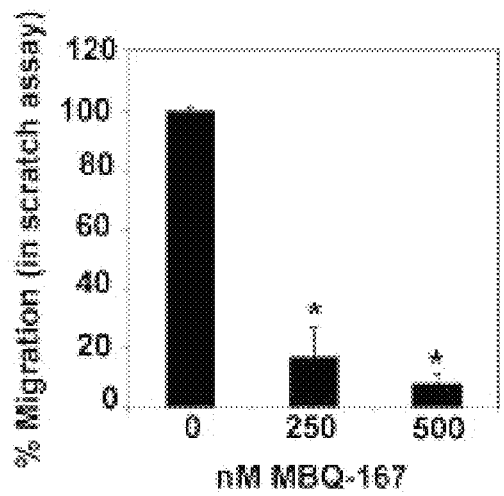
Figure 12A:
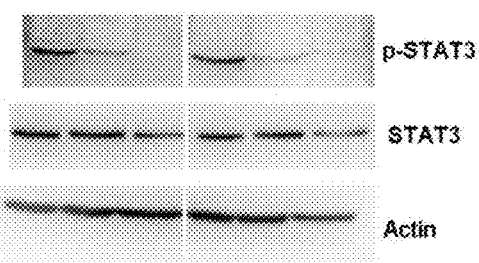
FIGS. 12A, 12B. Effect of MBQ-167 on STAT3 activation and cell migration in GFP-HER2-BM metastatic cancer cells.
Figure 13A:
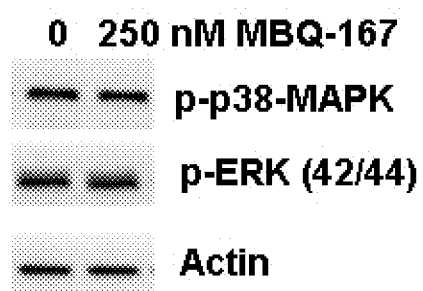
FIGS. 13A, 13B. MAPK and Akt signaling in MDA-MB-231 cells. MDA-MB-231 cells were treated with 250 nM MBQ-167 for 24 h and equal amounts of protein from attached and detached cell lysates were western blotted for FIG. 13A, phospho (active) p-38 and p-42/44 (ERK) MAPKs or FIG. 13B, total and phospho (s-473) Akt. Representative western blots of N=3 are shown.
Figure 13B:
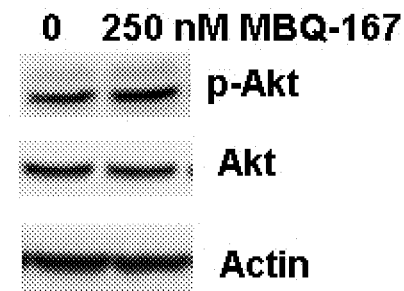

FIG. 4D-1, D-2, FIG. 12A. In MDA-MB-231 and GFP-HER2-BM cells, MBQ-167 reduces the activity of signal transducer and activator of transcription (STAT3). However, MBQ-167 does not affect the p42/44 mitogen activated kinase (MAPK), p38-MAPK, or Akt activities of MDA-MB-231 cells.

Figure 12B:
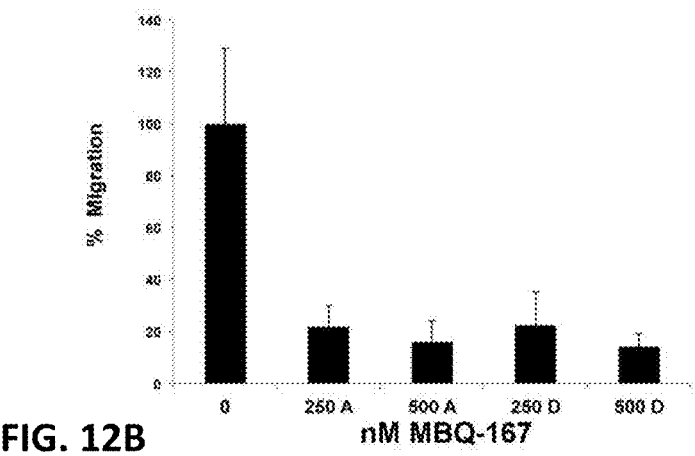

FIG. 4-1, 4E-2, 4F; FIG. 12B. MBQ-167 mediated inhibition of Rac/Cdc42 signaling results in 80-90% inhibition of MDA-MB-231 and GFP-HER2-BM cell migration as shown by Transwell and wound healing assays.

Figure 4G:
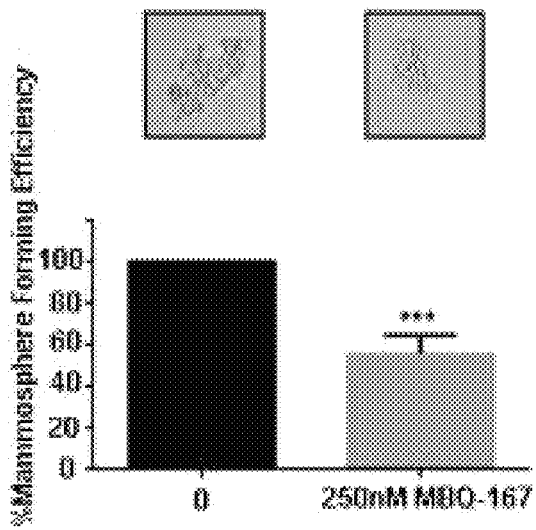

FIG. 4G. The mammosphere forming efficiency of MDA-MB-231 cells is significantly reduced by ~50%, following a 4-day treatment with MBQ-167.

FIG. 5A. MDA-MB-231 and GFP-HER2-BM metastatic breast cancer cells incubated in 1000 nM MBQ-167 for 120 h undergoes ~100% cell death with a $GI_{50}$ of 110 nM for MDA-MB-231 cells and a $GI_{50}$ of 150 nM for GFP-HER2-BM cells. MBQ-167 also does not affect the viability of MCF7 non-metastatic breast cancer cells or MCF-10A mammary epithelial cells at these concentrations. The $GI_{50}$ for the MCF10A epithelial cells at 350 nM MBQ-167 is ~3× higher than that for the metastatic breast cancer cells.

FIG. 8A. NCI-N87 viability. 250 nM MBQ-167 reduced the viability of NCI-N87 cells by 55%, as analyzed from a MTT assay.

FIG. 5B-1, 5B-2. MBQ-167 treatment for 24 h to combined attached and detached MDA-MB-231 cells results in a $G_2$/M phase arrest.

FIG. 5C-1, 5C-2; FIG. 14. The detached MDA-MB-231 breast cancer cells respond to MBQ-167 by increased caspase 3/7 activities. The attached cells initiate apoptosis in response to 250-500 nM MBQ-167 at 6 h as shown by Annexin V staining.

FIG. 5D. MBQ-167 treatment of MDA-MB-231 cells for 24 h results in reduced expression of the mitochondrial pro-survival proteins of the Bcl-2 family (Bcl-2, Bcl-XL, and MCl-1).

FIG. 6A-1, 6A-2, 6B. Tables 3, 4. In nude mice with mammary fat pad tumors established with GFP-HER2-BM cells, 1.0 mg/kg BW of MBQ-167 results in a ~80% reduction in tumor growth, and the 10 mg/kg BW MBQ-167 treatment results in ~95% reduction in tumor growth in 65 days. Data indicates a drastic reduction in tumor growth in the 10 mg/kg BW MBQ-167 treated mice, with a significant inhibition in tumor growth initiated after 24 days of 1 or 10 mg/kg BW MBQ-167 treatment.

FIG. 16. MB-231 Mammary Tumor Growth. In severe combined immunodeficiency (SCID) mice bearing GFP-MDA-MB-231 mammary fat pad tumors, 1.0 mg/kg BW of MBQ-167 resulted in a 90% inhibition of tumor growth, 5.0 mg/kg BW treatment resulted in a 95% inhibition of tumor growth and the 10 mg/kg BW MBQ-167 treatment resulted in 100% inhibition of tumor growth in 50 days.

FIG. 6B. Due to this drastic reduction in tumor growth, MBQ-167 inhibits metastasis, to all of the organs tested (lungs, bone, heart, spleen, kidney, livers), by 100%.

FIG. 6C. MBQ-167 does not exert toxic effects on weight or phenotype of nude or SCID immunocompromised mice.

FIG. 6D, 6E. MBQ-167 does not significantly affect liver alkaline phosphatase (ALP) activity but increases liver alanine transaminase (ALT) activity.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthylenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

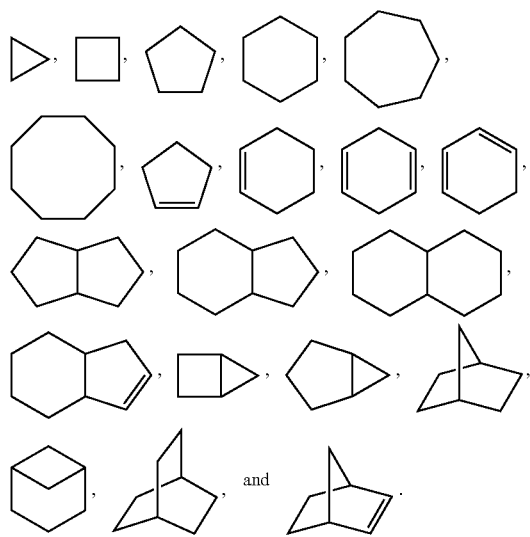

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3,4-tetrahydropyridinyl, and the like. Illustrative examples of heterocycloalkyl groups shown in graphical representations include the following entities, in the form of properly bonded moieties:

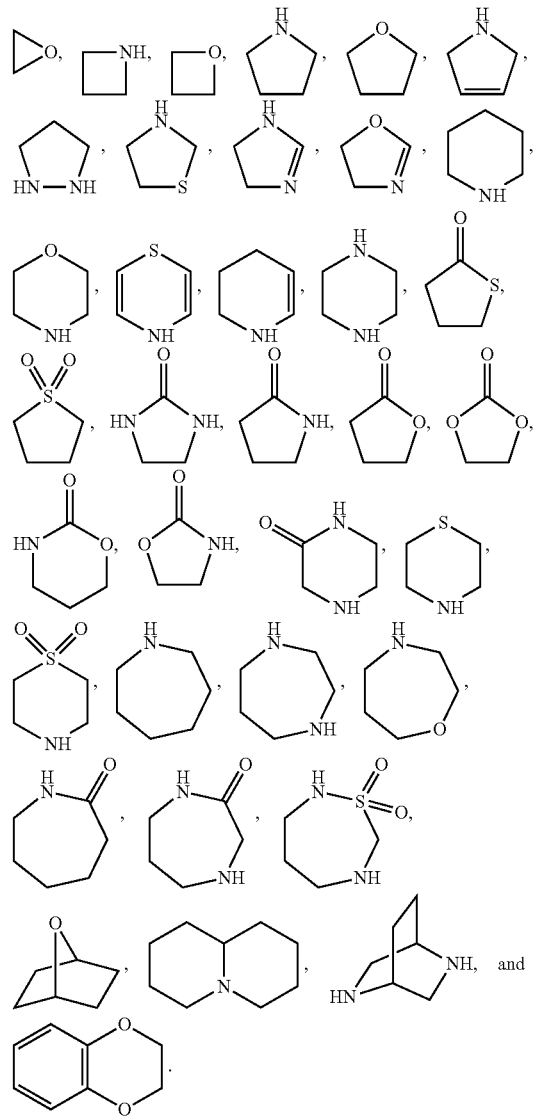

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

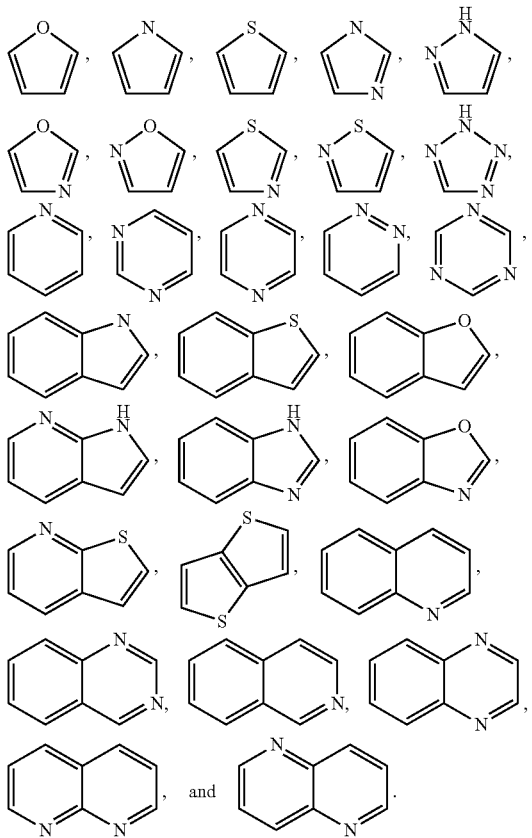

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound in accordance with the present disclosure). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol "  " include both stereoisomers for the carbon atom to which the symbol "  " is attached, specifically both the bonds "  " and "  " are encompassed by the meaning of "  ".

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

MATERIALS AND METHODS

Synthesis of MBQ-167

All reagents were purchased from Sigma-Aldrich Chemical Company. The synthesis of 3-Azido-9-ethyl-9H-carbazole 3 is as follows (FIG. 1).

Step 1

To a solution of 2.10 g (10.0 mmol) 9-Ethyl-9H-carbazol-3-yl-amine 1 in 20 mL water, 2.0 mL (40.0 mmol) of concentrated sulfuric acid ($H_2SO_4$) was added. When all the amine was converted to the sulfate (green precipitate), 10 mL more of water was added and the suspension cooled to 0-5° C. in an ice-water bath. A solution of 0.828 g (12.0 mmol) sodium nitrite (NaNO$_2$) in 5 mL of water was added dropwise, and the mixture stirred for 1 h. Next, a solution of 0.780 g (12.0 mmol) of sodium azide (NaN$_3$) in 5 mL of water was added dropwise and stirred continuously for 2-8 h. After completion of the reaction, the reaction mixture was warmed to 25° C., 30 mL of ethyl acetate and 20 mL of distilled water were added, and after vigorous mixing, the layers were separated. The organic layer was extracted with 10 mL brine, separated, dried on sodium sulfate, filtered and concentrated on a rotary evaporator. After silica gel chromatography using 3:1 hexanes/ethyl acetate as the eluent, 3-Azido-9-ethyl-9H-carbazole 3 was obtained as an off-white solid in a yield of 1.79 g (7.58 mmol=76%). The product was identified with TLC and NMR spectroscopy. R$_f$=0.82 (3:1, Hexane/Ethyl Acetate); $^1$HNMR (CDCl$_3$, 400 MHz) δ 1.43 (t, J=7.19 Hz, 3H), 4.37 (q, J=7.19 Hz, 2H), 7.14 (dd, J=2.17, 8.63 Hz, 1H), 7.24 (d, J=7.13 Hz, 1H), 7.37 (d, J=8.64 Hz, 1H), 7.41 (d, J=8.24 Hz, 1H), 7.49 (t, J=7.14 Hz, 1H), 7.75 (d, J=2.19 Hz, 1H), 8.07 (d, J=7.80 Hz, 1H); $^{13}$C (CDCl$_3$, 100 MHz) δ 14.1, 38.0, 109.0, 109.8, 110.7, 117.5, 119.3, 120.9, 122.5, 124.2, 126.6, 131.4, 137.8 140.9.

Step 2: Synthesis of 1-(9-Ethyl-9H-carbazol-3-yl)-5-phenyl-1H-1,2,3-triazole 6 (MBQ-167)

In a 25 mL 3-neck round bottom flask containing phenylacetylene 0.11 g (1.1 mmol) under a nitrogen atmosphere, a solution of ethylmagnesium bromide in THF 1.1 mL (1.1 mmol) was added dropwise at 25° C. After the Grignard reagent was added, the mixture was heated at 50° C. for 15 min and cooled to 25° C. A solution of 0.24 g (1.0 mmol) of azide 3 in THF (1.0 M) was added dropwise and heated to 50° C. for 1 h. After quenching with 10% ammonium chloride, the products were extracted with ethyl acetate (3×). The organic layer was washed with 10 mL of brine, separated and dried on sodium sulfate, filtered and concentrated on a rotary evaporator to obtain crude material (0.33 g). The crude oil was purified via silica gel chromatography to obtain 0.29 g (0.86 mmol=86%) of 1-(9-Ethyl-9H-carbazol-3-yl)-5-phenyl-1H-1,2,3-triazole MBQ-167 as a white solid. Purity (≥98%) was verified by TLC, NMR spectroscopy, and GC/MS: R$_f$=0.26 (3:1, hexane/ethyl acetate); $^1$HNMR (CDCl$_3$, 400 MHz) δ 1.47 (t, J=7.22 Hz, 3H), 4.38 (q, J=7.22 Hz, 2H), 7.26-7.33 (m, 6H), 7.36 (dt, J=1.76, 8.60 Hz, 1H), 7.41 (d, J=8.84 Hz, 1H), 7.46 (d, J=8.32 Hz, 1H), 7.53 (t, J=7.32 Hz, 1H), 7.93 (s, 1H), 8.20 (d, J=7.84 Hz, 1H), 8.15 (d, J=1.80 Hz, 1H); $^{13}$C (CDCl$_3$, 100 MHz) δ 13.8, 37.9, 108.7, 108.9, 117.9, 119.5, 120.8, 122.5, 123.0, 123.2, 126.6, 127.1, 128.3, 128.5, 128.8, 129.0, 133.1, 138.0, 139.8, 140.7. LRGC-MS m/z (rel %): [M]$^+$338 (37), [M-C$_2$H$_5$]$^+$310 (55), [M-C$_2$H$_5$N]$^+$295 (100), [M-C$_2$H$_5$N$_2$]$^+$ 281 (34), [M-C$_9$H$_9$N$_3$]$^+$ 179 (34).

9-Ethyl-3-(5-phenyl-1H-1,2,3-triazol-1-yl)-9H-carbazole (I-1)

Step 1: Synthesis of 3-Azido-9-ethyl-9H-carbazole

To a slurry of 2.10 g (10.0 mmol) 9-Ethyl-9H-carbazol-3-yl-amine in 20 mL water, 2.0 mL (40.0 mmol) of concentrated sulfuric acid (H$_2$SO$_4$) was added. When all the amine has been converted to the sulfate (green precipitate), 10 mL more of water was added and the suspension is cooled to 0-5° C. in an ice-water bath. A solution of 0.828 g (12.0 mmol) of sodium nitrite (NaNO$_2$) in 5 mL of water was added dropwise, and the mixture is stirred for 1 h. With strong stirring, a solution of 0.780 g (12.0 mmol) of sodium azide (NaN$_3$) in 5 mL of water was added dropwise and stirring is continued for 2-8 h. After the reaction mixture was warmed to room temperature, 30 mL of ethyl acetate and 20 mL of distilled water were added, and after vigorous mixing, the layers were separated with the aid of a separation funnel. The organic layer was extracted with 10 mL brine, separated and dried on sodium sulfate, filtered and concentrated on a rotary evaporator to obtain a crude brown oil. After silica gel chromatography using 3:1 hexanes/ethyl acetate as the eluent, the 3-Azido-9-ethyl-9H-carbazole 2 was obtained as a pure compound in a yield of 1.79 g (7.58 mmol=76% from crude material). The product was identified with TLC, NMR and GC/MS. R$_f$=1.00 (3:1, Hexane/Ethyl Acetate); $^1$H NMR (CDCl$_3$, 400 MHz) δ 1.43 (t, J=7.26 Hz, 3H), 4.37 (q, J=7.24 Hz, 2H), 7.14 (dd, J=2.17, 8.63 Hz, 1H), 7.24 (t, J=7.13 Hz, 1H), 7.37 (d, J=8.64 Hz, 1H), 7.41 (d, J=8.24 Hz, 1H), 7.49 (t, J=8.17 Hz, 1H), 7.75 (d, J=2.19 Hz, 1H), 8.07 (d, J=7.80 Hz, 1H); $^{13}$C (CDCl$_3$, 100 MHz) δ 13.7, 37.6, 109.2, 108.6, 109.4, 110.3, 117.1, 118.9, 120.2, 120.6, 122.1, 123.8, 126.2, 131.0, 137.5, 140.5.

Step 2: Synthesis of 1-(9-Ethyl-9H-carbazol-3-yl)-5-phenyl-1H-1,2,3-triazole (I-1)

To a 25 mL 3-neck round bottom flask containing phenylacetylene 0.11 g (1.1 mmol) under a nitrogen atmosphere, a solution of ethylmagnesium bromide (EtMgBr) in THF 1.1 mL (1.1 mmol) was added dropwise at room temperature. After the ethylmagnesium bromide was added, the mixture was heated at 50° C. for 15 min and cooled to room temperature. A solution of 0.24 g (1.0 mmol) of azide 2 in THF (1.0 M) was added dropwise and the mixture heated to 50° C. for 1 h. After quenching with a solution of 10% ammonium chloride (NH$_4$Cl), the products were extracted with ethyl acetate (3×). The organic layer was washed with 10 mL of brine, separated and dried on sodium sulfate, filtered and concentrated on a rotary evaporator to obtain crude material (0.1104 g). The crude oil was purified via silica gel chromatography to obtain 0.29 g (0.86 mmol=86%) of 1-(9-Ethyl-9H-carbazol-3-yl)-5-phenyl-1H-1,2,3-triazole (I-1). The product was identified to be essentially pure by TLC and NMR: R$_f$=0.26 (3:1, hexane/ethyl acetate); $^1$H NMR (CDCl$_3$, 400 MHz) δ 1.45 (t, J=6.64 Hz, 3H), 4.38 (q, J=7.24 Hz, 2H), 7.25 (d, J=5.5, 1H), 7.27-7.29 (m, 4H), 7.31 (t, J=1.7 Hz, 1H), 7.36 (dd, J=1.9, 8.6 Hz, 1H), 7.39 (d, J=8.6 Hz, 1H), 7.44 (d, J=8.2 Hz, 1H), 7.52 (t, J=7.2 Hz, 1H); $^{13}$C (CDCl$_3$, 100 MHz) δ 13.8, 37.8, 53.4, 108.7, 108.9, 117.8, 119.5, 120.7, 122.0, 122.9, 123.1, 126.6, 127.0, 128.3, 128.5, 128.7, 128.9, 133.0, 138.0, 139.7, 140.6. LRGC-MS m/z (rel %): [M]$^+$338 (37), [M-C2H5]$^+$ 310 (55), [M-C2H5N]$^+$295 (100), [M-C2H5N2]$^+$ 281 (34), [M-C9H9N3]$^+$ 179 (34).

Step 2: Synthesis of 1-(9-Ethyl-9H-carbazol-3-yl)-5-phenyl-1H-1,2,3-triazole (I-1)

To a 25 mL 3-neck round bottom flask containing phenylacetylene 0.11 g (1.1 mmol) under a nitrogen atmosphere, a solution of ethylmagnesium bromide (EµMgBr) in THF 1.1 mL (1.1 mmol) was added dropwise at room temperature. After the ethylmagnesium bromide was added, the mixture was heated at 50° C. for 15 min and cooled to room temperature. A solution of 0.24 g (1.0 mmol) of azide 2 in THF (1.0 M) was added dropwise and the mixture heated to 50° C. for 1 h. After quenching with a solution of 10% ammonium chloride (NH$_4$C$_1$), the products were extracted with ethyl acetate (3×). The organic layer was washed with 10 mL of brine, separated and dried on sodium sulfate, filtered and concentrated on a rotary evaporator to obtain crude material (0.1104 g). The crude oil was purified via silica gel chromatography to obtain 0.29 g (0.86 mmol=86%) of 1-(9-Ethyl-9H-carbazol-3-yl)-5-phenyl-1H-1,2,3-triazole (I-1). The product was identified to be essentially pure by TLC and NMR: $R_f$=0.26 (3:1, hexane/ethyl acetate); $^1$H NMR (CDCl$_3$, 400 MHz) δ 1.45 (t, J=6.64 Hz, 3H), 4.38 (q, J=7.24 Hz, 2H), 7.25 (d, J=5.5, 1H), 7.27-7.29 (m, 4H), 7.31 (t, J=1.7 Hz, 1H), 7.36 (dd, J=1.9, 8.6 Hz, 1H), 7.39 (d, J=8.6 Hz, 1H), 7.44 (d, J=8.2 Hz, 1H), 7.52 (t, J=7.2 Hz, 1H); $^{13}$C (CDCl$_3$, 100 MHz) δ 13.8, 37.8, 53.4, 108.7, 108.9, 117.8, 119.5, 120.7, 122.0, 122.9, 123.1, 126.6, 127.0, 128.3, 128.5, 128.7, 128.9, 133.0, 138.0, 139.7, 140.6. LRGC-MS m/z (rel %): [M]$^+$338 (37), [M-C2H5]$^+$ 310 (55), [M-C2H5N]$^+$295 (100), [M-C2H5N2]$^+$ 281 (34), [M-C9H9N3]$^+$ 179 (34).

Cell Culture

MDA-MB-231, MCF-7 (ATCC), green fluorescent protein (GFP) tagged bone metastatic variant of MDA-MB-435 (GFP-HER2-BM) (characterized in (25), from Dr. Danny Welch, The University of Kansas Cancer Center), and MCF10A mammary epithelial cells (ATCC) were cultured and maintained as previously described (16). MDA-MB-231 and MCF-7 cell lines were obtained in 2000, the MCF-10A cell line was purchased in 2013, and the GFP-HER2-BM cell line was a gift from Dr. Danny Welch in 2008. The cell lines were authenticated by ATCC in 2015.

Rac and Cdc42 Activation Assays

For the $IC_{50}$ curves: Rac 1/2/3 and Cdc42 activation was determined as described (16), using a G-LISA kit (Cytoskeleton, Inc., Denver, Colo.). MDA-MB-231 cell lysates were prepared from 24 h MBQ-167 treatment by combining attached and detached cell populations (N=3). Four-parameter dose-response $IC_{50}$ curves were fitted using the nonlinear regression function of GraphPad Prism®.

Additionally, Rac, Cdc42, or Rac activation was determined, by pulldowns using the P21-binding domain (PBD) of PAK, or Rho binding domain of Rhotekin as described (2, 16). The GTP bound active Rac, Cdc42, or Rho was detected by Western blot (N=3).

Western Blot Analysis

Total cell lysates or pull-downs were Western blotted using routine procedures. The primary antibodies used were: Rac (Rac1,2,3), Cdc42, Bcl-xL, Bcl-2, Mcl-1, PAK1, PAK2, phospho (p)-PAK1(T423)/PAK2(T402), p-PAK1(S199/204)/PAK2(S192/197), p-PAK (S144/204)/PAK2(S141), LIM kinase (LIMK1), p-LIMK1/2(Tyr507/Thr508), Cofilin, p-cofilin(S3), STAT3, p-STAT3(Y705), p-P-38 MAPK (T180/Y182), p-ERK (T202/Y204), p-Akt (S473), and Akt (Cell Signaling Technology, Inc.) and p3-actin (Sigma).

Fluorescence Microscopy

MDA-MB-231 cells were treated with vehicle or MBQ-167 at 250 or 500 nM for 24 h. Cells were fixed, permeabilized, and stained with Rhodamine phalloidin to visualize F-actin, and with p-tyrosine or vinculin to visualize focal adhesions, as described (2). Fluorescence micrographs were acquired at 600× in an Olympus BX40 fluorescence microscope using a Spot digital camera.

Cell Migration Assays

Transwell Assay:

As described (2), quiescent MDA-MB-231 cells were treated with vehicle or MBQ-167 (250 nM) for 24 h. The attached and detached populations were separated and exactly 2×10$^5$ cells were placed on the top well of Transwell chambers with 5% FBS in the bottom well. The number of cells that migrated to the underside of the membrane following a 7 h incubation was quantified after staining fixed cells with propidium iodide (PI). For each treatment (N=3), cells in 20 microscopic fields were quantified.

Wound Healing Scratch Assay:

MDA-MB-231 cells plated on 6-well plates at equal cell density were incubated in 10% FBS until confluent. The media was changed to 2% FBS and a single scratch was made in the center of the monolayer culture with a pipet tip. MBQ-167 was added at 0, 250, or 500 nM immediately following wounding. Images were digitally acquired from an Olympus microscope (4× magnification) at 0, 8, 12, and 24 h and the scratch distance quantified in Adobe Photoshop. N=3 biological replicates (with 2 technical replicates each).

Mammosphere Formation Assay

As described (26), Equal numbers of MDA-MB-231 cells treated with vehicle or MBQ-167 were seeded in ultra-low attachment plates (Corning) at a density of 500 cells/well in serum-free mammary epithelium basal medium (Lonza). Mammospheres were counted after 4 days incubation in 0 or 250 nM MBQ-167 at 37° C., 5% $CO_2$. Mammosphere-forming efficiency was calculated as the number of mammospheres divided by the number of cells seeded per well and expressed relative to vehicle controls.

Cell Viability Assays

As described (16), equal numbers of MDA-MB-231, GFP-HER2-BM, or MCF-10A cells were incubated in 0-1 µM MBQ-167 for 120 h. The CellTiter 96® Non-Radioactive Cell Proliferation Assay (Promega, Fitchburg, Wis.) was used according to the manufacturer's instructions. This assay allows the quantification of the viability of both attached and detached cells in the same well. $GI_{50}$ was determined as $100\times(T-T_0)/(C-T_0)=50$ (T=the optical density of drug treatment after 120 h, $T_0$=the optical density at time zero, and C=the optical density of the untreated cells). Curves were fitted using the four-parameter logistic nonlinear regression models in GraphPad Prism software.

Cell Cycle Progression

MDA-MB-231 cells were incubated with 0 or 250 nM MBQ-167 for 48 h and all cells (detached and attached) were stained with PI, as in (27). Cell cycle stage was analyzed using a four-color flow cytometer (FACSCalibur, BD Biosciences, San Jose, Calif.). A total of 20,000 events were analyzed for each sample. List-mode files were collected using Cell Quest software 3.3 and analyzed using the Flow Jo software vX.0.7 (BD Biosciences, San Jose, Calif.).

Apoptosis Assay

Apoptosis was measured using a Caspase-Glo3/7 Luminescence Assay Kit as per manufacturer's instructions (Promega, Corp., Madison, Wis., USA). Following treatment of equal numbers of cells with vehicle or MBQ-167 for 24 h, Caspase-3/7 Glo reagent was added and incubated at room temperature for 60 min. Caspase-3/7 activities were determined by quantifying luminescence.

Annexin V Staining

Apoptotic cells were detected by fluorescence microscopy of Annexin V-Cy3-18 stained cells as per manufacturer's instructions (Sigma-Aldrich, St Louis, Mo., USA). Briefly, GFP-MDA-MB-231 cells grown on coverslips were treated with vehicle, or 250 or 500 nM MBQ-167 for 6 h and stained with Annexin V-Cy3-18 in binding buffer (10 mM HEPES/NaOH, pH 7.5, 0.14 M NaCl, 2.5 mM $CaCl_2$) for 15 min at room temperature. Coverslips were washed in binding buffer and fixed with 3.7% paraformaldehyde prior to fluorescence microscopy. Images were digitally acquired from an Olympus inverted fluorescence microscope.

Animal Protocol

All animal studies were conducted under approved protocol #A8180112 Institutional Animal Care and Use Committee, in accordance with the *NIH Guideline for the Care and Use of Laboratory Animals*. Female athymic nu/nu mice and severe combined immunodeficiency Crl:SHO-Prkdc SCID Hairless 4 to 5 wk old (Charles River Laboratories, Inc., Wilmington, Mass.) were maintained under pathogen-free conditions in HEPA-filtered cages.

Tumor Establishment

GFP-HER2-BM cells (~5×105) or GFP-MDA-MB-231 cells (1×105) in Matrigel (BD Biosciences, San Jose, Calif.) were injected at the fourth right mammary fat pad under isofluorane inhalation (1-3% in oxygen using an inhalation chamber at 2 L/min) to produce orthotopic primary tumors. After tumor establishment (lwk post-inoculation), animals were randomly divided into treatment groups (n=6).

Administration of MBQ-167

Mice were treated with vehicle (12.5% ethanol, 12.5% Cremophor (Sigma-Aldrich, St. Louis, Mo.), and 75% 1×PBS pH 7.4), or 1 or 10 mg/kg BW MBQ-167 by i.p. injection in a 100 µL volume 3× a wk. Treatments continued until sacrifice at day 65.

Whole Body Fluorescence Image Analysis

Mammary tumor growth was quantified as changes in the integrated density of GFP fluorescence, as in (28). Mice were imaged on day 1 of treatment administration, and once a week thereafter for 65 days, using the FluorVivo small animal in vivo imaging system (INDEC Systems, Inc., Santa Clara, Calif.). Tumor fluorescence intensities were analyzed using Image J software (National Institutes of Health, Bethesda, Md.). Relative tumor growth was calculated as the integrated density of fluorescence of each tumor on each day of imaging relative to the integrated density of fluorescence of the same tumor on day 1 of treatment, as described (17). As in (29), Optimal Tumor growth was calculated as % T/C=(δT/δC)×100 when δT>0, δT=average tumor size on day 65 of treated mice-average tumor size on day 01 of treated mice. δC=average tumor size on day 65 of control mice-average tumor size on day 01 of control mice. Tumor growth delay was calculated as the percentage by which the treated group tumor size is delayed in attaining a specified number of doublings (from day 1) compared with controls using: [(T−C)/C]×100, where T and C are the median times in days for treated and control groups to double in tumor size.

Analysis of Metastases

Following sacrifice, lungs, kidneys, livers, bones, and spleens were excised and immediately stored in liquid N2. Stored organs were thawed and analyzed by fluorescence microscopy, as described.

Liver Enzyme Assays

Frozen stored livers were thawed and homogenized to measure alkaline phosphatase (ALP) and alanine transaminase (ALT) activities using colorimetric assay kits from Abcam and Cayman Chemicals respectively, as per manufacturer's instructions.

Statistical Analysis

Statistical analyses used Microsoft Excel and GraphPad Prism, and differences were considered statistically significant at P≤0.05.

TABLE 1A

| Cmpd# | Structure | Rac activity | Cdc42 activity | $^1$H-NMR | Name |
|---|---|---|---|---|---|
| I-1 | 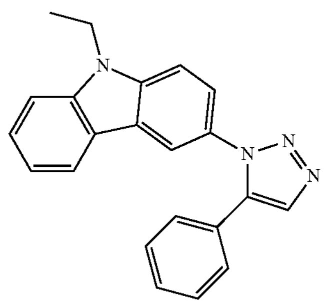 [SMILES: CCn1c2ccccc2c2cc(-n3nncc3-c3ccccc3)ccc21] | A | A | (CDCl$_3$) δ 1.43 (t, J = 7.26 Hz, 3H), 4.37 (q, J = 7.24 Hz, 2H), 7.14 (dd, J = 2.17, 8.63 Hz, 1H), 7.24 (t, J = 7.13 Hz, 1H), 7.37 (d, J = 8.64 Hz, 1H), 7.41 (d, J = 8.24 Hz, 1H), 7.49 (t, J = 8.17 Hz, 1H), 7.75 (d, J = 2.19 Hz, 1H), 8.07 (d, J = 7.80 Hz, 1H) | 9-ethyl-3-(5-phenyl-1H-1,2,3-triazol-1-yl)-9H-carbazole |
| I-2 | 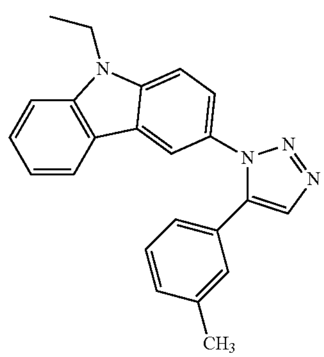 [SMILES: CCn1c2ccccc2c2cc(-n3nncc3-c3cccc(C)c3)ccc21] | | | (CDCl$_3$) δ 1.45 (t, J = 7.24 Hz, 3H), 4.38 (q, J = 7.24 Hz, 2H), 6.99 (dd, J = 1.4, 8.76, 1H), 7.12-7.17 (m, 3H), 7.24 (t, J = 7.0 Hz, 1H), 7.34 (dd, J = 2.0, 8.6 Hz, 1H), 7.39 (d, J = 8.6 Hz, 1H), 7.45 (d, J = 8.2 Hz, 1H), 7.51 (t, J = 7.2 Hz, 1H), 7.91 (s, 1H), 8.01 (d, J = 7.8 Hz, 1H), 8.17 (d, J = 1.9 Hz, 1H) | 9-ethyl-3-(5-(m-tolyl)-1H-1,2,3-triazol-1-yl)-9H-carbazole |

TABLE 1A-continued
| | | | |
|---|---|---|---|
| I-3 | 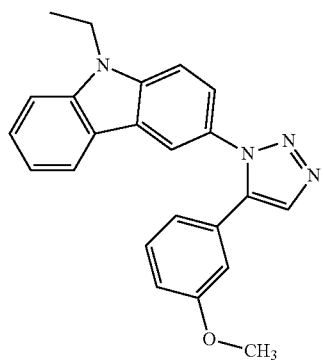 | (CDCl₃) δ 1.45 (t, J = 7.20 Hz, 3H), 3.63 (s, 3H), 4.39 (q, J = 7.20 Hz, 2H), 6.81 (dd, J = 1.4, 4.5, 1H), 6.85 (dd, J = 2.5, 9.5 Hz, 1H), 7.19 (t, J = 8.0 Hz, 1H), 7.36 (dd, J = 2.0, 8.6 Hz, 1H), 7.41 (d, J = 8.6 Hz, 1H), 7.45 (d, J = 8.2 Hz, 1H), 7.52 (t, J = 7.2 Hz, 1H), 7.92 (s, 1H), 8.20 (d, J = 7.8 Hz, 1H), 8.16 (d, J = 1.9 Hz, 1H); | 9-ethyl-3-(5-(3-methoxyphenyl)-1H-1,2,3-triazol-1-yl)-9H)-carbazole |
| I-4 | 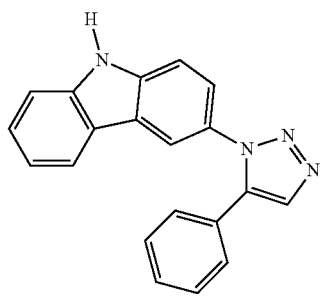 [SMILES: c1ccc(-c2cnnn2-c2ccc3[nH]c4ccccc4c3c2)cc1] | | |
| I-5 | 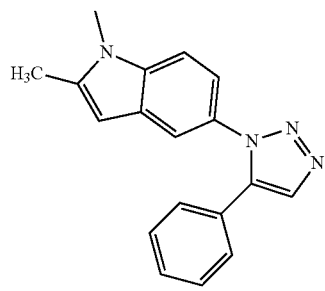 [SMILES: Cc1cc2cc(-n3nncc3-c3ccccc3)ccc2n1C] | | |
| I-6 | 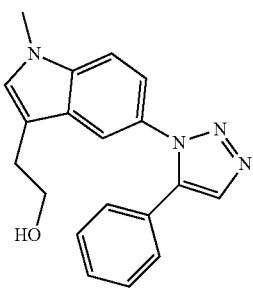 [SMILES: Cn1cc(CCO)c2cc(-n3nncc3-c3ccccc3)ccc21] | | |
| I-7 | 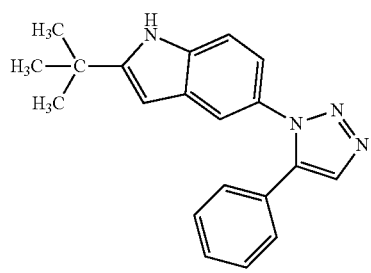 [SMILES: CC(C)(C)c1cc2cc(-n3nncc3-c3ccccc3)ccc2[nH]1] | | |

TABLE 1A-continued
I-8 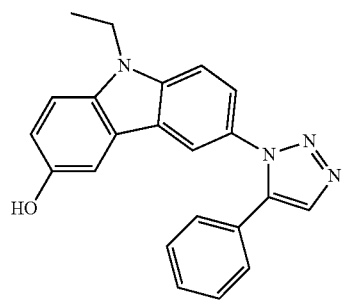 [SMILES: CCn1c2ccc(O)cc2c2cc(-n3nncc3-c3ccccc3)ccc21]
I-9 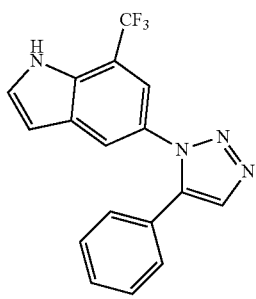 [SMILES: FC(F)(F)c1cc(-n2nncc2-c2ccccc2)cc2cc[nH]c12]
I-10 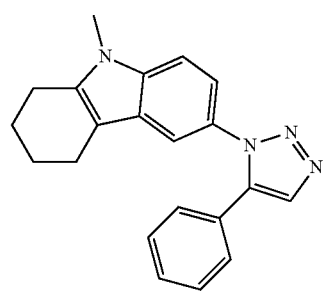 [SMILES: Cn1c2c(c3cc(-n4nncc4-c4ccccc4)ccc31)CCCC2]
I-11 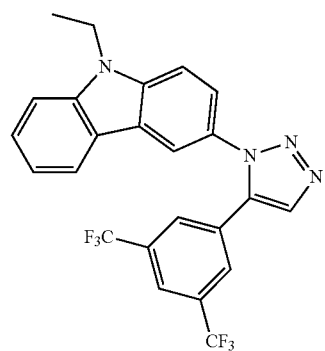 [SMILES: CCn1c2ccccc2c2cc(-n3nncc3-c3cc(C(F)(F)F)cc(C(F)(F)F)c3)ccc21]
I-12 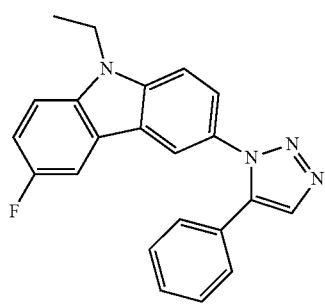 [SMILES: CCn1c2ccc(F)cc2c2cc(-n3nncc3-c3ccccc3)ccc21]

TABLE 1A-continued
I-13
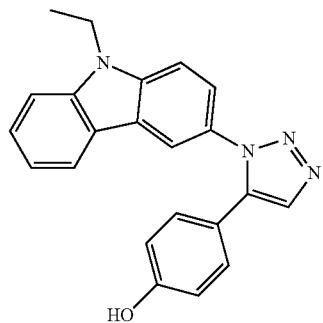 [SMILES: CCn1c2ccccc2c2cc(-n3nncc3-c3ccc(O)cc3)ccc21]
I-14
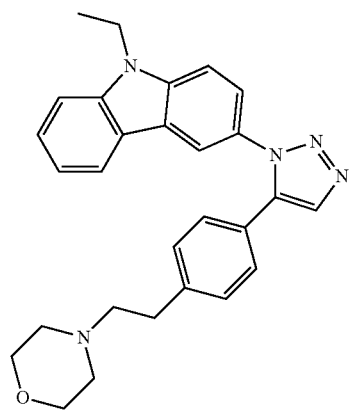 [SMILES: CCn1c2ccccc2c2cc(-n3nncc3-c3ccc(CCN4CCOCC4)cc3)ccc21]
I-15
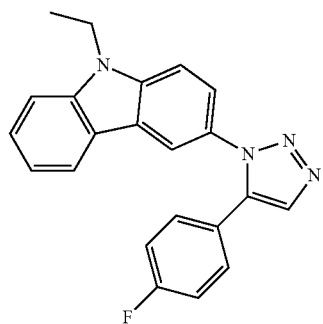 [SMILES: CCn1c2ccccc2c2cc(-n3nncc3-c3ccc(F)cc3)ccc21]
I-16
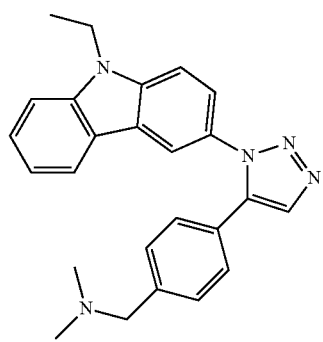 [SMILES: CCn1c2ccccc2c2cc(-n3nncc3-c3ccc(CN(C)C)cc3)ccc21]

TABLE 1A-continued
I-17
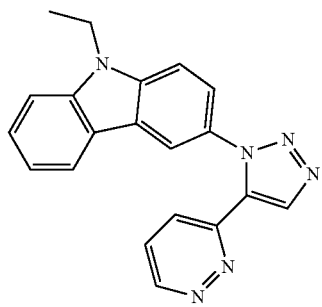 [SMILES: CCn1c2ccccc2c2cc(-n3nncc3-c3cccnn3)ccc21]
I-18
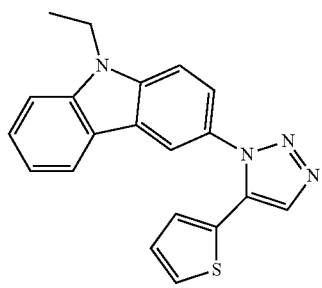 [SMILES: CCn1c2ccccc2c2cc(-n3nncc3-c3cccs3)ccc21]
I-19
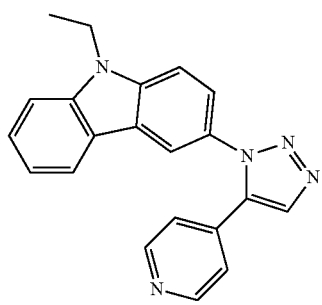
I-20
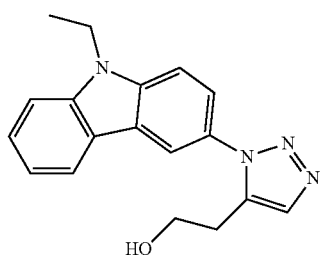 [SMILES: CCn1c2ccccc2c2cc(-n3nncc3CCO)ccc21]
I-21
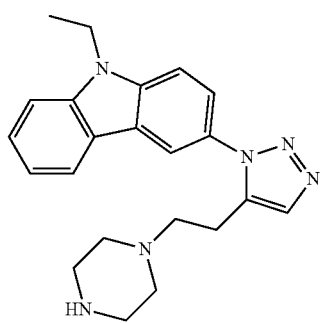 [SMILES: CCn1c2ccccc2c2cc(-n3nncc3CCN3CCNCC3)ccc21]

TABLE 1A-continued
I-22 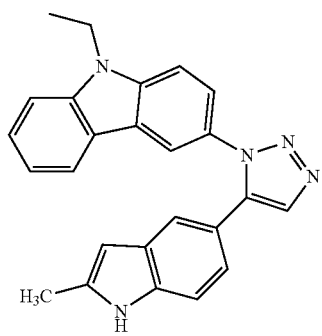 [SMILES: CCn1c2ccccc2c2cc(-n3nncc3-c3ccc4[nH]c(C)cc4c3)ccc21]
I-23 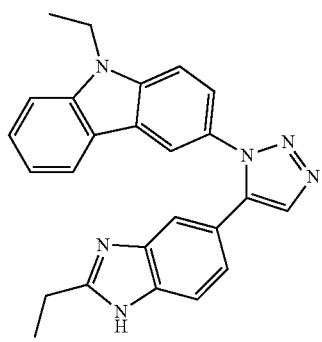 [SMILES: CCc1nc2cc(-c3cnnn3-c3ccc4c(c3)c3ccccc3n4CC)ccc2[nH]1]
I-24 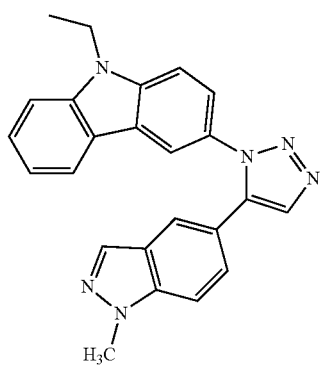 [SMILES: CCn1c2ccccc2c2cc(-n3nncc3-c3ccc4c(cnn4C)c3)ccc21]
I-25 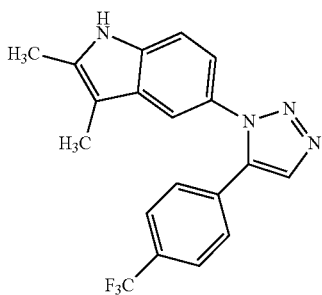 [SMILES: Cc1[nH]c2ccc(-n3nncc3-c3ccc(C(F)(F)F)cc3)cc2c1C]
I-26 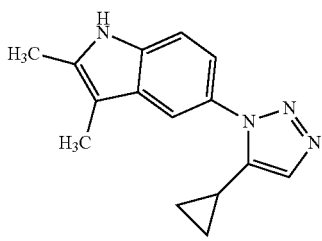 [SMILES: Cc1[nH]c2ccc(-n3nncc3C3CC3)cc2c1C]

TABLE 1A-continued
I-27 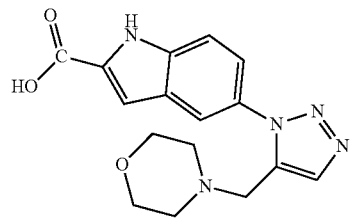 [SMILES: O=C(O)c1cc2cc(-n3nncc3CN3CCOCC3)ccc2[nH]1]
I-28 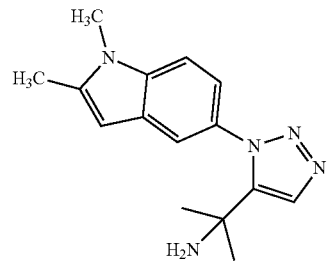 [SMILES: Cc1cc2cc(-n3nncc3C(C)(C)N)ccc2n1C]
I-29 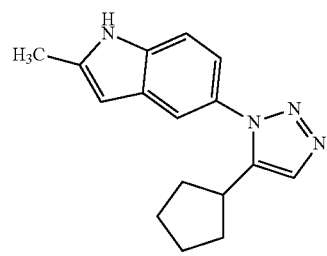 [SMILES: Cc1cc2cc(-n3nncc3C3CCCC3)ccc2[nH]1]
I-30 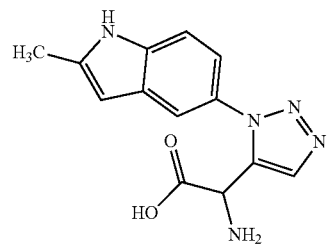 [SMILES: Cc1cc2cc(-n3nncc3C(N)C(=O)O)ccc2[nH]1]
I-31 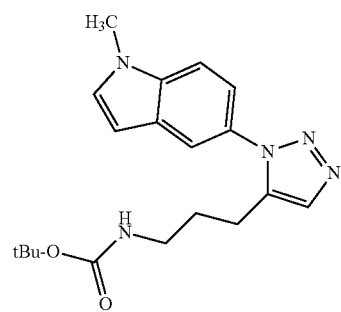

TABLE 1A-continued
I-32
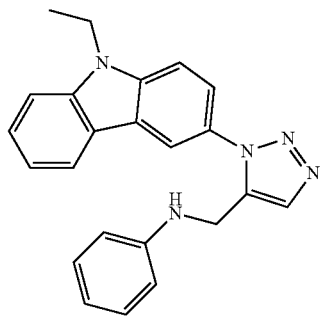 [SMILES: CCn1c2ccccc2c2cc(-n3nncc3CNc3ccccc3)ccc21]
I-33
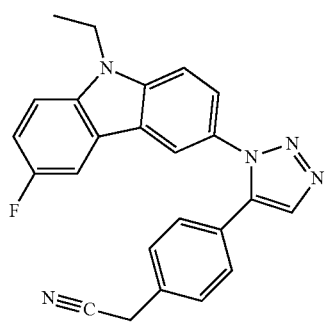 [SMILES: CCn1c2ccc(F)cc2c2cc(-n3nncc3-c3ccc(CC#N)cc3)ccc21]
I-34
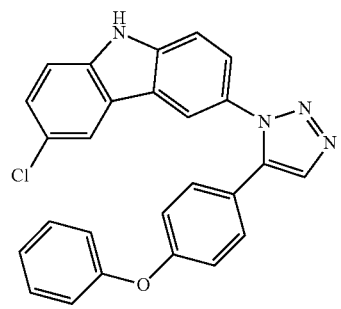 [SMILES: Clc1ccc2[nH]c3ccc(-n4nncc4-c4ccc(Oc5ccccc5)cc4)cc3c2c1]
I-35
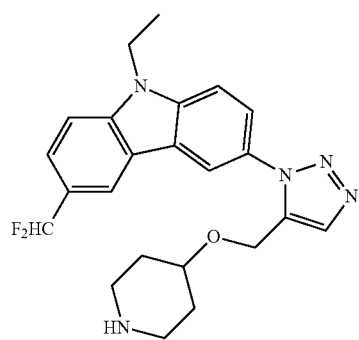 [SMILES: CCn1c2ccc(C(F)F)cc2c2cc(-n3nncc3COC3CCNCC3)ccc21]

TABLE 1A-continued
I-36
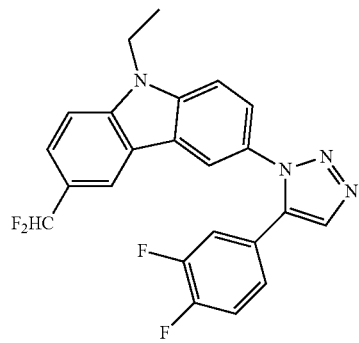 [SMILES: CCn1c2ccc(C(F)F)cc2c2cc(-n3nncc3-c3ccc(F)c(F)c3)ccc21]
I-37
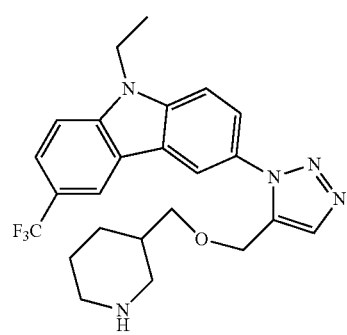 [SMILES: CCn1c2ccc(-n3nncc3COCC3CCCNC3)cc2c2cc(C(F)(F)F)ccc21]
I-38
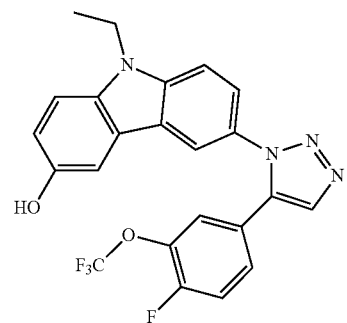 [SMILES: CCn1c2ccc(O)cc2c2cc(-n3nncc3-c3ccc(F)c(OC(F)(F)F)c3)ccc21]
I-39
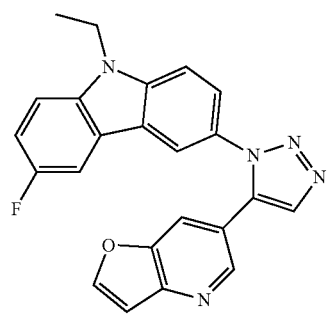 [SMILES: CCn1c2ccc(F)cc2c2cc(-n3nncc3-c3cnc4ccoc4c3)ccc21]

TABLE 1A-continued
I-40
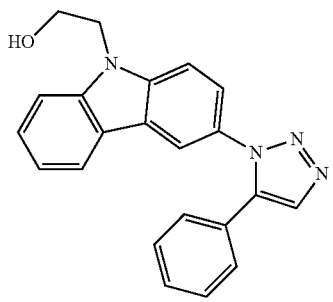 [SMILES: OCCn1c2ccccc2c2cc(-n3nncc3-c3ccccc3)ccc21]
I-41
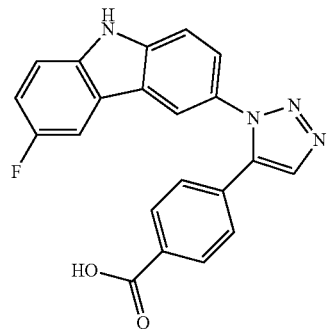 [SMILES: O=C(O)c1ccc(-c2cnnn2-c2ccc3[nH]c4ccc(F)cc4c3c2)cc1]
I-42
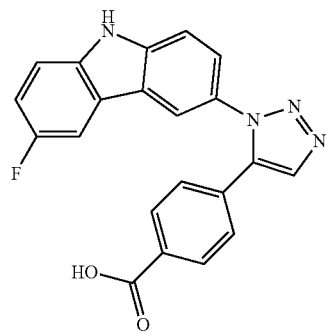 [SMILES: O=C(O)c1ccc(-c2cnnn2-c2ccc3[nH]c4ccc(F)cc4c3c2)cc1]
I-43
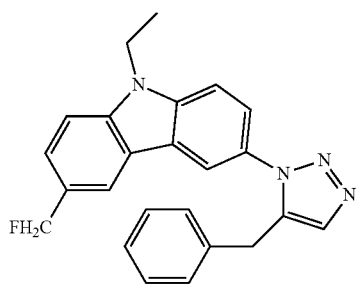
I-44
I-45
I-46
I-47
I-48
I-49
I-50
I-51
A: >50% inhibition at 250 nM;
B: >50% inhibition at 1 μM;
C >50% inhibition at 5 μM;
D <50% inhibition at 5 μM.

TABLE 1B

| Cmpd# | Structure | GI$_{50}$ (μM) MDA-MB-231 | Migration Inhibition (%) MDA-MB-231 | $^1$H-NMR and $^{13}$C-NMR | Name |
|---|---|---|---|---|---|
| I-1 | 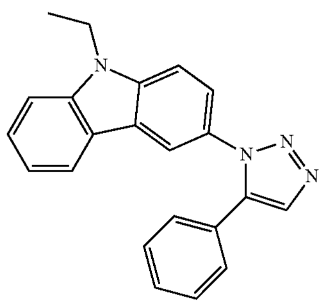 [SMILES: CCn1c2ccccc2c2cc(-n3nncc3-c3ccccc3)ccc21] | 0.128 | 37.2 (0.25 μM) | $^1$H-NMR (400 MHz, CDCl$_3$) δ 1.43 (t, J = 7.3, 3H), 4.37 (q, J = 7.2, 2H), 7.14 (dd, J = 2.17, 8.63, 1H), 7.24 (t, J = 7.13, 1H), 7.37 (d, J = 8.64, 1H), 7.41 (d, J = 8.24, 1H), 7.49 (t, J = 8.17, 1H), 7.75 (d, J = 2.19, 1H), 8.07 (d, J = 7.80, 1H); $^{13}$C NMR (100 MHz, CDCl$_3$) δ 13.8, 37.8, 108.7, 108.9, 117.8, 119.5, 120.8, 122.5, 123.0, 123.2, 126.6, 127.1, 128.3, 128.5, 128.8, 128.0, 133.0, 138.0, 139.8, 140.7. | 9-ethyl-3-(5-phenyl-1H-1,2,3-triazol-1-yl)-9H-carbazole |
| I-2 | 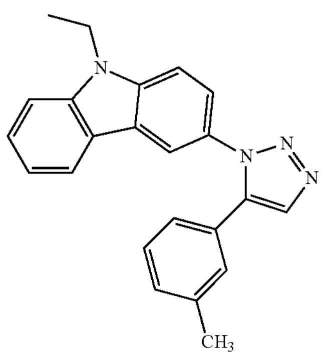 [SMILES: CCn1c2ccccc2c2cc(-n3nncc3-c3cccc(C)c3)ccc21] | 1.332 | ≤1 (1 μM) | $^1$H-NMR (400 MHz, CDCl$_3$) δ 1.45 (t, J = 7.24, 3H), 4.38 (q, J = 7.24, 2H), 6.99 (dd, J = 1.4, 8.76, 1H), 7.12-7.17 (m, 3H), 7.24 (t, J = 7.0, 1H), 7.34 (dd, J = 2.0, 8.6, 1H), 7.39 (d, J = 8.6, 1H), 7.45 (d, J = 8.2, 1H), 7.51 (t, J = 7.2, 1H), 7.91 (s, 1H), 8.01 (d, J = 7.8, 1H), 8.17 (d, J = 1.9, 1H); $^{13}$C NMR (100 MHz, CDCl$_3$) δ 14.0, 21.6, 38.1, 108.9, 109.2, 118.1, 119.8, 121.1, 122.8, 123.3, 123.4, 125.9, 126.9, 127.2, 128.7, 128.9, 129.5, 130.0, 133.3, 138.4, 138.8, 140.0, 140.9. | 9-ethyl-3-(5-(m-tolyl)-1H-1,2,3-triazol-1-yl)-9H-carbazole |
| I-3 | 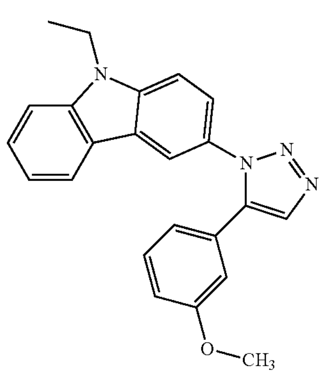 [SMILES: CCn1c2ccccc2c2cc(-n3nncc3-c3cccc(OC)c3)ccc21] | 0.248 | ≤1 (1 μM) | $^1$H-NMR (400 MHz, CDCl$_3$) δ 1.45 (t, J = 7.2, 3H), 3.63 (s, 3H), 4.39 (q, J = 7.2 2H), 6.81 (dd, J = 1.4, 4.5, 1H), 6.85 (dd, J = 2.5, 9.5, 1H), 7.19 (t, J = 8.0, 1H), 7.36 (dd, J = 2.0, 8.6, 1H), 7.41 (d, J = 8.6, 1H), 7.45 (d, J = 8.2, 1H), 7.52 (t, J = 7.2, 1H), 7.92 (s, 1H), 8.20 (d, J = 7.8, 1H), 8.16 (d, J = 1.9, 1H); $^{13}$C NMR (100 MHz, CDCl$_3$) δ 13.8, 37.9, 55.4, 109.0, 109.1, 110.9, 113.3, 114.4, 118.3, 118.6, 119.1, 119.6, 120.8, 122.6, 123.4, 126.7, 129.5, 129.9, 131.9, 139.6, 140.9, 148.1, 160.1. | 9-ethyl-3-(5-(3-methoxyphenyl)-1H-1,2,3-triazol-1-yl)-9H-carbazole |
| I-4 | 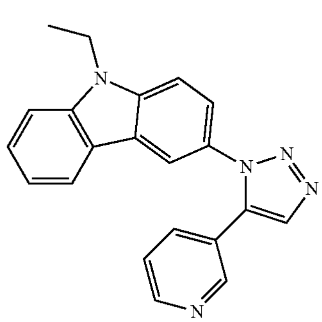 [SMILES: CCn1c2ccccc2c2cc(-n3nncc3-c3cccnc3)ccc21] | >50 | 65.1 (10 μM) | $^1$H-NMR (400 MHz, CDCl$_3$) δ 1.47 (t, 3H, J = 7.2), 4.39 (q, J = 7.14, 2H), 7.2158 (d, 1H), J = 3.0), 7.26 (t, 1H, J = 7.4), 7.34 (d, J = 1.8, 1H), 7.36 (d, 1H, J = 1.8), 7.42 (s, 1H), 7.45 (d, 1H, J = 4.4), 7.52 (t, 1H, J = 7.3), 8.01 (d, 1H, J = 6.0), 8.12 (s, 1H), 8.56 (d, J = 4.6, 1H), 8.62 (s, 1H). $^{13}$C NMR (100 MHz, CDCl$_3$) δ 13.7, 37.8, 108.9, 117.8, 119.6, 120.7, 122.2, 122.4, 122.2, 123.2, 123.4, 123.4, 126.7, 149.9. | 9-ethyl-3-(5-(pyridin-3-yl)-1H-1,2,3-triazol-1-yl)-9H-carbazole |

TABLE 1B-continued

| Cmpd# | Structure | GI$_{50}$ (μM) MDA-MB-231 | Migration Inhibition (%) MDA-MB-231 | $^1$H-NMR and $^{13}$C-NMR | Name |
|---|---|---|---|---|---|
| I-5 | 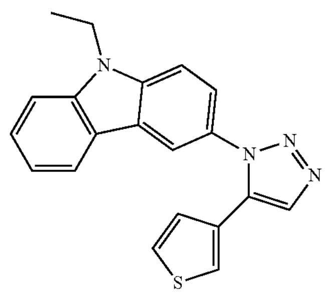 [SMILES: CCn1c2ccccc2c2cc(-n3nncc3-c3ccsc3)ccc21] | 0.408 | 2.4 (1 μM) | $^1$H-NMR (400 MHz, CDCl$_3$) δ 1.50 (t, 3H, J = 7.2), 4.43 (q, 2H, J = 7.239), 6.97 (d, J = 5.0, 1H), 7.09 (d, J = 2.84, 1H),), 7.2720 (t, J = 3.0, 1H), 7.45 (d, J = 1.9, 1H), 7.48 (d, 1H, J = 6.137), 7.53 (d, 1H, J = 7.2), 7.95 (s, 1H), 8.04 (d, 1H, J = 7.8), 8.16 (s, 1H); $^{13}$C NMR (100 MHz, CDCl$_3$) δ 13.8, 37.9, 108.9, 108.9, 118.3, 119.7, 120.8, 122.5, 123.2, 123.3, 124.3, 126.5, 126.7, 126.9, 127.0, 128.2, 132.3, 134.1, 140.0, 140.7. | 9-ethyl-3-(5-(thiophen-3-yl)-1H-1,2,3-triazol-1-yl)-9H-carbazole |
| I-6 | 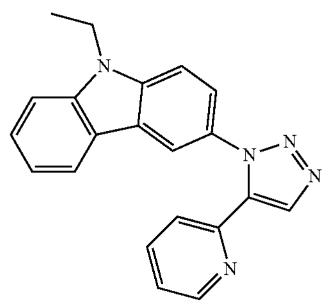 | >50 | 28 (10 μM) | $^1$H-NMR (400 MHz, CDCl$_3$) δ 1.48 (t, 3H, J = 7.1), 4.43 (q, 2H, J = 7.3), 7.29 (t, 1H, J = 13.5), 7.47 (d, 1H, J = 8.1), 7.53 (t, 1H, J = 7.8), 7.83 (t, 1H, J = 7.8), 7.87 (d, 1H, J = 2.11), 7.89 (d, 1H, J = 2.1), 8.13 (d, 1H, J = 7.36), 8.29 (d, 1H, J = 7.2), 8.49 (s, 1H), 8.64 (d, 1H, J = 4.1), 8.68 (s, 1H); $^{13}$C NMR (100 MHz, CDCl$_3$) δ 13.8, 37.9, 108.9, 109.1, 113.2, 118.8, 119.6, 120.4, 120.7, 120.8, 122.6, 122.9, 123.4, 126.7, 129.4, 136.9, 139.7, 140.8, 148.8, 149.5, 150.3. | 9-ethyl-3-(5-(pyridin-2-yl)-1H-1,2,3-triazol-1-yl)-9H-carbazole |
| I-7 | 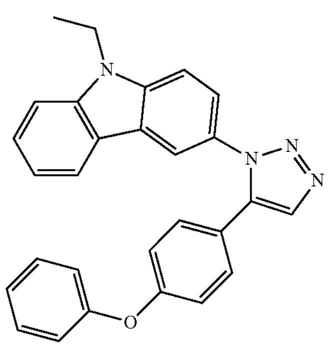 [SMILES: CCn1c2ccccc2c2cc(-n3nncc3-c3ccc(Oc4ccccc4)cc3)ccc21] | >50 | 30.8 (10 μM) | $^1$H-NMR (400 MHz, CDCl$_3$) δ 1.48 (t, 3H, J = 7.3), 4.41 (q, 2H, J = 5.652), 6.8907 (d, 1H, J = 7.9), 7.9872 (d, 1H, J = 3.0), 7.00 (d, 1H, J = 4.20), 7.09 (t, 1H, J = 8.3), 7.21 (d, 1H, J = 8.6), 7.26 (d, 1H, J = 9.7), 7.32 (t, 1H, J = 7.7), 7.41 (d, 1H, J = 6.4), 7.46 (d, 1H, J = 9.7), 7.53 (t, 1H, J = 6.5), 7.90 (s, 1H), 8.04 (d, 1H, J = 4.3), 8.13 (s, 1H); $^{13}$C NMR (100 MHz, CDCl3) δ 13.9, 37.9, 108.8, 108.9, 117.3, 117.918, 118.405, 119.604, 120.239, 120.8, 121.5, 122.5, 123.1, 123.2, 124.1, 124.7, 126.7, 128.3, 129.9, 130.0, 130.1, 132.4, 132.8, 138.1, 139.8, 140.7. | 9-ethyl-3-[5-(4-phenoxy-phenyl)-1H-1,2,3-triazol-1-yl)]-9H-carbazole |
| I-8 | 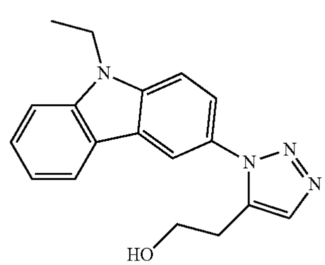 [SMILES: CCn1c2ccccc2c2cc(-n3nncc3CCO)ccc21] | >50 | n/a | $^1$H-NMR (400 MHz, CDCl$_3$) δ 1.46 (t, J = 7.6, 3H), 2.96 (t, J = 6.3, 2H), 3.85 (t, J = 6.3, 2H), 4.41 (q, J = 7.6, 2H), 7.25 (dd, J = 7.6, 1H), 7.44-7.55 (m, 4H), 7.71 (s, 1H), 8.04 (d, J = 7.6, 1H), 8.14 (t, J = 1.4, 1H). | 2-(1-(9-ethyl-9H-carbazol-3-yl)-1H-1,2,3-triazol-5-yl)ethan-1-ol |
| I-9 | 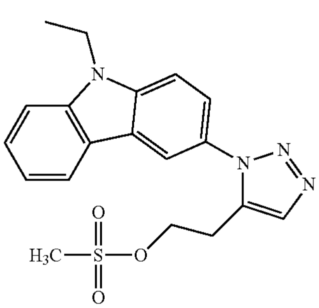 [SMILES: CCn1c2ccccc2c2cc(-n3nncc3CCOS(C)(=O)=O)ccc21] | n/a | n/a | $^1$H-NMR (400 MHz, CDCl$_3$) δ 1.49 (t, J = 7.2, 3H), 2.95 (s, 3H), 3.20 (t, J = 6.4, 2H), 4.38 (t, J = 6.4, 2H), 4.45 (q, J = 7.2, 2H), 7.30 (dd, J = 7.2, 1H), 7.43-7.58 (m, 4H), 7.77 (s, 1H), 8.10 (d, J = 8.0, 1H), 8.13 (t, J = 1.6, 1H) | 2-(1-(9-ethyl-9H-carbazol-3-yl)-1H-1,2,3-triazol-5-yl)ethyl methanesulfonate |

TABLE 1B-continued

| Cmpd# | Structure | GI$_{50}$ (μM) MDA-MB-231 | Migration Inhibition (%) MDA-MB-231 | $^1$H-NMR and $^{13}$C-NMR | Name |
|---|---|---|---|---|---|
| I-10 | 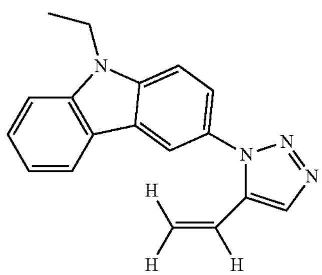 [SMILES: C=Cc1cnnn1-c1ccc2c(c1)c1ccccc1n2CC] | n/a | n/a | $^1$H-NMR (400 MHz, CDCl$_3$) δ 1.48 (t, J = 7.2, 3H), 2.95 (s, 3H), 3.20 (t, J = 6.4, 2H), 4.43 (t, J = 6.4, 2H), 4.45 (q, J = 7.2, 2H), 5.47 (d, J = 11.4, 1H), 5.84 (d, J = 17.6, 1H), 6.52 (dd, J = 17.6 and 11.4 H, 1H), 7.29 (dd, J = 7.2 1H), 7.47-7.57 (m, 4H), 7.95 (s, 1H), 8.10 (d, J = 7.8, 1H), 8.18 (t, J = 1.6, 1H) | 9-ethyl-3-(5-vinyl-1H-1,2,3-triazol-1-yl)-9H-carbazole |
| I-11 | 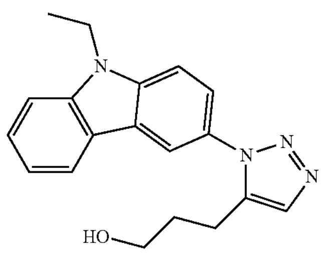 [SMILES: CCn1c2ccccc2c2cc(-n3nncc3CCCO)ccc21] | n/a | n/a | $^1$H-NMR (400 MHz, CDCl$_3$) δ 1.40 (t, J = 7.2, 3H), 1.80 (q, J = 7.6, 2H), 2.75 (t, J = 7.8, 2H), 3.78 (t, J = 6.2, 2H), 4.32 (q, J = 7.2, 2H), 7.23 (dd, J = 7.6, 1H), 7.44-7.55 (m, 4H), 7.60 (s, 1H), 8.03 (d, J = 7.6, 1H), 8.13 (s, 1H) | 4-(2-(1-(9-ethyl-9H-carbazol-3-yl)-1H-1,2,3-triazol-5-yl)eth-yl)morpholine |
| I-12 | 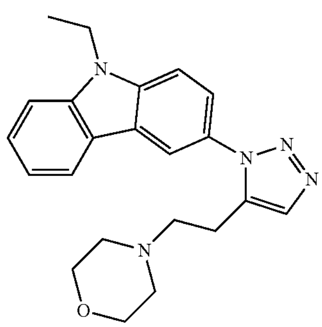 [SMILES: CCn1c2ccccc2c2cc(-n3nncc3CCN3CCOCC3)ccc21] | n/a | n/a | $^1$H-NMR (400 MHz, CDCl$_3$) δ 1.49 (t, J = 7.6, 3H), 2.39 (m, 4H), 2.60 (t, J = 7.6, 2H), 2.88 (t, J = 7.6, 2H), 3.66 (m, 4H), 4.45 (q, J = 7.6, 2H), 7.29 (dd, J = 7.6, 1H), 7.47-7.58 (m, 4H), 7.71 (s, 1H), 8.11 (d, J = 7.6, 1H), 8.15 (d, J = 1.4, 1H). | 4-(2-(1-(9-ethyl-9H-carbazol-3-yl)-1H-1,2,3-triazol-5-yl)eth-yl)morpholine |

TABLE 2

Effect of MBQ-167 on Rho GTPase activity (Active Rho GTPase/Total Rho GTPase) following 24 h in MDA-MB-231 cells, relative to vehicle (=1)

| Rho GTPase | Attached cells | Detached cells |
|---|---|---|
| Rac | 0.74* | 0.23* |
| Cdc42 | 0.39* | 0.22* |
| Rho | 0.9 | 0.85 |

*p < 0.05

MDA-MB-231 human breast cancer cells were treated for 24 h with 250 nM MBQ-167. The attached and detached cell populations were recovered and equal amounts of proteins subjected to pulldown assays using the p21-binding domain of PAK to isolate the GTP bound Rac and Cdc42, or the Rho binding domain from Rhotekin to isolate active Rho. Cell lysates were western blotted with antibodies to Rac, Cdc42, or Rho. Results from positive bands in western blots were quantified using image J. The integrated density for active Rho GTPase (Rac, Cdc42, Rho.GTP) was divided by the total Rho GTPase (Rac, Cdc42, Rho) from the same cell lysates. Rac, Cdc42, or Rho activity for each MBQ-167 treatment was divided by the vehicle controls for each experiment to obtain Relative Rho GTPase activity.

TABLE 3

Effect of MBQ-167 on Rac activity (Active Rac/Total Rac) following 24 h in MCF-7 cells

| MBQ-167 nM | Rac Activity |
|---|---|
| 0 | 1.0 |
| 250 | 1.075 ± 0.3 |

MCF-7 human breast cancer cells were treated for 24 h with 250 nM MBQ-167. Cells were lysed and equal amounts of proteins subjected to pulldown assays using the p21-binding domain of PAK to isolate the GTP bound Rac. Cell lysates were western blotted with antibodies to Rac, Cdc42, or Rho. Results from positive bands in western blots were quantified using image J. The integrated density for active Rac (Rac.GTP) was divided by the total Rac from the same cell lysates (N=2).

TABLE 4

Optimal % Treated (T)/Control (C) for mammary fat pad tumor growth for MBQ-167 treated nude mice.

| Treatment mg/kg BW | Optimal % Change in Tumor Size |
|---|---|
| 0 | 100 |
| 1 | 58 |
| 10 | 9 |

As adapted from (Alley et al., Chapter 7, Human tumor xenograft models in NCI drug development, from Anticancer drug development guide BA Teicher and PA Andrews, Eds, 2004, Humana Press, Inc., NJ), % Change for tumors from mice that received MBQ-167 treatment was calculated as: % T/C=(delta T/delta C)×100 when delta T>0

Delta T=average tumor size on day 65 of treated mice-average tumor size on day 01 of treated mice. Delta C=average tumor size on day 65 of control mice-average tumor size on day 01 of control mice.

TABLE 5

Tumor growth delay for MBQ-167-treated mice

| Treatment mg/kg BW | Time in Days for Doubling of Tumor size | | | |
|---|---|---|---|---|
| | $2^1$ | $2^2$ | $2^3$ | $2^4$ |
| 0 | 8 | 14.5 | 27.7 | 33.3 |
| 1 | 10 | 30 | 57 | — |
| 10 | 11 | 30 | — | — |

As adapted from (Alley et al., Chapter 7, Human tumor xenograft models in NCI drug development, from Anticancer drug development guide BA Teicher and PA Andrews, Eds, 2004, Humana Press, Inc., NJ), Tumor growth delay was calculated as the percentage by which the treated group tumor size is delayed in attaining a specified number of doublings (from day 1) compared with controls using:

[(T−C)/C]×100, where T and C are the median times in days for treated and control groups to attain a doubling in tumor size.

PUBLICATIONS

These publications are incorporated by reference to the extent they relate materials and methods disclosed herein.
Alley M C, et al. In: B. A. Teicher and P. A. Andrews (eds.), Cancer drug discovery and development, Humana Press, Inc: Totowa, N.J.; 2004. p. 125-52.
Baugher P J, et al. Breast Cancer Res 2005; 7: R965-R$^{74}$.
Boettner B, Van Aelst L. Gene 2002; 286:155-74.
Bouvet M, Hoffman R M. Methods Mol Biol 2015; 1267: 321-48.
Burridge K, et al. Trends Cell Biol 1997; 7: 342-47.
Carpenter R L, Lo H W. Cancers (Basel), 2014; 6: 897-925.
Castillo-Pichardo L, et al. Transl Oncol 2014; 7: 546-55.
Chircop M. Small Gtpases 2014; 5:e29770.
Chong C, et al. J Biol Chem 2001; 276:17347-53.
Coniglio S J, et al. J Biol Chem 2001; 276:28113-120.
Crawford J J, et al. Expert Opin Ther Pat 2012; 22:293-310.
de la Parra C, et al. J Biol Chem 2015; 290:6047-57.
Dharmawardhane S., et al. Enzymes 2013; 33 Pt A:117-46.
Dokmanovic M, et al. Mol Cancer Ther 2009; 8:1557-69.
Edwards D C, et al. Nat Cell Biol 1999; 1:253-59.
Etienne-Manneville S, Hall A. Curr Opin Cell Biol 2003; 15: 67-72.
Faruqi T R, et al. Proc Natl Acad Sci U.S.A 2001; 98: 9014-19.
Frisch S M, Ruoslahti E. Curr Opin Cell Biol 1997; 9:701-06.
Gao Y., et al. Proc Natl Acad Sci U.S.A 2004; 101: 7618-23.
Hernandez E, et al. P R Health Sci J 2010; 29:348-56.
Hernandez E, et al. U.S. Pat. No. 8,884,006B2, Nov. 11, 2014; U.S. Pat. No. 9,278,956B1, Mar. 8, 2016.
Humphries-Bickley T, et al. J Chromatogr B Analyt Technol Biomed Life Sci 2015; 981-982C:19-26.
Krauthammer M., et al. Nat Genet 2012; 44:1006-14.
Kurisu S, et al. Oncogene 2005; 24:1309-19.
Maes H, et al. Cell Death Dis 2014; 5: e1127.
Manes T D, Pober J S. J Immunol 2013; 190: 3079-30.
Manser E, et al. Mol Cell Biol 1997; 17:1129-43.
Maroto B, et al. Oncogene 2008; 27:4900-08.
Marotta L L, et al. J Clin Invest 2011; 121: 2723-35.
Martin H, et al. J Clin Invest 2013; 123: 4449-63.
Mnaimneh, S., et al. Cell 2004; 118:31-44.
Montalvo-Ortiz B L, et al. J Biol Chem. 2012; 287:13228-238.
Oprea T I, et al. PLoS One 2015; 10: e0142182.
Phadke P A, et al. Clin Cancer Res 2006; 12: 1431-40.
Qiu R G, et al. Nature 1995; 374: 457-59.
Rane C K, Minden A. Small Gtpases 2014; 5:e28003.
Ridley A J. Curr Opin Cell Biol, 2015; 36: 103-12.
Rivera R A, et al. PLoS One 2016; 11: e0157251.
Rohatgi R, et al. Cell 1999; 97:221-31.
Schnelzer A., et al. Oncogene 2000; 19: 3013-20.
Sehl M E, et al. PLoS One 2015; 10: e0135797.
Shutes A, et al. J Biol Chem 2007; 282: 35666-78.
Simon A R, et al. Science 2000; 290:144-47.
Smith B N, Bhowmick N A. J Clin Med 2016; 5:E17.
Sosa M S, et al. Mol. Cell 2010; 40:877-92.
Stengel K, Zheng Y. Cell Signal 2011; 23: 1415-23.
Taddei M L, et al. J Pathol 2012; 226: 380-393.
Vigil D., et al. Nat Rev Cancer 2010; 10: 842-57.
Wertheimer E., et al. Cell Signal 2011; 24:353-62.
Ye D Z, Field J. Cell Logist 2012; 2:105-16.
Zins K, et al. PLoS One 2013; 8: e74924.

We claim:
1. A compound of formula (I),

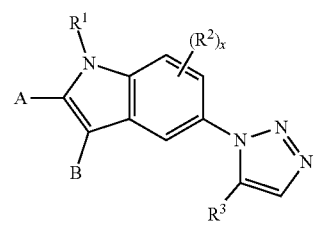

wherein A and B taken together with the ring to which they are attached form a $C_5$-$C_8$cycloalkyl, $C_6$-$C_{10}$ aryl, or a 5- to 8-membered heterocycloalkyl; wherein each hydrogen atom in $C_5$-$C_8$cycloalkyl, $C_6$-$C_{10}$ aryl, or 5- to 8-membered heterocycloalkyl is independently optionally substituted by deuterium, halogen, —OH, —CN, —OR$^4$, —OC$_1$—C$_6$ alkyl, —NH$_2$, —NH(C$_1$-C$_6$ alkyl), —N(C$_1$-C$_6$alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O) NHC$_1$—C$_6$ alkyl, —N(C$_1$-C$_6$ alkyl)C(O)NH$_2$, —N(C$_1$-C$_6$ alkyl)C(O)NHC$_1$—C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$—C$_6$ alkyl, —N(C$_1$-C$_6$ alkyl)C(O)OC$_1$—C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$—C$_6$ alkyl, —C(O)NH$_2$, —C(O)NH(C$_1$-C$_6$ alkyl), —C(O)N(C$_1$-C$_6$ alkyl)$_2$, —SC$_1$—C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, 3-to 7-membered heterocycloalkyl, —CF$_3$, —CHF$_2$, or —CH$_2$F;

R$^1$ is H, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl, or —OR$^5$;

each R$^2$ is independently deuterium, halogen, —OH, —CN, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —OR$^6$, —C(O)OR$^6$, —C(O)NR$^6$R$^7$, —NH$_2$, —NH(C$_1$-C$_6$ alkyl), —N(C$_1$-C$_6$ alkyl)$_2$, —NHC(O)C$_1$-C$_6$ alkyl, —CO$_2$H, —C(O)OC$_1$—C$_6$ alkyl, —C(O)NH$_2$, —C(O)NH(C$_1$-C$_6$ alkyl), —C(O)N(C$_1$-C$_6$ alkyl)$_2$, —SC$_1$—C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl); wherein each hydrogen atom in C$_1$-C$_6$ alkyl, C$_2$-C$_6$ alkenyl, C$_2$-C$_6$ alkynyl, C$_3$-C$_6$ cycloalkyl, and C$_6$-C$_{10}$ aryl is independently optionally substituted by deuterium, halogen, —OH, —CN, —OR$^6$, —OC$_1$—C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$—C$_6$ alkyl, —N(C$_1$-C$_6$ alkyl)C(O)NH$_2$, —N(C$_1$-C$_6$ alkyl)C(O)NHC$_1$—C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$—C$_6$ alkyl, —N(C$_1$-C$_6$ alkyl)C(O)OC$_1$—C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$—C$_6$ alkyl, —C(O)NH$_2$, —C(O)NH(C$_1$-C$_6$ alkyl), —C(O)N(C$_1$-C$_6$ alkyl)$_2$, —SC$_1$—C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3-to 7-membered heterocycloalkyl;

R$^3$ is H, deuterium, C$_1$-C$_6$ alkyl, C$_2$-C$_6$ alkenyl, C$_2$-C$_6$ alkynyl, C$_3$-C$_6$ cycloalkyl, 3-to 7-membered heterocycloalkyl, C$_6$-C$_{10}$ aryl, C$_6$-C$_{10}$ aryl-(C$_6$-C$_{10}$ aryl), C$_1$-C$_6$ alkyl-(NHR$^8$), C$_1$-C$_6$ alkyl-(OR$^8$), C$_6$-C$_{10}$ aryl-(OR$^8$), C$_1$-C$_6$ alkyl-(NR$^8$R$^9$), or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3-to 7-membered heterocycloalkyl, C$_6$-C$_{10}$ aryl, or mono- or bicyclic heteroaryl is optionally substituted by deuterium, halogen, —OH, oxo, —OR$^8$, —NHR$^8$, —CN, —OC$_1$—C$_6$ alkyl, —NH$_2$, —NH(C$_1$-C$_6$ alkyl), —NH(C$_6$-C$_{10}$ aryl), —NH(C$_6$-C$_{10}$ aryl)-N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$—C$_6$ alkyl, —N(C$_1$-C$_6$ alkyl)C(O)NH$_2$, —N(C$_1$-C$_6$ alkyl)C(O)NHC$_1$—C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$—C$_6$ alkyl, —N(C$_1$-C$_6$ alkyl)C(O)OC$_1$—C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$—C$_6$ alkyl, —C(O)NH$_2$, —C(O)NH(C$_1$-C$_6$ alkyl), —C(O)N(C$_1$-C$_6$ alkyl)$_2$, —SC$_1$—C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_1$-C$_6$ alkyl, C$_2$-C$_6$ alkenyl, C$_2$-C$_6$ alkynyl, C$_3$-C$_6$ cycloalkyl, 3-to 7-membered heterocycloalkyl, C$_1$-C$_6$ alkyl-(3-to 7-membered heterocycloalkyl), —CF$_3$, —CHF$_2$, or —CH$_2$F;

each R$^4$, R$^5$, R$^6$, R$^7$, R$^8$, and R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, C$_1$-C$_6$ alkyl-(3-to 7-membered heterocycloalkyl), heteroaryl, —S(O)$_2$C$_1$-C$_6$ alkyl, —CF$_3$, —CHF$_2$, or —CH$_2$F, wherein each hydrogen in C$_6$-C$_{10}$ aryl is optionally substituted by C$_3$-C$_6$ cycloalkyl, 3- to 7-membered heterocycloalkyl, or —CH$_2$CN; and x is 0, 1, 2, or 3;

or a pharmaceutically acceptable salt thereof.

2. The compound of claim 1, wherein A and B taken together with the ring to which they are attached form a C$_6$-C$_{10}$ aryl, wherein each hydrogen atom in C$_6$-C$_{10}$ aryl is independently optionally substituted by deuterium, halogen, —OH, —CN, —OR$^4$, —OC$_1$—C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$—C$_6$ alkyl, —N(C$_1$-C$_6$ alkyl)C(O)NH$_2$, —N(C$_1$-C$_6$ alkyl)C(O)NHC$_1$—C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$—C$_6$ alkyl, —N(C$_1$-C$_6$ alkyl)C(O)OC$_1$—C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$—C$_6$ alkyl, —C(O)NH$_2$, —C(O)NH(C$_1$-C$_6$ alkyl), —C(O)N(C$_1$-C$_6$ alkyl)$_2$, —SC$_1$—C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, —C$_3$-C$_6$ cycloalkyl, 3-to 7-membered heterocycloalkyl, —CF$_3$, —CHF$_2$, or —CH$_2$F, or a pharmaceutically acceptable salt thereof.

3. The compound of claim 1, wherein R$^1$ is H, C$_1$-C$_6$ alkyl, C$_2$-C$_6$ alkenyl, C$_2$-C$_6$ alkynyl, C$_3$-C$_6$ cycloalkyl, or 3-to 7-membered heterocycloalkyl, wherein each hydrogen atom in C$_1$-C$_6$ alkyl, C$_2$-C$_6$ alkenyl, C$_2$-C$_6$ alkynyl, C$_3$-C$_6$ cycloalkyl, or 3- to 7-membered heterocycloalkyl is independently optionally substituted by deuterium, halogen, C$_1$-C$_6$ alkyl, C$_1$-C$_6$ haloalkyl, or —OR$^5$, or a pharmaceutically acceptable salt thereof.

4. The compound of claim 1, wherein R$^3$ is C$_1$-C$_6$ alkyl, C$_2$-C$_6$ alkenyl, C$_6$-C$_{10}$ aryl, C$_1$-C$_6$ alkyl-(OR$^8$), C$_6$-C$_{10}$ aryl-(OR$^8$), or monocyclic heteroaryl; wherein each hydrogen atom in C$_1$-C$_6$ alkyl, C$_2$-C$_6$ alkenyl, C$_6$-C$_{10}$ aryl, or monocyclic heteroaryl is optionally substituted by deuterium, halogen, —OH, oxo, —OR$^8$, —NHR$^8$, —CN, —OC$_1$—C$_6$ alkyl, —NH$_2$, —NH(C$_1$-C$_6$ alkyl), —NH(C$_6$-C$_{10}$ aryl), —NH(C$_6$-C$_{10}$ aryl)-N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$—C$_6$ alkyl, —N(C$_1$-C$_6$ alkyl)C(O)NH$_2$, —N(C$_1$-C$_6$ alkyl)C(O)NHC$_1$—C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$—C$_6$ alkyl, —N(C$_1$-C$_6$ alkyl)C(O)OC$_1$—C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$—C$_6$ alkyl, —C(O)NH$_2$, —C(O)NH(C$_1$-C$_6$ alkyl), —C(O)N(C$_1$-C$_6$ alkyl)$_2$, —SC$_1$—C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_1$-C$_6$ alkyl, C$_2$-C$_6$ alkenyl, C$_2$-C$_6$ alkynyl, —C$_3$-C$_6$ cycloalkyl, 3-to 7-membered heterocycloalkyl, C$_1$-C$_6$ alkyl-(3-to 7-membered heterocycloalkyl), —CF$_3$, —CHF$_2$, or —CH$_2$F, or a pharmaceutically acceptable salt thereof.

5. The compound of claim 1, wherein R$^3$ is C$_1$-C$_6$ alkyl, C$_2$-C$_6$ alkenyl, C$_6$-C$_{10}$ aryl, C$_1$-C$_6$ alkyl-(OR$^8$), C$_6$-C$_{10}$ aryl-(OR$^8$), or monocyclic heteroaryl; wherein each hydrogen atom in C$_1$-C$_6$ alkyl, C$_2$-C$_6$ alkenyl, C$_6$-C$_{10}$ aryl, or monocyclic heteroaryl is optionally substituted by deuterium, halogen, —OH, —OR$^8$, —OC$_1$—C$_6$ alkyl, C$_1$-C$_6$ alkyl, or 3-to 7-membered heterocycloalkyl, or a pharmaceutically acceptable salt thereof.

6. The compound of claim 5, wherein R is C$_1$-C$_6$ alkyl, or a pharmaceutically acceptable salt thereof.

7. The compound of claim 6, wherein x is 0, or a pharmaceutically acceptable salt thereof.

8. The compound of claim 7, wherein R$^3$ is independently deuterium, C$_1$-C$_6$ alkyl, C$_2$-C$_6$ alkenyl, C$_2$-C$_6$ alkynyl, C$_3$-C$_6$ cycloalkyl, 3-to 7-membered heterocycloalkyl, C$_6$-C$_{10}$ aryl, C$_6$-C$_{10}$ aryl-(C$_6$-C$_{10}$ aryl), C$_1$-C$_6$ alkyl-(NHR$^8$), C$_1$-C$_6$ alkyl-(OR$^8$), C$_6$-C$_{10}$ aryl-(OR$^8$), C$_1$-C$_6$ alkyl-(NR$^8$R), or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3-to 7-membered heterocycloalkyl, C$_6$-C$_{10}$ aryl, or mono- or bicyclic heteroaryl is optionally substituted by deuterium, halogen, —OH, oxo, —OR$^8$, —NHR$^8$, —CN, —OC$_1$—C$_6$ alkyl, —NH$_2$, —NH(C$_1$-C$_6$ alkyl), —NH(C$_6$-C$_{10}$ aryl), —NH(C$_6$-C$_{10}$ aryl)-N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$—C$_6$ alkyl, —N(C$_1$-C$_6$ alkyl)C(O)NH$_2$, —N(C$_1$-C$_6$ alkyl)C(O)NHC$_1$—C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$—C$_6$ alkyl, —N(C$_1$-C$_6$ alkyl)C(O)OC$_1$—C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$—C$_6$ alkyl, —C(O)NH$_2$, —C(O)NH(C$_1$-C$_6$ alkyl), —C(O)N(C$_1$-C$_6$ alkyl)$_2$, —SC$_1$—C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_1$-C$_6$ alkyl, C$_2$-C$_6$ alkenyl, C$_2$-C$_6$ alkynyl, C$_3$-C$_6$ cycloalkyl, 3-to 7-membered heterocycloalkyl, C$_1$-C$_6$ alkyl-(3-to 7-membered heterocycloalkyl), —CF$_3$, —CHF$_2$, or —CH$_2$F, or a pharmaceutically acceptable salt thereof.

9. The compound of claim 8, wherein A and B taken together with the ring to which they are attached form phenyl, or a pharmaceutically acceptable salt thereof.

10. A method of treating a disease in a patient, the method comprising administering to the patient in need thereof an effective amount of a compound according to claim 1, wherein the disease is a cancer selected from the group consisting of breast cancer, pancreatic cancer, ovarian cancer, gastric cancer, and neuronal cancer.

11. The method of claim 10, wherein the compound inhibits cancer cell migration, induces cell cycle arrest of a diseased cell, induces apoptosis of a diseased cell, reduces the expression of a Bcl-2 protein, inhibits mammosphere formation, or a combination thereof.

12. The method of claim 10, wherein the disease is mediated by a GTPase.

13. The method of claim 12, wherein the GTPase is Rac 1 or Cdc42.

14. The method of claim 10, wherein the effective amount of the compound is in a range of about 0.01 mg/kg to about 100 mg/kg of body weight of the patient.

15. The method of claim 10, wherein the cancer is ovarian cancer or breast cancer.

16. The method of claim 10, wherein the cancer is ovarian cancer.

17. The method of claim 10, wherein the cancer is breast cancer.

* * * * *